(12) United States Patent
Levy et al.

(10) Patent No.: US 11,779,371 B1
(45) Date of Patent: Oct. 10, 2023

(54) IMPLANT DELIVERY DEVICE

(71) Applicant: Expand Medical Ltd., Amirim (IL)

(72) Inventors: Arie Levy, Shoam (IL); Ofek Levin, Amirim (IL)

(73) Assignee: Expand Medical Ltd., Amirim (IL)

( * ) Notice: Subject to any disclaimer, the term of this patent is extended or adjusted under 35 U.S.C. 154(b) by 0 days.

(21) Appl. No.: 18/138,238

(22) Filed: Apr. 24, 2023

Related U.S. Application Data

(63) Continuation of application No. 18/162,270, filed on Jan. 31, 2023.

(60) Provisional application No. 63/420,226, filed on Oct. 28, 2022.

(51) Int. Cl.
 *A61B 17/34* (2006.01)
 *A61B 17/28* (2006.01)
 *A61F 2/08* (2006.01)

(52) U.S. Cl.
 CPC ...... *A61B 17/3468* (2013.01); *A61B 17/2841* (2013.01); *A61B 2017/2845* (2013.01); *A61F 2/08* (2013.01)

(58) Field of Classification Search
 CPC ............ A61F 2002/0072; A61F 2/0063; A61F 2/0095; A61F 2/011; A61F 2/04; A61F 2/08; A61F 2/0811; A61F 2/148; A61F 2/844; A61F 2/95; A61F 2/9517; A61B 17/22031; A61B 17/2841; A61B 17/29; A61B 17/2909; A61B 17/3468
 See application file for complete search history.

(56) References Cited

U.S. PATENT DOCUMENTS

| | | | |
|---|---|---|---|
| 5,263,969 | A | 11/1993 | Phillips |
| 5,464,403 | A | 11/1995 | Kieturakis et al. |
| 5,957,939 | A * | 9/1999 | Heaven ............ A61B 17/00234 606/151 |
| 6,416,506 | B1 * | 7/2002 | Tilton, Jr. ........ A61B 17/00234 606/1 |
| 7,235,043 | B2 | 6/2007 | Gellman et al. |
| 7,559,941 | B2 | 7/2009 | Zannis et al. |
| 7,819,880 | B2 | 10/2010 | Zannis et al. |
| 8,097,008 | B2 | 1/2012 | Henderson |
| 8,241,298 | B2 | 8/2012 | Sengun et al. |
| 8,435,305 | B2 | 5/2013 | Lozier et al. |
| 8,579,989 | B2 | 11/2013 | Leahy |
| 8,585,773 | B1 * | 11/2013 | Kucklick ............... A61B 17/34 623/23.72 |
| 8,617,188 | B2 | 12/2013 | Dudai |
| 8,673,021 | B2 | 3/2014 | Orr et al. |
| 8,734,473 | B2 | 5/2014 | Levin et al. |
| 8,753,359 | B2 | 6/2014 | Levin et al. |

(Continued)

*Primary Examiner* — Sarah W Aleman
(74) *Attorney, Agent, or Firm* — Withers Bergman LLP

(57) ABSTRACT

Surgical delivery devices of the invention have a delivery shaft extending from a handle, with a deformable member such as a plate or a leaf at a distal portion of the shaft with a surface carrying an implant for orthopedic surgery. A trigger or lever on the device positions the deformable member between a first cylindrical configuration that can pass through a cannula used in arthroscopic surgery and a second, substantially flat configuration useful to place the implant on tissue during the arthroscopic surgery. Preferably the trigger may be operated to hold the deformable plate or leaf in any of a continuum of positions between the first cylindrical configuration and the second, substantially flat configuration.

20 Claims, 41 Drawing Sheets

(56) References Cited

U.S. PATENT DOCUMENTS

| | | |
|---|---|---|
| 8,821,507 B2 | 9/2014 | Alexson, Jr. et al. |
| 8,864,780 B2 | 10/2014 | Euteneuer et al. |
| 8,906,045 B2 * | 12/2014 | Levin ............... A61B 17/00491 |
| | | 606/151 |
| 8,998,949 B2 | 4/2015 | Stone et al. |
| 9,005,224 B2 | 4/2015 | Euteneuer et al. |
| 9,101,460 B2 | 8/2015 | Euteneuer et al. |
| 9,113,977 B2 | 8/2015 | Euteneuer et al. |
| 9,179,910 B2 | 11/2015 | Euteneuer et al. |
| 9,179,961 B2 | 11/2015 | Euteneuer et al. |
| 9,198,751 B2 | 12/2015 | Euteneuer et al. |
| 9,314,331 B2 | 4/2016 | Euteneuer et al. |
| 9,572,558 B2 | 2/2017 | Grant et al. |
| 9,713,418 B2 | 7/2017 | Huszar et al. |
| 9,827,111 B2 | 11/2017 | Orr et al. |
| 9,943,351 B2 | 4/2018 | Mcdonnell et al. |
| 9,974,638 B2 | 5/2018 | Zoll et al. |
| 10,085,785 B2 | 10/2018 | Euteneuer et al. |
| 10,195,016 B2 | 2/2019 | Euteneuer et al. |
| 10,226,325 B2 | 3/2019 | Euteneuer et al. |
| 10,258,459 B2 | 4/2019 | Zenz-Olson |
| 10,278,801 B2 | 5/2019 | Kucklick |
| 10,307,238 B2 | 6/2019 | Kucklick |
| 10,314,689 B2 | 6/2019 | Zenz-Olson et al. |
| 10,398,579 B2 | 9/2019 | Faizer |
| 10,413,397 B2 | 9/2019 | Euteneuer et al. |
| 10,449,031 B2 | 10/2019 | Euteneuer et al. |
| 10,610,389 B2 | 4/2020 | Becking et al. |
| 10,758,332 B2 | 9/2020 | Richard et al. |
| 10,835,235 B2 | 11/2020 | Coleman |
| 10,835,368 B2 | 11/2020 | Zenz-Olson et al. |
| 10,874,503 B2 | 12/2020 | Zenz-Olson et al. |
| 10,881,441 B2 | 1/2021 | Euteneuer et al. |
| 10,912,579 B2 | 2/2021 | Kucklick |
| 10,952,783 B2 | 3/2021 | Euteneuer et al. |
| 10,973,656 B2 | 4/2021 | Kleiner et al. |
| 10,987,210 B2 | 4/2021 | Zenz-Olson et al. |
| 11,051,932 B2 | 7/2021 | Euteneuer et al. |
| 11,116,623 B2 | 9/2021 | Euteneuer et al. |
| 11,185,402 B2 | 11/2021 | Kucklick |
| 11,197,675 B2 | 12/2021 | Adinolfi |
| 11,229,509 B2 | 1/2022 | Kucklick |
| 11,259,939 B2 | 3/2022 | Churchill et al. |
| 11,331,180 B2 | 5/2022 | Zenz-Olson |
| 11,382,647 B2 | 7/2022 | Wallace et al. |
| 11,413,082 B2 | 8/2022 | Euteneuer et al. |
| 11,413,133 B2 | 8/2022 | Euteneuer et al. |
| 2013/0035704 A1 * | 2/2013 | Dudai ................... A61F 2/0063 |
| | | 606/151 |
| 2019/0350608 A1 | 11/2019 | Kucklick |
| 2021/0121191 A1 | 4/2021 | Kucklick |
| 2022/0054248 A1 | 2/2022 | Kucklick |

* cited by examiner

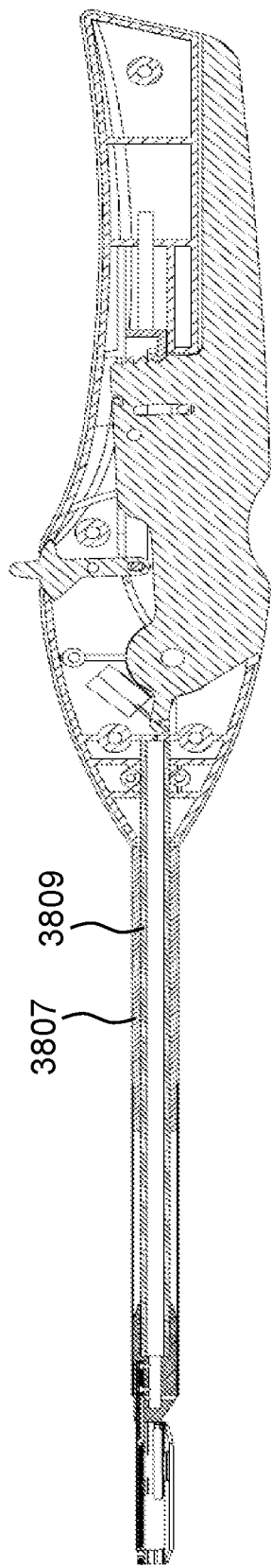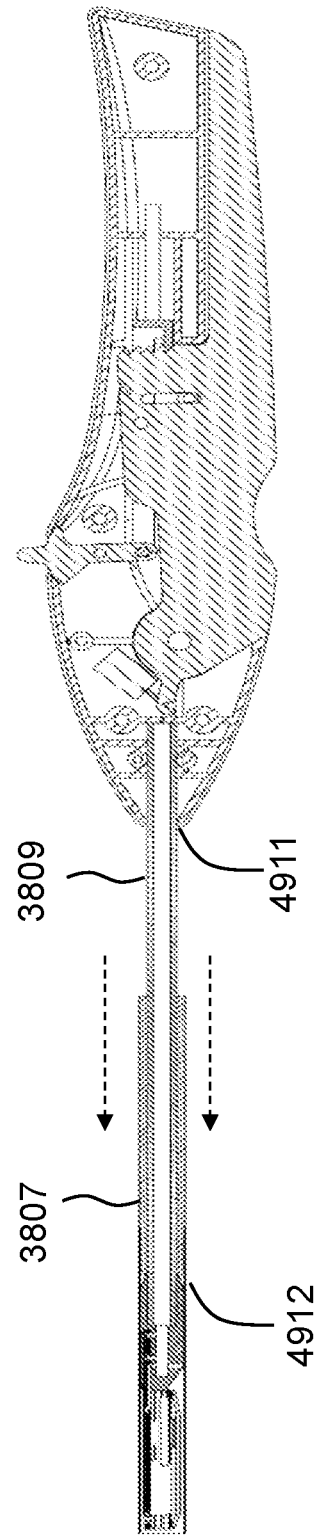

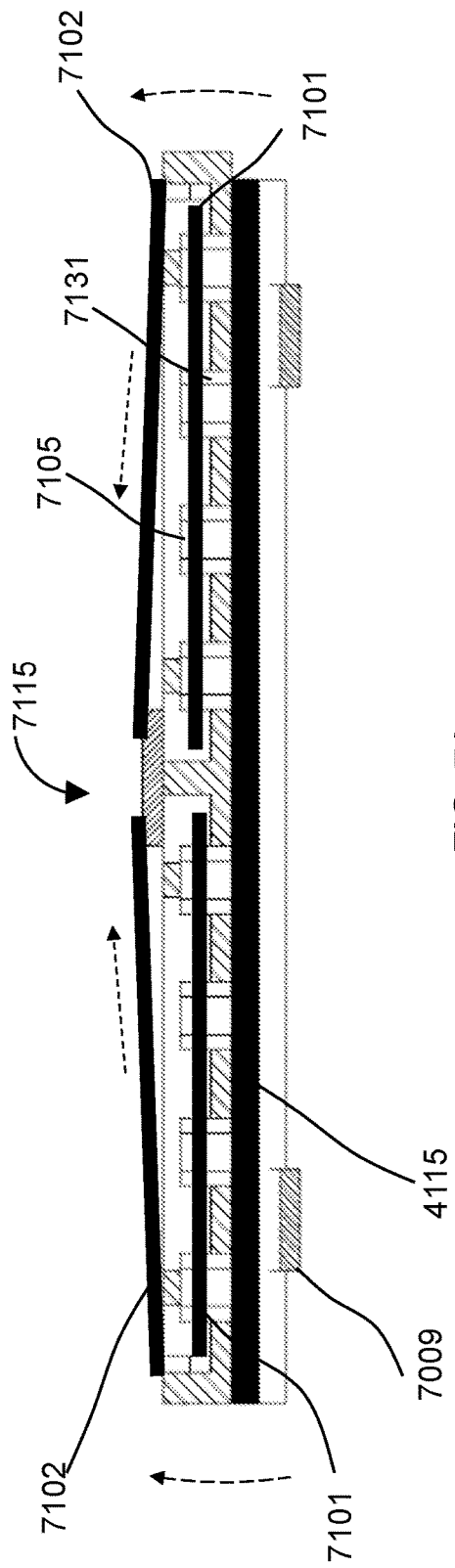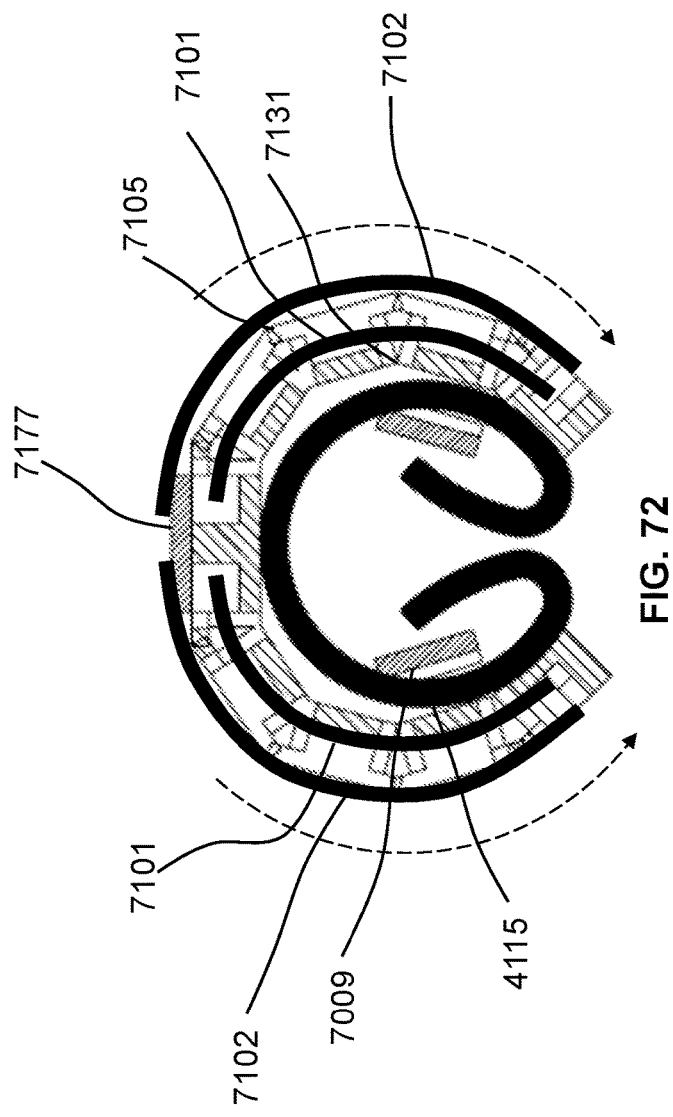

IMPLANT DELIVERY DEVICE

TECHNICAL FIELD

The invention relates to devices that deliver and spread an orthopedic implant.

BACKGROUND

Injury or damage to joints in the body can be very painful. Common causes of such injury include intense activity and age-related tissue deterioration. For example, ligament tears may arise from degenerative changes that occur with aging or from acute injuries during sports or other intensive activity. Treating those injuries to the musculoskeletal system is what defines the medical specialties of orthopedics and orthopedic surgery. Common orthopedic surgeries include repairs of the spine, shoulder, hand, hip, or knee, among others.

For example, some people may suffer from a painful shoulder injury in the form a tear to one of a group tendons in the shoulder known as the rotator cuff. A complete tear of a rotator cuff tendon can be very painful and cause the loss of arm function. Orthopedic surgeries address those injuries. Some approaches to orthopedic surgery use an implant, or graft, as a patch of biocompatible material such as collagen to anchor a separated tendon back to its original site of attachment.

Implants show promise in orthopedic surgery but are not without drawbacks. For example, the practical reality of surgical conditions limits the precision of positioning, tensioning, and attaching an implant. Perhaps as a consequence, literature suggests that after shoulder surgery, rates of adverse events may be higher than expected. See Craig, 2019, BMJ 364:L298, incorporated by reference. People with painful joint injuries may have to choose between an uncertain surgical outcome and continued experience of chronic joint pain.

SUMMARY

The present invention provides methods and devices for delivering and deploying an orthopedic implant. Methods and device of the invention are useful in an arthroscopic surgery setting in which materials are delivered through an incision, optionally through cannula with a bore typically no bigger than about 1 cm in diameter. Surgical delivery devices of the invention have a delivery shaft extending from a handle, and the distal end of the shaft has a head, a deformable member sometimes herein referred to as a plate or a leaf that has a surface for carrying a sheet-like implant, such as one of the approximately postage-stamp sized collagen (or similar) patches used in orthopedic surgery.

In some embodiments, an implant delivery device of the invention has a deformable plate or leaf for deployment of a graft that is normally in an open position. The plate has a surface to which a graft or implant may be temporarily fixed, allowing the device to carry the implant to a surgery site such as damaged tissue. The implant delivery device includes a mechanism to deform or compress the plate (and the attached implant) to allow the plate and implant to be passed through a surgical incision. In a preferred embodiment, a trigger is squeezed to pull the plate into a curved closed, substantially cylindrical conformation that fits through a narrow opening such as a surgical incision or optionally a trocar or cannula as may be used in arthroscopic or keyhole surgery. The deformable plate preferably is made of a material with elastic properties. The handle of the implant delivery device includes a trigger or similar mechanism that tensions a wire to curl the plate away from its resting, default flat shape and into the substantially cylindrical position. This may be done by one or more tension wires running from the trigger, through a delivery shaft of the device, and through a channel within the deformable plate. The plate includes hinges, such as a set of parallel channels that define a system of living hinges, such that tensioning the wire deforms the plate into the substantially cylindrical shape. Because the plate is a made of a material with elastic properties, when the tension is released, the plate relaxes back to its resting, flat, open configuration. In such embodiments, a clinician maintains a squeezing pressure on a trigger to hold the plate (and graft or implant) in the rolled, cylindrical position. Embodiments of the invention disclosed herein also include version in which the plate is substantially cylindrical at rest, but may be elastically deformed to the flat, open configuration.

Embodiments of the invention also include a graft attachment mechanism, for holding the implant or graft to the plate during delivery, an insertion sleeve that is attached to the delivery shaft and obviates the requirement for a cannula to be placed within a surgical incision, and a loading card that aids in hassle-free loading of an implant on to the plate.

Preferred embodiments of the graft attachment mechanism include one or more clips on and over a surface of the plate. Each clip may have an elongated arm with an attached hinge first end and an unattached compressing clip second end. The first end is elastically mounted to the plate, allowing the elongated arm to be deformed away from the plate, allowing the compressing clip end to be lifted off of the surface of the plate, which allows an implant to be slid into position on the plate. While various embodiments are disclosed and included within the scope of the disclosure, preferred embodiments of the grant attachment mechanism include at least a pair of claims that extend substantially parallel to an axis of a shaft of the device. The proximal end of each clip is elastically mounted to the surface of the plate while the distal end of each clip provides a compressing clip mechanism. Those clips may include a lever extending proximally of the proximal end allowing a user to squeeze the lever to open the distal end. In this preferred embodiment, the pair of clips are attached at a proximal portion of the plate and open towards the distal direction. When an implant is held by the clips and has been anchored or attached to tissue, the implant delivery device may be drawn in a proximal direction to pull the device (and plate) off of the implant, release the implant, and leave the implant in position on the tissue after the delivery device is removed from the site.

Other preferred embodiments of an implant delivery device include an insertion sleeve, which may be a substantially tubular or cylindrical member mounted over a delivery shaft of the device. The insertion sleeve may be slideable in a proximal and a distal direction along the shaft. By default, the sleeve rest in a proximal position, with the deformable plate extending past a distal portion of the sleeve, with the deformable plate resting in its open, flat position. A clinician can mount a graft or implant onto the deformable plate and then operate the trigger to roll the deformable plate (and graft) into the substantially cylindrical position. The, the insertion sleeve can be slid in a distal direction over the shaft, which draws the delivery plate into the insertion sleeve. Because the deformable plate and the graft (or implant) that it carries are pulled into a substantially cylindrical configuration and drawn into an interior bore of the insertion sleeve, the device can be used in arthroscopic or keyhole surgery by inserting the insertion sleeve through a surgical incision. A benefit of the insertion sleeve is that it encloses the graft and deployment plate during surgical access. This protects both the tissue (e.g., around the incision) and the graft during delivery of the graft to the surgical site. The insertion sleeve may include a domed or conical tip, optionally a split-opening two-part tapered tip that opens to allow the plate to extend from the insertion sleeve but also closes to form a tapered section to aid in atraumatic insertion through an incision. In fact, a main beneficial feature of the insertion sleeve is that the insertion sleeve provide the implant delivery device a mechanism by which to carry a graft or implant through a surgical incision for use during arthroscopic or keyhole surgery. The insertion sleeve may be present with a tubular or cylindrical body slidably mounted over a delivery shaft of the implant delivery device. Because the implant delivery device includes the insertion sleeve, there is no requirement to have a separate cannula or trocar positioned within the incision.

Another feature of embodiments of the disclosure is a loading card. While various shapes, materials, or features of a loading card are within the scope of the disclosure, the loading card, generally, refers to a separate piece that is provided pre-positioned within a graft attachment mechanism that biases the graft attachment mechanism into a graft receiving position during and until placement of an implant or graft within the mechanism. The loading card may be disposable, sterile card or member that simply holds the mechanism, e.g., one more clips, into at least a partially open shape. For example, where the graft attachment mechanism includes at least a pair of clips open, e.g., towards a distal end of the device, the loading card maybe a small fiberboard or polymer card that is provided, siting within the clips, holding the clips at least a little bit open. A clinical can load the device by sliding an implant or graft under the clips. The loading card holds the clips up and off of a surface of the deployment plate, so that the compression clip ends of the arms of the clips do not tear, damage, or interfere with the implant. Once the implant is positioned on the plate, the loading card may be slid out of (e.g., sideways from the arms of) the clips. The clips then compress onto the implant, holding the implant in position on the deployment plate. The loading card may simply be thrown away.

A surgeon may operate a trigger or lever on the device to wrap the deformable member between one substantially cylindrical position, in which the surface is curled closed, so that the head and implant can pass through the cannula and another flat position in which the surface is open and flat, allowing the implant to be placed on tissue. In fact, the trigger or lever may be progressively operated to hold the deformable head member in any of a continuum of positions between curled closed and opened flat. Device of the invention may be used in a variety of surgical settings including minimally invasive surgeries such as laparoscopic and endoscopic surgeries.

Beneficially, devices of the invention do not use the cannula or a sheath to constrain the implant in a collapsed position, which would allow the implant to spring open when released from enclosure. No, instead, mechanical features of the shaft, handle, and head move the implant to, and hold the implant in, the position desired by the user. Embodiments use a deformable member, or plate, as the head, e.g., made of a deformable plastic material. The plate may include parallel hinges allowing the plate to be moved between the open and closed positions. For example, the plate may be made up of adjacent panels with hinges along the edges held together with pins. In a preferred embodiment, the plate comprises a plastic or similar deformable material with one or more living hinges defined by channels or scores along a surface. The hinges allow the plate to be deformed to between the open/flat and closed/curled positions. The device further includes a mechanism to deform the plate, such as a wire extending through a channel around the plate and through the shaft back to the handle. The trigger/lever pulls the wire, which pulls the plate over axes of the hinges. When the wire is not under tension, the plastic material defaults to its curved/closed rest position and when the wire is pulled, the plastic material of the plate is pulled around the axes of the hinges, causing the plate to open to the flat position (or vice-versa). The surface of the plate may include a clip or pin to hold and carry an orthopedic implant against the surface. Because the device does not use shape-memory or super-elastic arms, the device does not simply spring between a constrained, closed position and an unconstrained, open position. Instead, the user controls the device to move the deformable plate between, and hold the deformable plate at, the open position, the closed position, and any of a continuum of positions therebetween.

A typical use case may involve arthroscopic surgery for rotator cuff repair. A surgeon would remove the device from the package, and the deformable delivery plate would be, at rest, in the curled closed position. The surgeon squeezes the trigger to open the deformable plate, exposing the delivery surface and retainer mechanism (e.g., clip). The surgeon positions the implant (e.g., an approximately 2.5 cm square sheet of collagen) on the surface and relax the trigger. In one set of embodiments, relaxing the trigger de-tensions the wire extending through the shaft and around the head. The material of the deformable plate returns to its cylindrical conformation, curling the implant closed within the now-cylindrical deformable plate. In another set of embodiments, the plate or head is open and flat by default, or when relaxed, and squeezing the trigger draws the head (or plate) into a cylindrical (or "closed") shape.

The surgeon can insert the closed plate with implant through a cannula in an incision in the shoulder of the patient. Some embodiments use an insertion sheath on the device and do not need a cannula; the insertion sheath enables insertion through an incision. Viewing the delivery plate on camera, the surgeon can operate the trigger to open the delivery plate, position the implant over and then onto the damaged soft tissue, and use a suturing device to attach the implant there. Then the implant delivery device can be lifted off of the implant, curled back closed, and withdrawn from the surgical site back through the cannula.

The deformable delivery plate, or leaf, is useful for delivering a sheet-like implant which itself may have any suitable shape such as rectangular, oval, irregular, etc. The delivery plate may also have any suitable such shape. Preferably, the deformable plate, or leaf—even if substantially rectangular—does not have orthogonal corners, but instead has a perimeter with curves or ramps. If the implant is in a curved closed configuration but is not quite smaller in diameter than the bore of the cannula, then curves or ramps along the perimeter will mean that pushing the deformable plate into the bore of the cannula will also deform the deformable plate closed by the final millimeter or so, in diameter, to fit within and through the cannula.

Another beneficial feature of the device is the ability of the user to hold the implant in a continuum of positions between open and closed, without relying on any sheath or cannula to restrain the deformable plate. This feature is useful for applications beyond re-attaching tendons to original anchoring surfaces on bone or tissue. For example, the device can be used to wrap an implant around a tendon or vessel, useful to repair or patch damaged vessels or ligaments or to perform a vascular anastomosis procedure or to fix an aneurism.

Notably, a feature of the device is that the deformable head does not use super-elastic or shape-memory "arms" or "struts" that spring open or snap open. Not only can the device be held at a continuum of positions, deployment of an implant need not involve any kinetic release with any shock or snap that could shake or jar a surgical positioning procedure. Moreover, positioning the implant between curled closed and open flat is uncoupled from unsheathing the implant from the cannula. Using a device of the invention, the implant may be passed through, and moved on a distance away from, the arthroscopic cannula or any sheath, all while being held in the curled closed position. Then, once positioned at the desired site, potentially spaced away from the cannula, so that the cannula is unable to interfere and out of site of the camera, then the implant can be opened in full view of the camera and positioned onto the tissue.

Using the aforementioned features, devices and methods of the invention provide for the delivery, spreading, positioning, and attachment of sheet-like implants during orthopedic surgery. Features of the device give the user a greater number of degrees of freedom than prior devices and move away from a prior approach in which a sheath constrains an implant until it snaps open. These devices of the invention promote great control over positioning and delivery, leading to better surgical outcomes. After a joint injury, the joint can be repaired by arthroscopic surgery using a device that optimizes implant positioning and attachment, thus optimizing surgical outcomes, thereby minimizing adverse outcomes or the need for further, additional surgery.

Aspects of the invention provide an implant delivery device. The device includes a handle, a shaft extending from the handle, and a deformable plate carried on a distal portion of the shaft. The deformable plate includes a first surface and preferably a second surface obverse to the first surface. The delivery device also includes a trigger on the handle such that the trigger is operably linked to the deformable plate. Importantly, the trigger is operable to pull the deformable plate between a cylindrical first configuration and a flat second configuration. Further, the device includes a retainer mechanism on the deformable plate (such as a pin or clip), such that the retainer mechanism is operable to releasably hold a sheet-like orthopedic implant against the first surface. The first surface of the deformable plate may be a single, monolithic piece of material. The deformable plate may include a plurality of parallel channels in the second surface that operate as a living hinge allowing the deformable plate to be pulled from the cylindrical first configuration to the flat second configuration. The device may include a wire extending from the trigger and through a loop channel within the deformable plate. Tensioning the wire by the trigger pulls the deformable plate between the cylindrical first configuration and the flat second configuration. The second surface may include extensions that overhang the channels, such that, when the deformable plate is pulled to the flat second configuration, the extensions prevent the deformable plate from deploying past about 180 degrees.

In some embodiments, the trigger may be moved to, and held in, a plurality of different positions between a rest position and tensioned position to thus hold the deformable plate in a respective plurality of different configurations between the cylindrical first configuration and the flat second configuration (or vice-versa). Further, in some embodiments, the deformable plate may be held, by one-handed operation of the trigger, in any position along a continuum between the cylindrical first configuration and the flat second configuration. The device may include a latch operably connected to the trigger and to the wire. A trigger spring may be operably connected to the trigger such that the latch is operable to lock the delivery platform into a fixed position.

In some embodiments, when the deformable plate of the device is in the cylindrical first configuration, the deformable plate may be inserted through a cannula used in arthroscopic keyhole surgery. The deformable plate may include one or more openings through which a surgical fastener may be delivered through the deformable plate and to or through a sheet-like orthopedic implant.

The deformable plate may include angled edges that bias the deformable plate into the cylindrical first configuration when the deformable plate is pushed into the bore of a trocar while the deformable plate is not fully in the cylindrical first position. Preferably the deformable plate include one or more hinges, each hinge having a hinge axis parallel to an axis of an idealized cylinder of the cylindrical first position. Further, the deformable plate, when carrying an implant patch, may be, by manual operation of the trigger, deformed around a ligament or vessel to wrap the implant patch around the ligament or vessel.

In certain aspects, the invention provides an implant delivery device that includes an extended shaft with a proximal portion and a distal portion; a handle, or a mechanism for attachment of the shaft to a handle or a robot, on the proximal portion of the shaft; and a furlable leaf at the distal portion of the shaft. The device includes a clip operable to releasably pin a sheet-like implant to a first face of the leaf and a tensioning member through the shaft tensionable to move the leaf between a curled first shape and a flat second shape. The leaf may include one or more hinges, each having a hinge axis parallel to an axis of the curled first shape. Preferably, the leaf is provided by a single, monolithic piece of material and the hinges are living hinges defined by channels in the material along each hinge axis along a second face of the leaf obverse to the first face. The living hinges may include overhanging ledges that limit opening of the furlable leaf beyond a predetermined amount (e.g., beyond flat). For example, the ledges may include first and second edges overhanging channels defining the living hinges, such that when the leaf is deformed in a flat position the first and second edges are in contact to prevent the leaf from deploying past 180 degrees. In preferred embodiments, the proximal portion of the shaft is attached to a handle. In certain embodiments, tensioning member includes a wire extending from the trigger on the handle mounted on the proximal portion, through the shaft, and through a channel within a second face of the leaf, such that squeezing the trigger pulls the wire in a proximal direction along the shaft, deforming the leaf from the curled first shape into the flat second shape. Preferably in these certain aspects, the sheet-like implant is slidable into the clip and is retained in the clip until released by the device. The shaft and the leaf, when in curled first shape, are sized to fit through a cannula, e.g., with an inner bore with a diameter of about 10 mm. The leaf may include ramped edges configured to push the leaf into curled first shape when the leaf is pushed or pulled into the bore of a cannula. Openings or holes through the leaf may be provided, through which a tack or suture may be delivered to the implant.

In related aspects, the invention provides devices that include a delivery shaft having a proximal portion and a distal portion, a handle or robot attachment at the proximal portion of the shaft, and a deformable leaf at the distal portion of the shaft. Specifically, the deployment support may be referred to as a leaf in being wide and thin and having a flat surface, or in being attached to a larger body (the shaft and handle) by one edge or end. The device may include a retainer mechanism such as a clip on the leaf to releasably hold a sheet-like implant against a first face of the leaf. While some embodiments contemplate attaching the shaft to a surgical robot or mechanical relay, in preferred embodiments, a trigger on the handle is operable to move the leaf between a cylindrical first configuration and a flat second configuration. In certain embodiments, the leaf is a smooth, essentially cylindrical piece of material at rest (like a plastic taco or plastic tube sliced along one side), but is plastically deformable into a more planar configuration under tension, e.g., of a wire. In preferred embodiments, the leaf has one or more hinges, each having a hinge axis parallel to an axis of the cylindrical first configuration. For example, in some embodiments, the leaf may further be provided by a single, monolithic piece of material and the hinges may be living hinges defined by channels or scorelines in or into the material along each hinge axis along a second face of the leaf obverse to the first face.

In some embodiments, the leaf includes one or more limiters such that deformation of the leaf encompasses only a range of configurations between substantially cylindrical and a predetermined patency such as substantially flat, but in which opening past a pre-defined amount, such as a 180-degree flat position, is prevented by the limiter(s). In some embodiments, the limiter comprises protrusions or overhangs over either or both edge of a channel defining a living hinge. When the leaf is deformed to a flat position, the overhang(s) block the leaf from opening beyond a pre-defined angle such as 180 degrees.

In some embodiments, the device may further include one or more wire(s) extending from the trigger, through the shaft, and through one or more channel(s) in, adjacent, or just under a second face of the leaf. Squeezing the trigger pulls the wire(s) in a proximal direction along the shaft, deforming the leaf from the cylindrical first configuration to the flat second configuration (or vice versa).

The handle of the device may further include a latch operably connected to the trigger and to the wire, and a trigger spring operably connected to the trigger. In some embodiments, the latch is operable to lock the leaf into a fixed configuration. In some embodiments, a retainer mechanism includes one or more clips operable to releasably hold the sheet-like implant against the first face of the leaf. For example, the sheet-like implant may be slidable into the clip and thus retained in the clip until released by the device.

Preferably the shaft and leaf, when in the cylindrical first position, are sized to fit through a trocar or cannula, such as an arthroscopic cannula with a bore with a diameter of about 1 cm. Further, the proximal end of the leaf may be configured to guide the unit into the cannula after deployment of the sheet-like implant. This configuration of the leaf may have ramped edges of the leaf configured to push the leaf into the cylindrical first configuration when the leaf is pushed or pulled into the bore of a cannula.

The leaf may further include one or more openings for accessing the sheet-like implant to secure the sheet-like implant to tissue or bone. For example, in some embodiments, the openings are sized for a tack, staple, or suture.

Aspects of the invention include methods for deploying a sheet-like material to a surgical repair site. For example, the method may include providing an implant delivery device that includes a handle, a shaft extending from the handle, a deformable plate attached to a distal portion of the shaft, such that the deformable plate comprises a first surface and a second surface obverse to the first surface. The device also includes a trigger on the handle and a retainer mechanism on the deformable plate. The trigger is operably linked to the deformable plate to pull the deformable plate between a cylindrical first configuration and a flat second configuration. The retainer mechanism is operable to releasably hold a sheet-like orthopedic implant against the first surface.

In embodiments of the method, when the device is ready, e.g., removed from its packaging, the deformable delivery plate is at rest, in the curled closed position. The method includes opening the deformable plate, by operating the trigger, thereby exposing the delivery surface and retainer mechanism (e.g., clip); positioning the implant (e.g., an approximately 2.5 cm square of collagen) on the surface; and relaxing the trigger, which de-tensions the wire extending through the shaft and around the head. The material of the deformable plate returns to its cylindrical conformation, curling the implant closed within the now-cylindrical deformable plate. With the implant loaded, the method may include inserting the closed plate with implant through a cannula in an incision in the shoulder of the patient; viewing the delivery plate on camera; and operating the trigger to open the delivery plate. Further, the method may include positioning the implant over and onto the repair site; attaching the implant to the repair site; and lifting the implant delivery device off of the implant. The device is curled back closed and withdrawn from the surgical site back through the cannula. Thus delivery methods preferably include, after loading a sheet-like implant onto the device, inserting the deformable plate in a cylindrical first position and a portion of the shaft into a body cavity to a surgical repair site and deploying the deformable plate to a second, substantially flat position such that the sheet-like implant material is in contact with the tissue. A separate device may be used to partially fix the sheet-like implant to tissue by accessing the tissue through an opening within the deformable plate. Further, the method may include removing the deformable plate, in some embodiments, by pushing the deformable plate forward to release the sheet-like material from the retaining mechanism. In some embodiments, the deformable plate and shaft are inserted or insertable through an incision, cannula and/or trocar. In some embodiments, the method includes returning the deformable plate to a first, cylindrical configuration for removal from the body cavity.

Aspects of the disclosure provide an implant delivery device that includes a handle; a shaft extending from the handle; a deformable plate carried on a distal portion of the shaft, the deformable plate comprising a first surface; a trigger on the handle, the trigger operably linked to the deformable plate to pull the deformable plate between a flat first configuration and a substantially cylindrical second configuration; an insertion sleeve positioned on the shaft and slidable on the shaft from a proximal end of the shaft to a distal end of the shaft such that the insertion sleeve covers the deformable plate when the deformable plate is in the substantially cylindrical second configuration; and a retainer mechanism on the deformable plate, the retainer mechanism operable to releasably hold a sheet-like implant against the first surface. The deformable plate may be connected to the shaft via a flexible section that allows the plate to be angled away from the shaft and aligned to tissue during surgery. The device may include a backbone attached to the shaft and extending from a proximal end of the deformable plate lengthwise in a center of the deformable plate toward a distal end of the deformable plate, wherein the backbone is attached to the distal end of the deformable plate via a slot such that the backbone is slidable in the slot in response to movement by the flexible section. The deformable plate may include a plurality of parallel channels that operate as a living hinge allowing the deformable plate to transition between the flat first configuration and the substantially cylindrical second configuration. In some embodiments, when the sheet-like implant is in the cylindrical second position, lateral ends of the sheet-like implant are curled inward. The deformable plate may have one or more openings through which a surgical fastener may be delivered through the sheet-like implant.

The device may include a wire extending from the trigger and through a loop channel within the deformable plate, such that tensioning the wire by the trigger pulls the deformable plate from the flat first configuration to the substantially cylindrical second configuration. The handle may include a latch operably connected to the trigger and to the wire and a lever spring operably connected to the trigger, wherein the latch is operable to releasably lock the deformable plate into a fixed position.

In some embodiments, the device includes a loading card that biases the retainer mechanism to an open shape, wherein the loading card is removably attached to the deformable plate. The loading card may have a loading pin positioned to hold the retainer mechanism open for positioning of the sheet-like implant upon the deformable plate while the loading card is attached to the deformable plate, wherein the loading card is configured to slide the loading pin from the retainer mechanism and release the loading card from the deformable plate while leaving the sheet-like implant retained upon the deformable plate.

In certain embodiments, the insertion sleeve is slidable on the shaft between back and front sleeve limiters. The insertion sleeve uncovers the deformable plate by sliding of the insertion sleeve backward in a direction proximal from the front sleeve limiter and covers the deformable plate by sliding of the insertion sleeve forward in a distal direction. The insertion sleeve may include a cap at the distal end, wherein, when the cap is pressed against an incision in tissue, the cap closes to form a cone-shape for insertion of the insertion sleeve through tissue. Once the insertion sleeve has passed through tissue, the cap preferably returns to an open position.

Aspects provide a method for tissue repair. The method may include providing an implant delivery device having a handle with a trigger, a shaft extending from the handle, a deformable plate attached to a distal portion of the shaft, the deformable plate comprising at least a first delivery surface with a retainer mechanism for holding a sheet-like implant against the delivery surface wherein when the deformable plate is at rest, the deformable plate is in a first flat configuration, and an insertion sleeve positioned on the shaft and slidable on the shaft from a proximal end of the shaft to a distal end of the shaft such that the insertion sleeve covers the deformable plate when the deformable plate is in a substantially cylindrical second configuration. In certain loading card embodiments, the device includes a loading card releasably attached to the deformable plate biasing the retainer mechanism into a receiving, or open, shape.

The method may include loading a sheet-like implant onto the deformable plate, e.g., by using a loading card to aid in positioning an implant onto the delivery surface to be held by the retaining mechanism and the removing the loading card from the deformable plate.

The method includes operating the trigger to move the deformable plate to the second substantially cylindrical configuration and preferably includes sliding the insertion sleeve toward the distal end of the shaft to cover the deformable plate. The method includes inserting the deformable plate and implant through an incision to a surgery site; sliding the insertion sleeve backward toward the proximal end of the shaft to thereby uncover the deformable plate;

deploying the deformable plate to the first flat position at the surgery site; positioning the implant on tissue at the surgery site; and attaching the implant to the repair site. Preferably, the method further includes removing the deformable plate from the implant and returning the deformable plate to the second substantially cylindrical position. If the embodiment uses an insertion sleeve, the method may include sliding the insertion sleeve to cover the deformable plate. Finally, the method may include withdrawing the deformable plate out of the surgical site back through the incision.

In the method, the implant delivery device may have any feature or combination of delivery device features disclosed elsewhere herein.

BRIEF DESCRIPTION OF THE DRAWINGS

FIG. 48 shows an insertion sleeve over the shaft.

FIG. 49 shows the insertion sleeve being slid over the shaft.

FIG. 71 shows a design with a bi-directional head.

FIG. 72 shows the bi-directional head in a cylindrical configuration.

DETAILED DESCRIPTION

The present invention provides devices and methods for deploying an implant to a surgical reconstructive or reparative site. Implant delivery devices of the invention, or "implant spreaders", have a delivery shaft extending from a handle, with a deformable member such as a plate or a leaf at a distal portion of the shaft with a surface carrying an implant for orthopedic surgery. A trigger or lever on the device positions the deformable member between a first cylindrical configuration that can pass through an incision or through a cannula used in arthroscopic surgery and a second, substantially flat configuration useful to place the implant on tissue during the arthroscopic surgery. Preferably the trigger may be operated to hold the deformable plate or leaf in any of a continuum of positions between the first cylindrical configuration and the second, substantially flat configuration. The deformable plate or leaf preferably includes a plurality of parallel hinges, e.g., living hinges, promoting its deformability between the first cylindrical configuration and the second, substantially flat configuration. A plastic nature of the material may bias the deformable plate or leaf into the first cylindrical configuration when at rest, i.e., unstressed, while a tension wire or tension member may be operated to temporarily strain the deformable plate or leaf into the second, substantially flat configuration (or vice-versa; the deformable plate or leaf may occupy the second, substantially flat configuration at rest and may, under tension, be temporarily deformed into the first cylindrical configuration). Particularly, the invention provides for sterile, single-use devices designed to address the technical difficulties of implant deployment and positioning. Devices of the invention allow for delivering and positioning an implant (e.g. graft, patch, scaffold) to repair tissue defects and tears with greater accuracy resulting in improved outcomes for reparative and reconstructive surgeries.

Devices of the invention may be sized to insert the implant material through an incision during a minimally invasive procedure such as arthroscopic surgery. For example, devices of the invention allow for insertion, deployment, and positioning of an implant into a body cavity using arthroscopic or laparoscopic techniques, or through a small incision. In some embodiments, the invention provides a device and method for graft implantation on top of a torn rotator cuff or other joint during arthroscopic joint repair. In this way, the implant provides structural support and induces the formation of new tendinous tissue over the surface of the tendon, resulting in a repaired or thicker tendon. Thus, the invention provides for accurately positioning the implant material in a desired placement at the surgical repair site for fixation.

Figure 1:
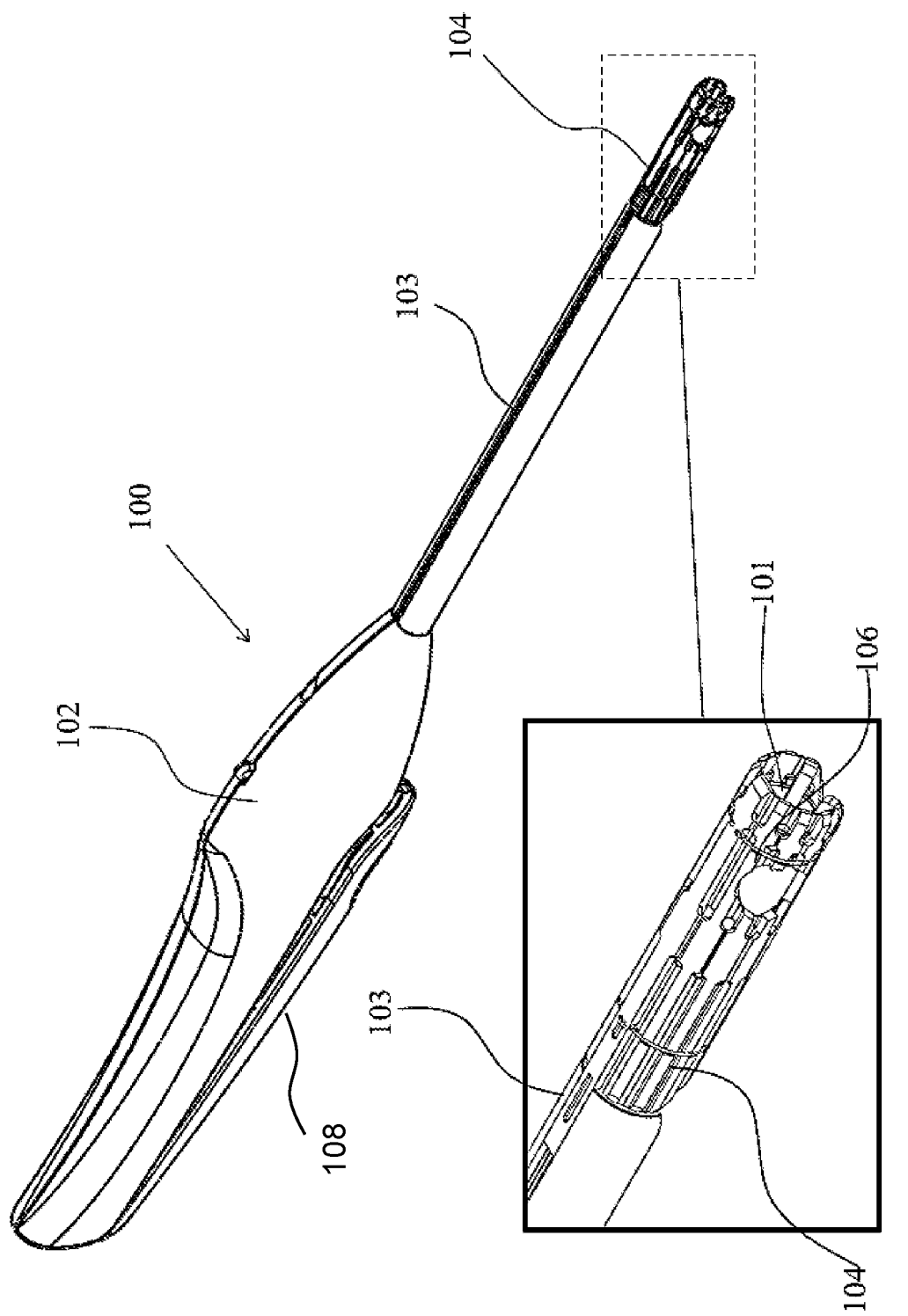
FIG. 1 shows an implant delivery device.

FIG. 1 illustrates a perspective view of an embodiment of an implant delivery device of the invention. The device 100 may be adapted for insertion and deployment of a sheet-like implant 101 material, such as an orthopedic tissue graft, into a body cavity during minimally invasive surgery. The device 101 may comprise a handle 102, an elongated shaft 103 and a deployment plate 104 connected to the distal end of the shaft 103 for deploying and positioning the implant 101 material to the surgical repair site.

Aspects of the invention provide an implant delivery device 100 with a handle 102 and a shaft 103 extending from the handle. At the distal end of the shaft 103, the device may include a deformable plate 104 as the deployment support.

The deformable plate 104 may include a first surface and a second surface obverse to the first surface. The handle 102 may include a trigger 108 operably linked to the deformable plate 104 to pull the deformable plate between a cylindrical first configuration and a flat second configuration. A retainer mechanism 105 may be included as part of the deformable plate 104. The retainer mechanism may be operable to hold a sheet-like implant 101 material against the first surface. The sheet-like implant may be an orthopedic implant.

In certain embodiments, the deformable plate assumes the cylindrical first configuration at rest and the trigger pulls the plate to the flat second configuration. In such embodiments, the deformable plate optionally includes (has within the plastic material) a spring, e.g., a metal spring, such as a C-shaped spring built into, or within, the deformable plate, in which the C-shaped spring biases the deformable plate into the cylindrical first configuration. In other embodiments, the deformable plate assumes the flat second configuration at rest and the trigger pulls the plate to the cylindrical first configuration. In flat-at-rest embodiments, the plate may include a spring (e.g., a flat piece of metal or other material that is biased to return to flat when deformed away from flat).

Importantly, the deformable plate 104 may be positioned into at least two configurations. As shown in the inset of FIG. 1, the plate 104 may be substantially cylindrically shaped, i.e. a furled configuration, in which the deformable plate 104 is formed as a tube, along the length of the plate, with the graft or implant 101 material retained along the inside wall, i.e. first surface. The graft may be rolled or may be in a substantially cylindrical shape by virtue of being retained on the first surface of the plate. This configuration allows insertion of the deformable plate 104 and the graft 101 into a body cavity through a small incision or a cannula, while protecting the implant material retained upon the plate.

The implant delivery devices of the invention support many configurations, mechanisms, and/or supports for delivering a sheet-like material to a surgical repair site, such that the material is carried to the surgical repair site in a substantially cylindrical or rolled position. The support may be any shape having a thin, flat surface. For example, the support may be defined as a deformable plate or leaf, being wide and thin and having a flat surface, and being attached to the shaft and handle at one edge or end. In non-limiting examples describe herein, the support is defined as a plate 104, for example a deformable plate or deployment plate.

Figure 2:
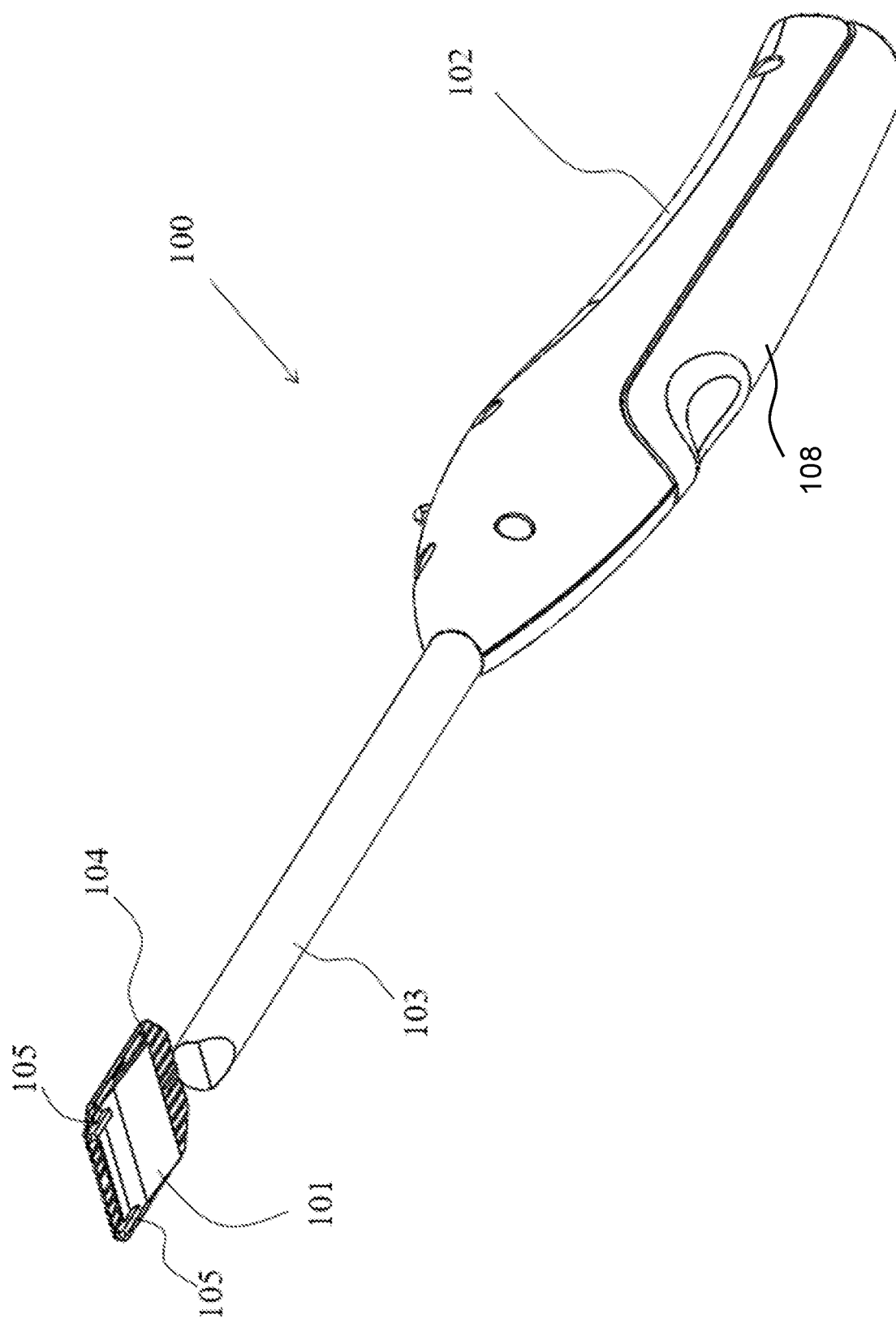
FIG. 2 shows the device in a deployed, flat configuration.

FIG. 2 illustrates one embodiment of the device 100 in which the deformable plate 104 is in a deployed configuration. The second configuration may be substantially flat as illustrated, or any position ranging from substantially cylindrical to substantially flat. For example, in a deployed substantially flat position, the device allows for attaching the implant material 101 to the device 100 outside the body before insertion, deployment, and positioning of the graft at the target tissue. In embodiments, a deployed configuration of the deformable plate is referred to as an open position, while a substantially cylindrical position is referred to as a closed position.

The plate may be connected to the shaft via a flexible section (e.g., a hinge or UV joint along the shaft) that allows the plate to be angled away from the shaft and aligned to tissue during surgery. Such a flexible section allows an angled approach to the tissue while the surgeon can substantially align the plate to the tissue surface by pressing it against the tissue.

As is described in more detail below, the implant 101 material may be releasably retained on the device using a retainer mechanism 105 on the plate 104. The deformable plate 104 may be flexibly attached to the shaft 103 of the device 100 to allow for flexibly placing the implant 101 material onto tissue. In other embodiments, the deformable plate may be rigidly attached to the shaft. The shaft may include a beveled edge at the distal end of the shaft to aid in pulling or pushing the device through an incision or cannula.

Once the implant 101 material is retained within the retainer mechanism 105 on the deformable plate 104 of the device, the device may be returned to the cylindrical or furled position for insertion into a body cavity. After the deformable plate 104 is inserted through an incision or cannula, it may be moved from the cylindrical configuration to a flat configuration by actuation of a trigger 108 on the handle 102 of the device 101. After insertion, the implant 101 material, such as a graft, may be placed on top of a target tissue, where a separate device may be used to attach the graft to the tissue.

Once at least partial attachment of the implant to tissue has been achieved, the deployment plate 104 attached to the shaft 103 of the device 100 is removed from the graft 101, and configured into a furled or cylindrical position for removal from the patient. The handle may be adapted to allow a surgeon to actively transform the deformable plate 104 between a substantially cylindrical or furled position and a deployed, i.e. flat position.

The deformable plate 104 may include at least one opening 106 which, upon deployment of the graft to tissue, may be used to access the graft for attachment of the graft to the tissue by a separate attachment device. For example, the opening 106 may be a circular, rectangular, or other shape to allow for attachment of the implant via a staple, tack, or suture. The opening may be a slit or cut-out shaped for access to the implant by a specialized attachment device. In this way, devices of the invention facilitate attachment of an implant to tissue.

Figure 3:
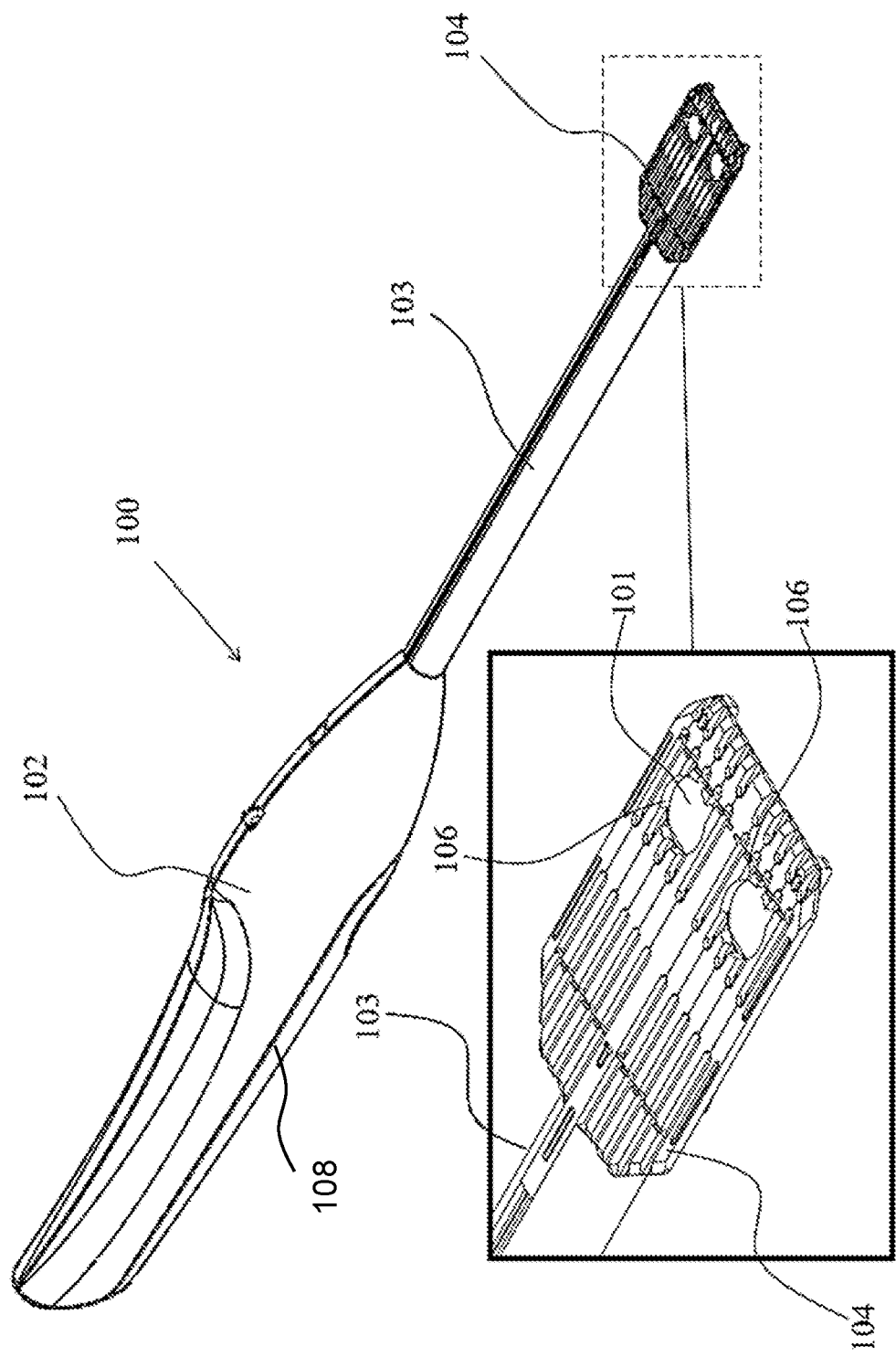
FIG. 3 shows living hinges on a deformable plate or leaf.

FIG. 3 illustrates an embodiment of a deformable plate 104 in a deployed, flat configuration. In some embodiments, the plate 104 may be made of a plastic that is shaped or molded. The plate 104 may be made of a flexible material, for example a flexible polymer such as polyoxymethylene (POM) or acetal, or polypropylene. The plate may be pre-formed into a furled or cylindrical configuration, for example by using an injection molding, 3D-printing, or computerized manufacturing processes (CNC) technique known to persons skilled in the art. The plate may be further prepared and shaped into a preformed cylindrical shape using a plastic annealing process. Thus, the plate may be elastically biased into a substantially cylindrical position as a result of the material used, and the manufacturing and/or annealing process.

The plate may be pre-shaped to collapse into a cylindrical shape or to be elastically biased into a cylindrical shape. The plate may be made of a shape-memory polymer, for example, a thermoplastic and/or thermoset (covalently cross-linked) polymeric material. The plate may be formed as a single piece or as several pieces assembled and connected so as to retain a cylindrical configuration. As described in detail below, in some embodiments, the plate may be retained in a substantially cylindrical position via as its rest or default position, but deformable via hinges and/or springs. Importantly, plan view of the deformable plate may be any shape, for example a rectangular, oval, square, leaf-like, or circular shape. In embodiments, in plan view, the deformable plate is polygonal, for example an octagon.

Figure 4:
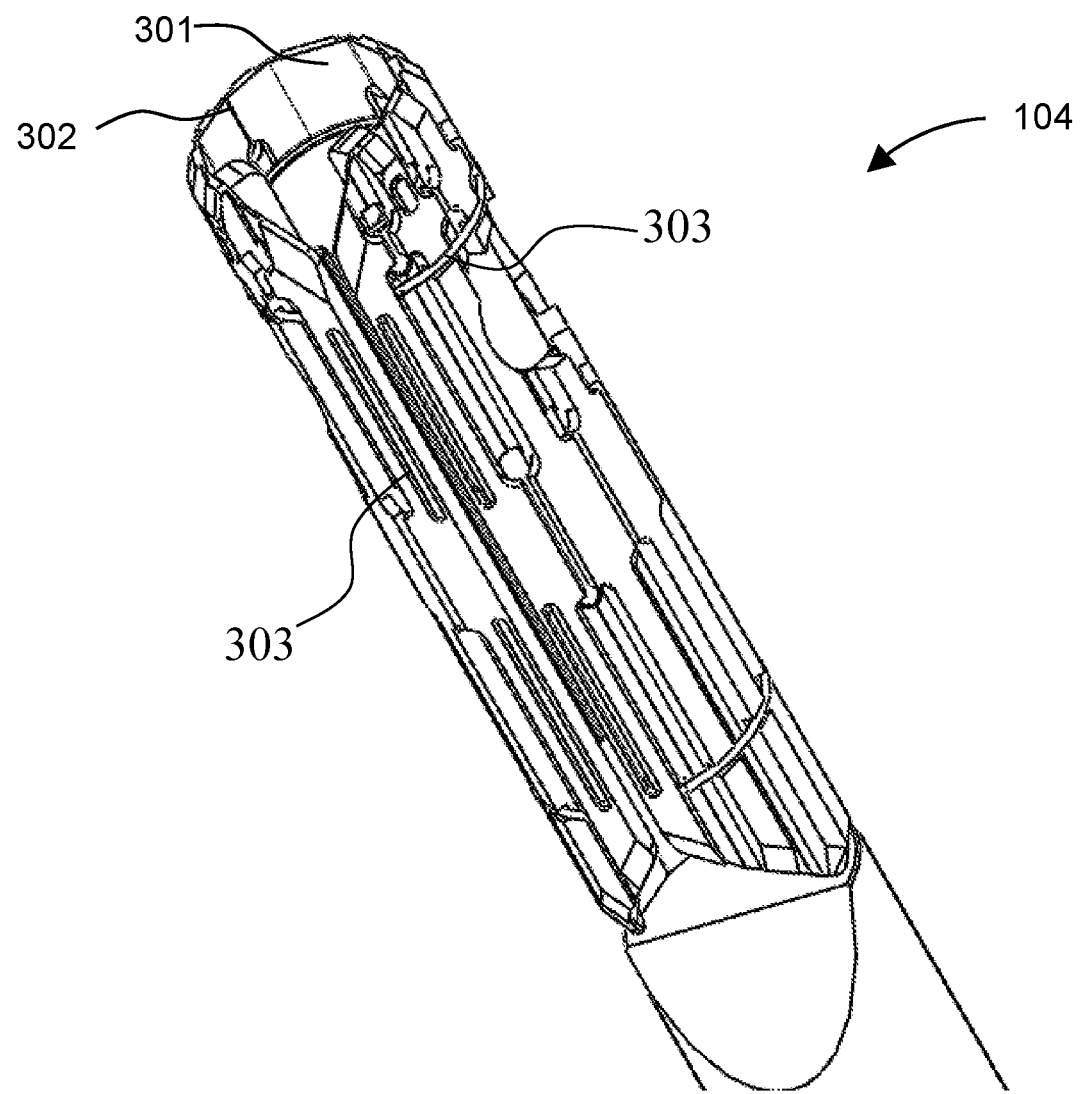
FIG. 4 shows the deformable plate or leaf in a cylindrical first configuration.

FIG. 4 illustrates an embodiment of the device in which the deformable plate 104 is in a cylindrical first configuration. In some embodiments, the first surface of the deformable plate may be a single, monolithic piece of material. Thus, the first surface may be a flat surface upon which an implant material may be retained. The deformable plate may include a plurality of channels or sections in the second surface that operate as a living hinge allowing the deformable plate to be pulled from the cylindrical first configuration to the flat second configuration.

As noted, the cylindrical first configuration may also be referred to as a closed or furled position such that an implant retained upon the plate is neatly and securely retained within the inner confines of the configuration.

In some embodiments, the deformable plate 104 comprises a series of long, rigid, or semi-rigid sections 301 connected via a series of hinges 302 located near the inner portion of the plate 104. The ridges may be a plurality of parallel channels in the second surface running lengthwise on the plate from a proximal end to a distal end, or spaces in between. The plurality of channels may be described as slots running lengthwise on the deformable plate from a proximal end to a distal end. For example, the ridges and/or channels may be formed on the second surface as part of the molding process. In some embodiments, the deformable plate includes one or more hinges, each hinge having a hinge axis parallel to an axis of the cylindrically-shaped first position.

In some embodiments, the hinges are living hinges, i.e. thin and flexible sections of the material adapted to be deformed during operation of the device. The living hinge 302 may be a thin piece of plastic surrounded by the thicker plastic of the ridges 301 that allow the plate 104 to bend at the sections from 1 degree to 180 degrees. The hinges may be located on the first surface of the plate to allow the plate to move from a substantially cylindrical first configuration to a substantially flat second configuration. The living hinges may be formed by cutting or scoring the deformable plate on the second surface between the ridges or slots, or on the top of the channels.

In some embodiments, the deformable plate includes a plurality of separate rigid or semi-rigid sections coupled together via a hinge material. The hinge material may be a plastic or metal hinge actuated by spring mechanism. Each hinge may be living hinge provided by one continuous piece of material for the plate or leaf, with a channel or groove that imparts flexibility.

Figure 5:
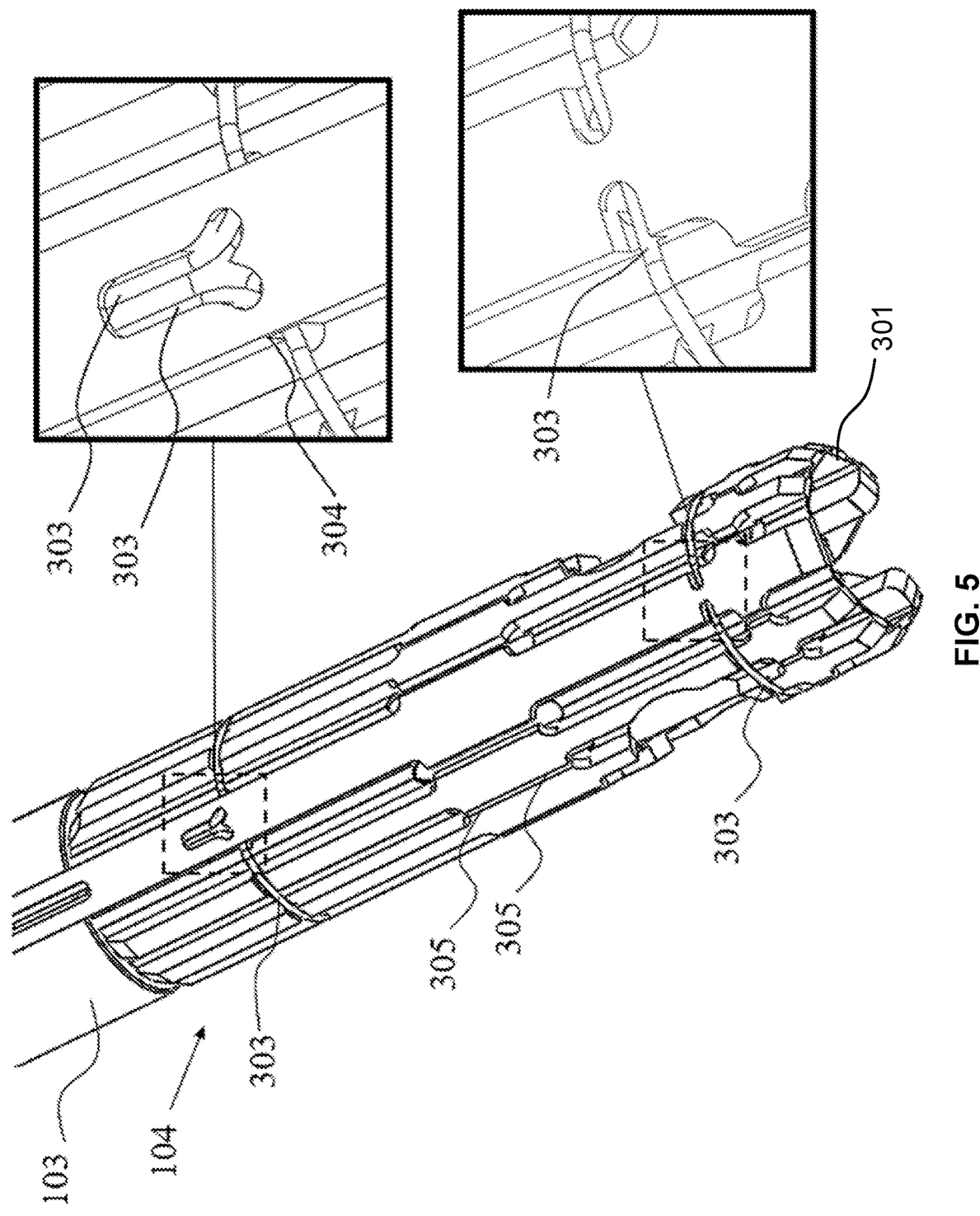
FIG. 5 shows positioning of a wire in the deformable plate or leaf.

FIG. 5 illustrates one embodiment of a deployment plate 104 of the invention in which the plate is in a cylindrical first configuration. In some embodiments, the device 100 includes a deployment wire 303 or thread extending from the trigger 108 and through a loop channel 304 within the deformable plate 104, such that tensioning the wire by the trigger 108 pulls the deformable plate 104 from a cylindrical first position to the flat second position. The wire may be, for example, any wire, thread, or line capable of retaining tension such that the wire pulls the plate from a cylindrical first position to a substantially flat second position. In certain embodiments, the wire is a multifilament wire. Use of a multifilament wire promotes better deformability and reduces resistance when the wire slides within the channel. Preferably, the loop channel is at least partially covered to retain the wire therein. I.e., the wire is passing through the channel at the plate, and the channel in partially covered in order to prevent the wire sliding out of it.

In some embodiments, the deployment plate 104 may include one or more deployment wire channels 304 passing from the center of the plate 104 from the shaft 103 to the perimeter of the plate 104, to the distal end of the plate, and back to the shaft 103. One or more deployment wires 303 may be housed within the deployment channel 304. In embodiments, the wire 303 may be house on the outer perimeter of the deployment plate 104 within a deployment channel 304. In embodiments, the deployment wire is house within one continuous channel.

The deployment wire/wires 303 may further be extended through the shaft 103 toward the handle where the wire 303 may be operably connected to the trigger 108 of the device. For example when the trigger 108 is pressed, tension may be applied to the wire 304 such that the wire pulls the sections 301 of the deformable plate 104 from a cylindrical position to a desired second position. Thus, the deployment wire(s) 303 provides and controls the tension at the channel 304 to deploy the deployment plate 104 from the cylindrical first position to a substantially flat position.

In some embodiments, a wire may extend from the trigger, through the shaft, and through a channel adjacent to the second face of the plate, such that squeezing the trigger pulls the wire in a proximal direction along the shaft, deforming the plate from the cylindrical first configuration to the flat second configuration.

In some embodiments, the trigger may be moved to, and held in, a plurality of different positions between a rest position, i.e. a closed, furled, or cylindrical position, and a fully-pulled position. For example, a rest position may be one in which there may be no or limited tension applied to the deployment wire. A fully-pulled position may be a position in which a maximum amount of tension is applied to the deployment wire. In some embodiments, the trigger is configured to lock the deployment plate into any number of positions by a locking mechanism operably coupled to the trigger and the deployment wire.

For example, the plate may be locked into the cylindrical position, a position in-between cylindrical and flat, or in a substantially flat position. The locking mechanism may lock the tension applied to the deployment wire in a rest or fully-pulled position, or any position in-between. Specifically, in some embodiments, the deformable plate may be held, by one-handed operation of the trigger in any position along a continuum between a cylindrical first configuration and a flat second configuration. In this way, one-handed operation of the device leaves a free hand for a surgeon to operate a separate second device, such as a device for fixing the implant material to tissue.

Figure 6:
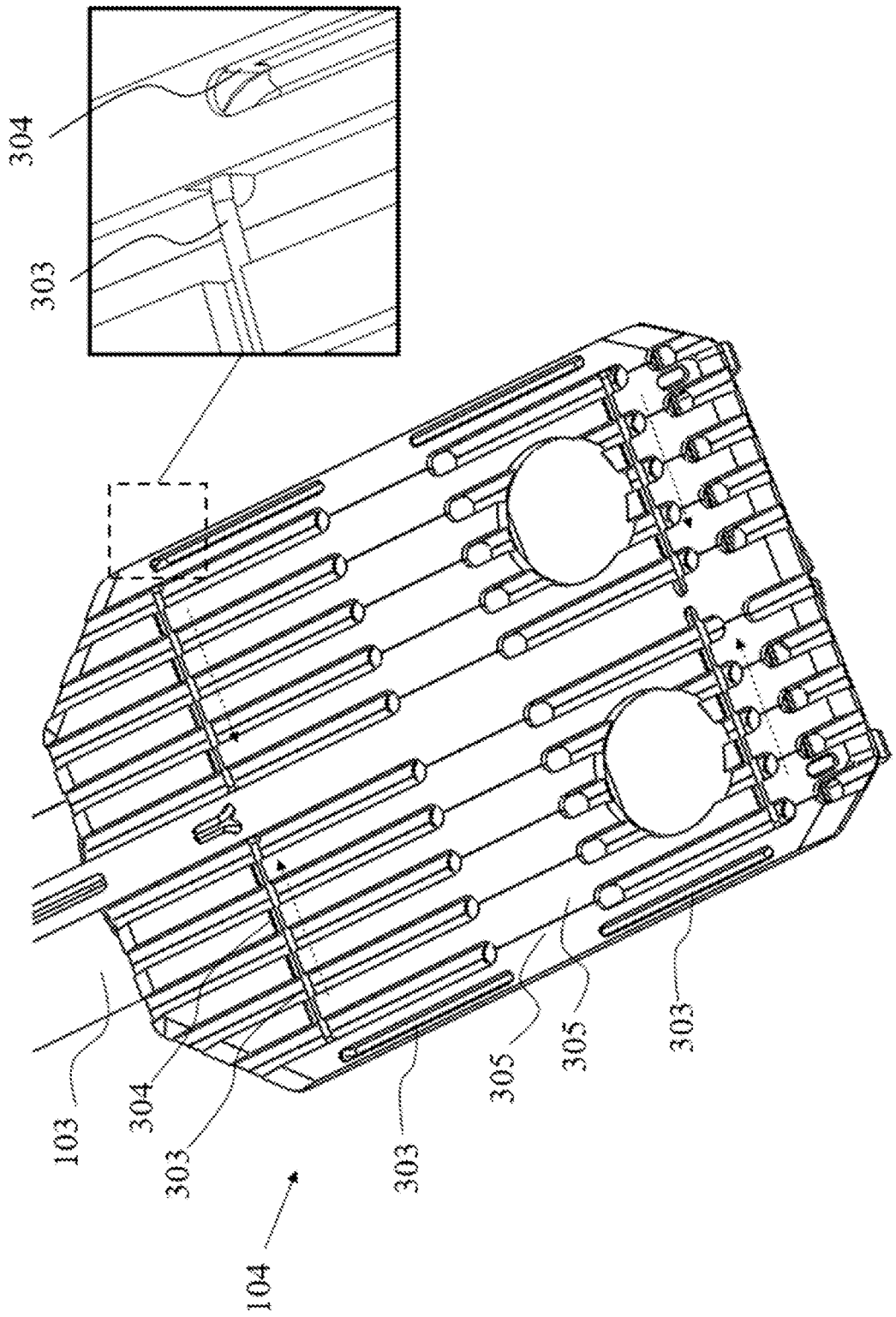
FIG. 6 shows the wire housed within a wire channel.

FIG. 6 illustrates an embodiment of the deformable plate 104 in a flat position and illustrates the deployment wire channel 304 passing from the center proximal end of the deformable plate 104 around the perimeter of the plate with the wire 303 housed within the wire channel 304.

Notably, the deployment plate 104 may include a series of limiters 305 to prevent the sections 301 from rotating beyond a flat angle. For example, the second surface may include extensions that overhang the channels such that when the deformable plate is pulled to the flat second configuration, the extensions prevent the deformable plate from deploying past about 180 degrees. Thus, although the deformation of the deformable plate may encompass a range of configurations between substantially cylindrical and substantially flat, a configuration past a 180-degree flat position may be prevented by the limiter. Limiters may be included to prevent collapse. If one hinge were to go over and beyond a flat angle, that hinge could continue rotating even while any other hinge(s) stop, which could destabilize or collapse the configuration of the plate. The limiters stabilize the plate against such a collapse.

In embodiments, the limiters may be small pieces of material located on the second surface, for example above the hinges located on the first surface. The limiters may act as a stop or obstruction to limit the opening of the plate past a flat configuration and/or collapsing past a flat configuration. Thus, when tension is applied to the deployment wire, the limiters may come in contact with each other to prevent the plate from opening or deploying past about 180 degrees.

In embodiments, the limiters may be projections, segments, or stops integrally formed as part of the second surface. The limiters may be projections, segments, or stops added to the second surface to prevent opening or deployment of the plate past a pre-determined deployment, e.g., about 180 degrees. The limiter may be one piece formed at manufacture, for example via injection molding, or may be cut or milled to form a living hinge on the first surface of the plate with the limiter on the second surface of the plate between the ridges.

In embodiments, the limiter may include a first edge and a second edge associated with a hinge such that when the plate is deformed in a flat position the first and second edges are in contact to prevent the plate from deploying past e.g., 180 degrees.

Figure 7:
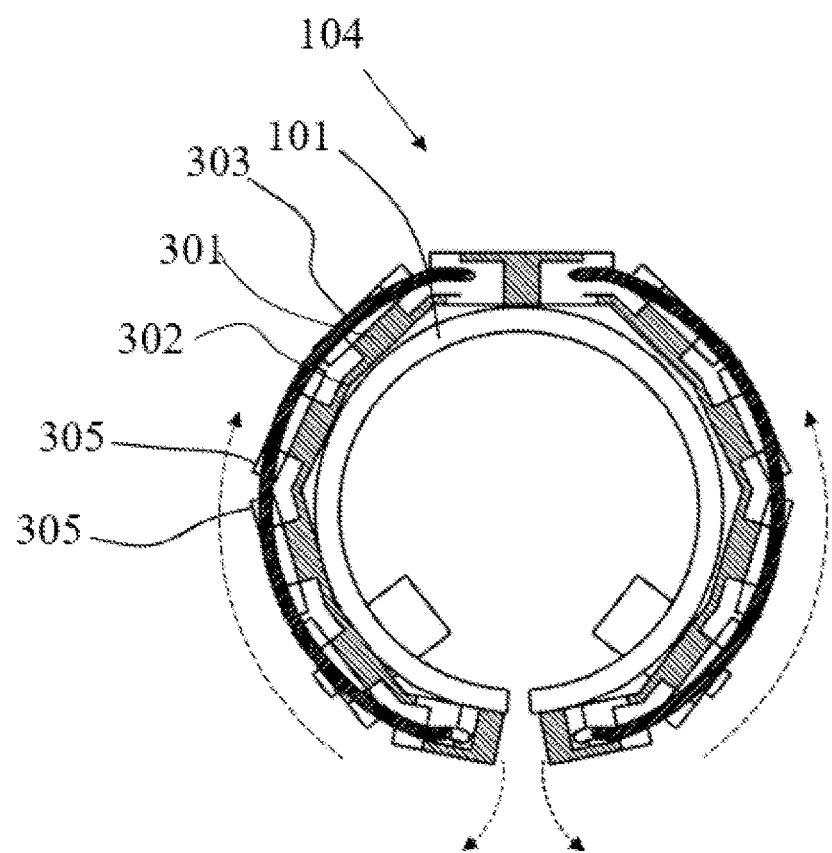
FIG. 7 is a cross-section of the deformable plate or leaf in the cylindrical position.

FIG. 7 illustrates a cross-sectional view of an embodiment of the deployment plate in the cylindrical position. The channels formed between the sections 301 may be in an open position, operable by the flexibility of the living hinge 302. In some embodiments, the flexibility of the material from which the deployment plate is made, for example a flexible plastic, may act as a spring to retain the cylindrical configuration. In other embodiments, the device includes a spring to hold the deployment plate in a closed, substantially cylindrical configuration.

The deployment wire 303 may be located above the hinges 302 such that once tension is applied to the deployment wire 303 each one of the sections 301 is rotated upward in relation to the hinges 303 and the deployment plate is transformed into a flat configuration. Notably, the implant 101 material is retained on the first surface of the device within the interior of the cylindrical shape. In this way, the material is protected from tearing or damage during insertion, positioning, and deployment to the repair site.

Figure 8:
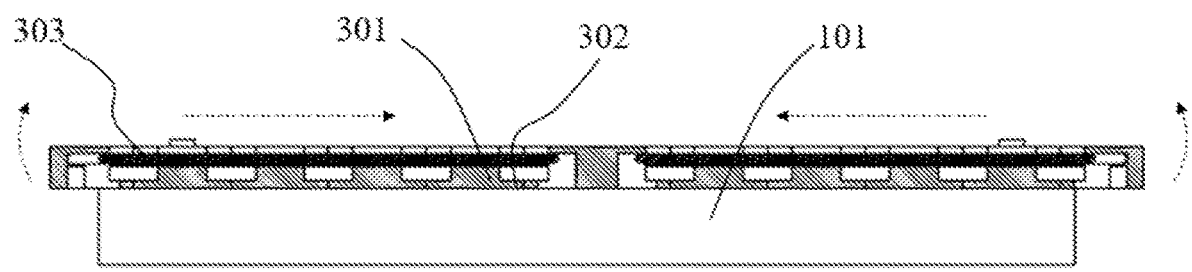
FIG. 8 is a cross-section of the deformable plate or leaf a flat position.

FIG. 8 illustrates a cross-sectional view of the deployment plate 104 with tension exerted on the deployment wire 303 to open the deployment plate 104 from a cylindrical position first position to a flat position. As is described in more detail below, tension is exerted on the wire 303 via a trigger mechanism housed within the handle. Thus the trigger 108 and deployment wire 303 are operably connected wherein actuation of the trigger exerts the tension on the wire necessary to transition the deployment plate from a cylindrical or furled first position to a substantially flat or unfurled position.

Figure 9:
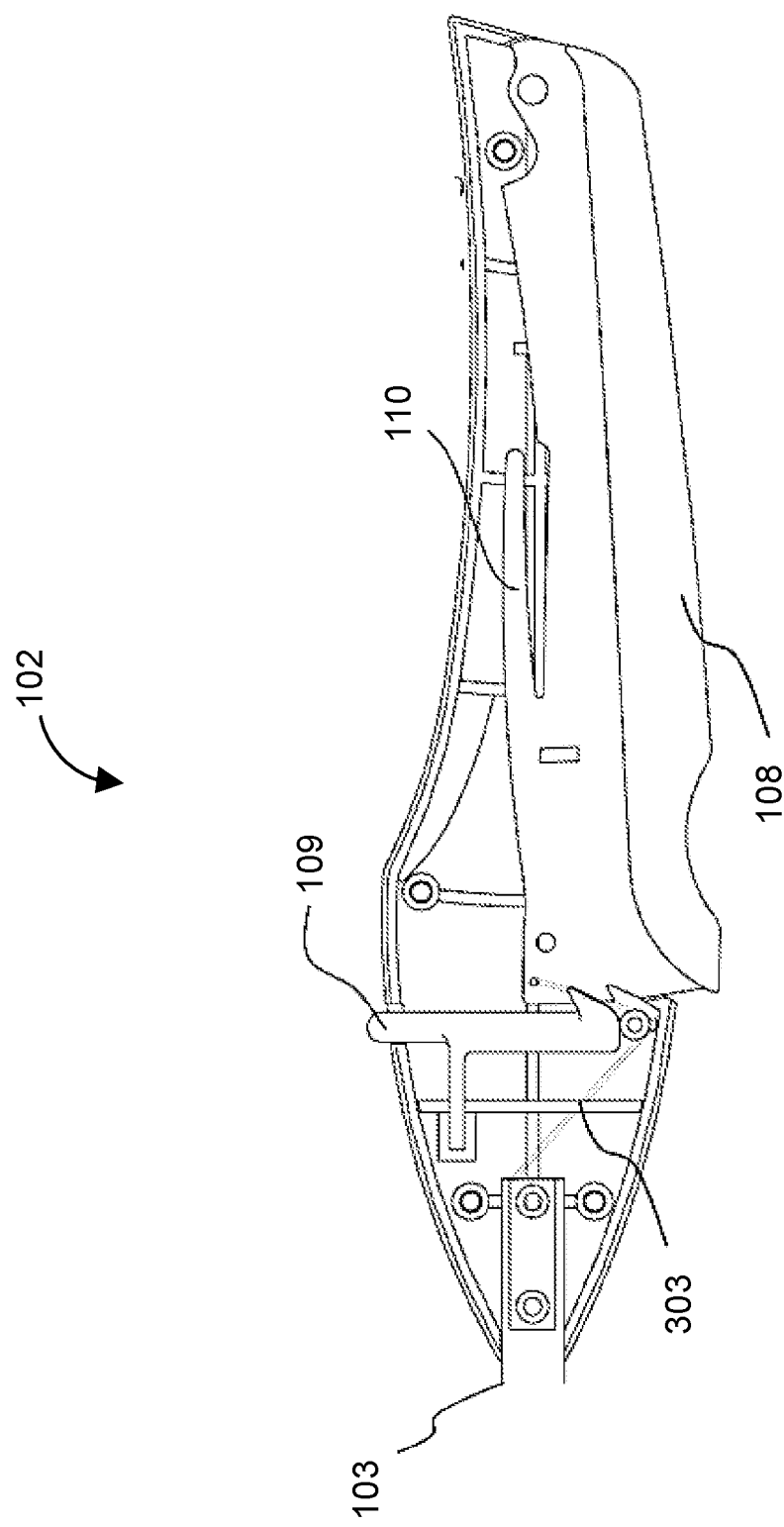
FIG. 9 shows components in the handle.

FIG. 9 shows the handle 102 of a device 100. The handle 102 may be connected to a proximal end of a shaft 103. The handle may include a trigger 108 or lever operably connected to the deployment wire 303. In embodiments, the handle may also include a latch 109 operably connected to the trigger 108 or lever and to the deployment wire 303, such that the latch is operable to releasably lock the deformable plate into a fixed position. The lever can be released by a surgeon once it has been locked. The fixed position may be a substantially cylindrical position, a substantially flat position, and/or any position between cylindrical and flat.

The device may also include a lever spring 110 operably connected to the trigger 108 to facilitate actuation of the trigger. For example, pressing the trigger may compress the lever spring such that the latch locks (or unlocks) the trigger into a fixed position. With the trigger locked into a fixed position, the tension upon the deployment wire may remain fixed thus locking the deployment plate into a fixed configuration. The latch may be released by pressing the trigger again. The lever spring may facilitate the return of the trigger to a rest position in which the tension on the deployment wire is minimal as illustrated in FIG. 9.

In some embodiments, when the trigger is activated, for example, the trigger is pressed, the spring may open and the deployment wire attached to the trigger is pulled back such that tension for deployment of the deployment plate from the cylindrical position is created. In other embodiments, the spring is separate from the trigger or lever.

Figure 10:
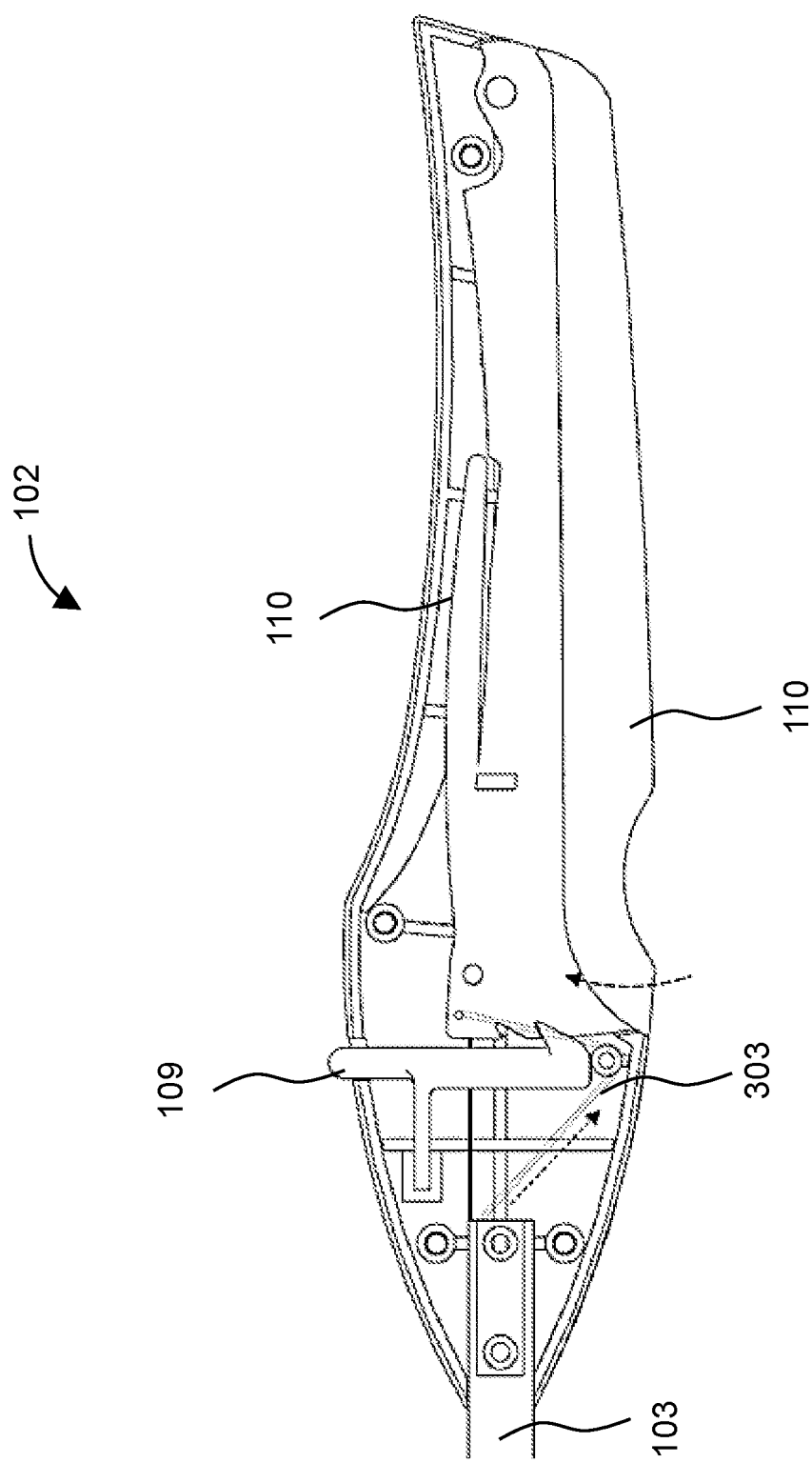
FIG. 10 illustrates wire travel in the handle.

FIG. 10 shows a sectional view of a side of one embodiment of the handle 102 with the trigger pressed in an upward direction toward the body of the handle in order to actuate pulling the deployment wire 303 to apply tension to the wire. The trigger 108 may be pressed towards the body of the handle 102 such that tension is applied to the deployment wire 303. In some embodiments, this tension causes the deployment wire 303 to pull the deployment plate 104 from a cylindrical position, i.e. a rest or un-tensioned position, to an open position (or vice-versa). The degree to which the trigger is pressed may actuate the degree to which tension is applied to the deployment wire.

Additionally and/or alternatively, embodiments of the device may include a ratchet mechanism to allow for the flexible opening and closing of the deployment plate. For example, the ratchet mechanism may allow the user to move the deployment plate from a substantially cylindrical position, i.e. closed or furled, then open or unfurl, and then hold/lock, the deployment plate in any number of positions for suitable placement of the deployment plate onto tissue. For example, the ratchet may include a spring loaded pawl on saw teeth, flexible metal sheet sliding over cam or saw teeth, or other ratchet mechanisms known to those skilled in the art.

Figure 11:
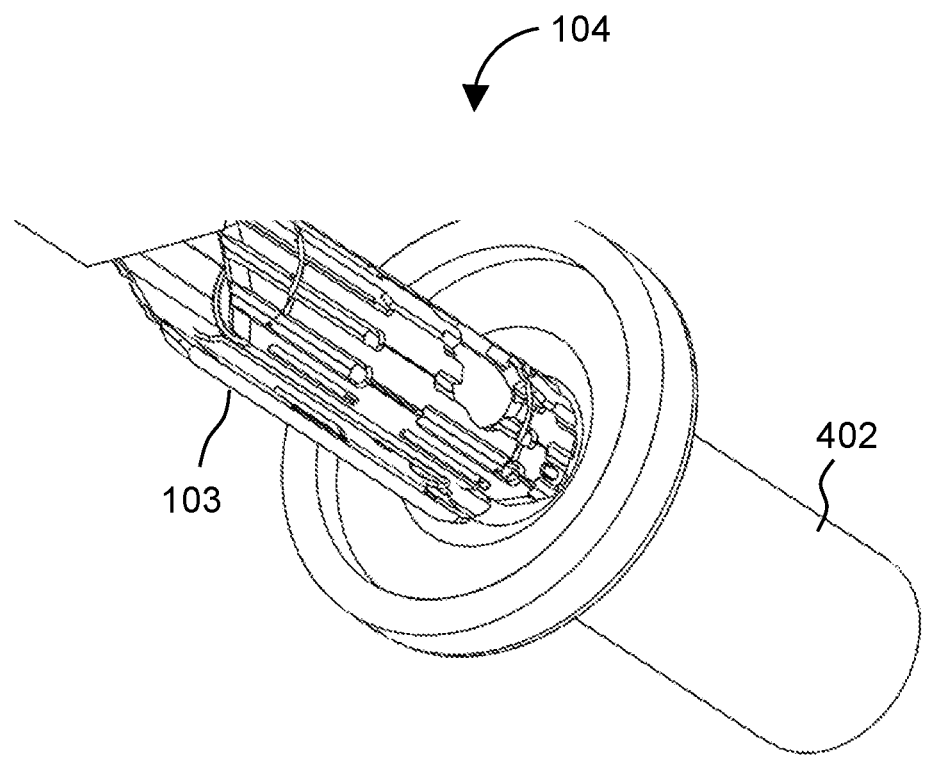
FIG. 11 shows the deformable plate or leaf entering a cannula.

FIG. 11 illustrates one embodiment of the device in which the deployment plate 104 is in a cylindrical position for insertion into a trocar and/or cannula 402. The device may be designed such that the deformable plate is sized to be delivered to a joint or cavity inside the body via a port or incision. For example, in some embodiments, the device is sized such that when the deformable plate 104 is in a cylindrical first configuration, the deformable plate may be inserted through a cannula 402 used in arthroscopic keyhole surgery. Devices of the invention may also be sized and configured for laparoscopic surgery performed through an opening in the abdominal wall or other parts of the body. For example, the shaft and deformable plate, when in a cylindrical first configuration, may be sized to fit in a trocar, cannula, and/or incision. In specific embodiments, the shaft and the deformable plate, when in the cylindrical first position, are sized to fit through a trocar.

Figure 12:
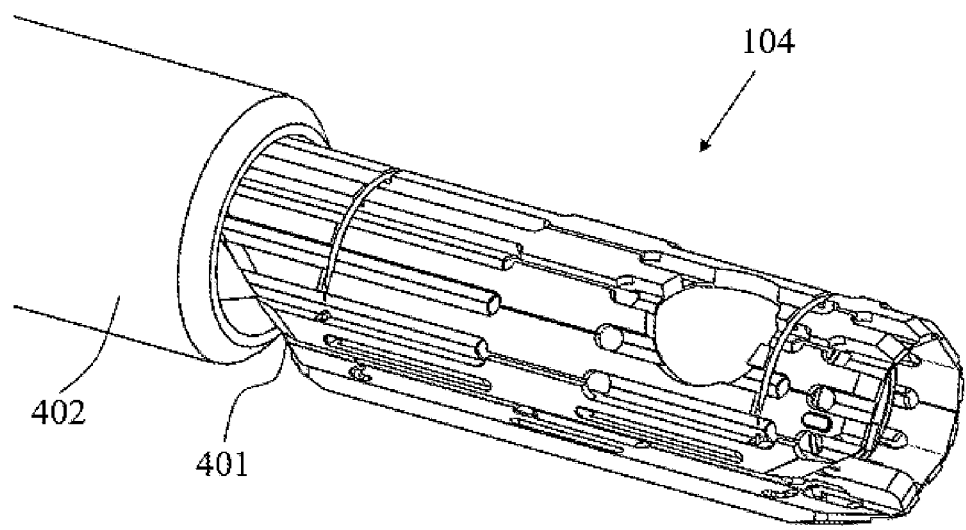
FIG. 12 shows the deformable plate or leaf exiting a cannula near a surgical site.

FIG. 12 illustrates the deployment plate as pushed through the end of a cannula 402 in a body cavity toward the tissue surface. The proximal end of the deformable plate may further be configured to guide the deformable plate back into a trocar or cannula after deployment of the sheet-like implant. For example, in some embodiments, the deformable plate 104 may have ramped or angled edges 401 that bias the deformable plate into the cylindrical first configuration when the deformable plate is pushed or pulled into the bore of a trocar or cannula while the deformable plate is not fully in the cylindrical first position. For example, the deformable plate may be shaped as a rectangle in which one or more corner edges 401 are angled.

In some embodiments, the proximal end of the deployment plate 104 includes one or more sloped edges 401 on the end to help feed the deployment plate back into the cannula 402, trocar, or incision after deployment such that the device may be removed from a body cavity. For example, after deployment of the implant, the deployment plate 104 is returned to a first cylindrical position. In this position, one or more angled, sloped, or beveled edges 401 at the proximal end, i.e. the end connected to the shaft, help feed the deployment plate 104 in the cylindrical shape back into the cannula for removal from the cannula. Thus, if the deployment plate is in a slightly open position from the cylindrical configuration after deployment of the implant material, when the sloped edges of the deployment plate come in contact with the end of the cannula, the sloped edges close the plate into a cylindrical configuration to fit within the cannula.

In embodiments, the angled edges of the proximal end of the deployment plate align with an angled edge of the distal end of the shaft to help feed the shaft and deployment plate back through the cannula or incision.

Figure 13:
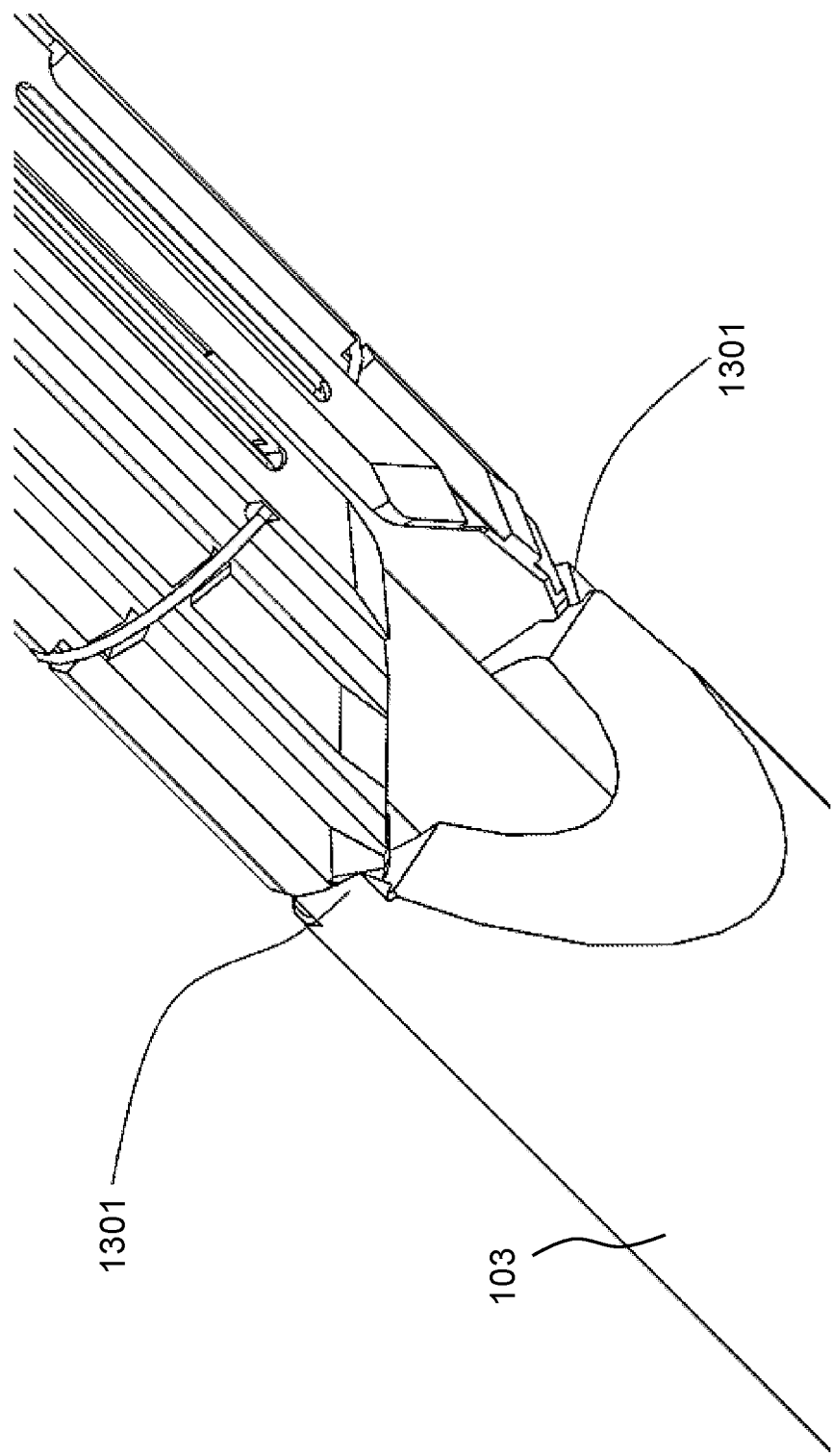
FIG. 13 shows insertion limiters.

FIG. 13 illustrates one embodiment of a shaft 103 of the device in which the shaft includes at least one insertion limiter 1301. When the deployment plate is pushed through a cannula or opening, a force may be applied to facilitate positioning the deployment plate and shaft through the opening and to the deployment site. To prevent an application of force from deforming the deployment plate the insertion limiter 1301 acts as a stop or obstruction to keep the deployment plate in a closed or cylindrical configuration as it is pushed through an opening or cannula. In some embodiments, the insertion limiter may be a beveled edge or cut-out on the distal end of the shaft.

Figure 14:
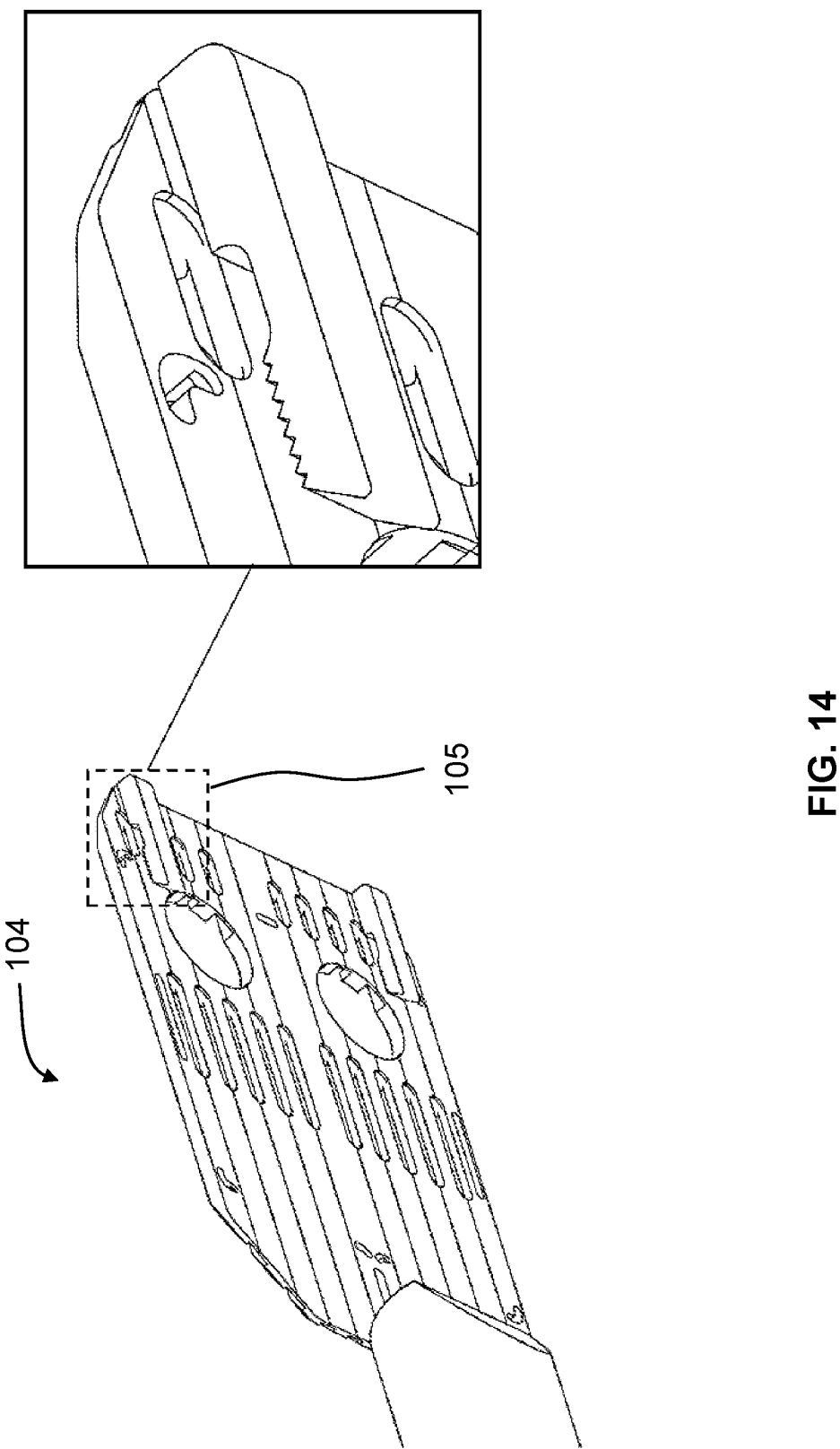
FIG. 14. shows a retaining mechanism to hold an implant on the deformable plate or leaf.

FIG. 14 shows a retaining mechanism on the first surface of the deployment plate where the implant material will be held. The retaining mechanism 105 may be one or more clips 501 adapted to enable a reversible connection of the implant material to the deployment plate 104. In some embodiments, at least one and preferably two holding clips 501 are adapted to enable a reversible connection of a graft 101 to the deployment plate 104. For example, the clip may include a prong with teeth or a teeth-like surface on the underside of the prong with which to lightly grip the implant material and secure the implant material to the first surface of the deployment plate 104.

The clip(s) may be optionally opened by an operator to allow the user to more easily slide an implant or graft onto the plate, into position. For example, the clip(s) may include a lever whereby pressing the lever actuates the prong to open up such that the implant material may be placed underneath the prong. Releasing the lever may cause the clip teeth to close onto the implant material to retain the implant material on the deployment plate. Thus, the action necessary for gripping the implant material and retaining the implant material upon the deployment plate may be actuated.

In other embodiments, the retaining mechanism may be a slot configured to hold the implant material by sliding the implant material into the slot.

In some embodiments, the retaining mechanism may be one or more tabs attached to deployment plate at the first surface. For example, the tabs may be flexibly secured to the deployment plate such that the tabs may rotate to an open position away from the plate and rotate to a closed position to hold the implant material onto the plate. In specific embodiments, the tabs may be rotatable to open allow for placement of the implant material onto the deployment plate and rotatable to close upon and retain the implant material after placement.

The retaining mechanism may be molded from the same piece of material as the deployment plate, for example, as part of a single, monolithic piece of material. Additionally and/or alternatively, the retaining mechanism may be made from a different material or a separate mold that is glued to the deployment plate or heat stacked.

In embodiments, the implant material may be released from the retaining mechanism by action of pushing the deployment plate forward such that the retaining mechanism opens and the implant material is released.

Figure 15:
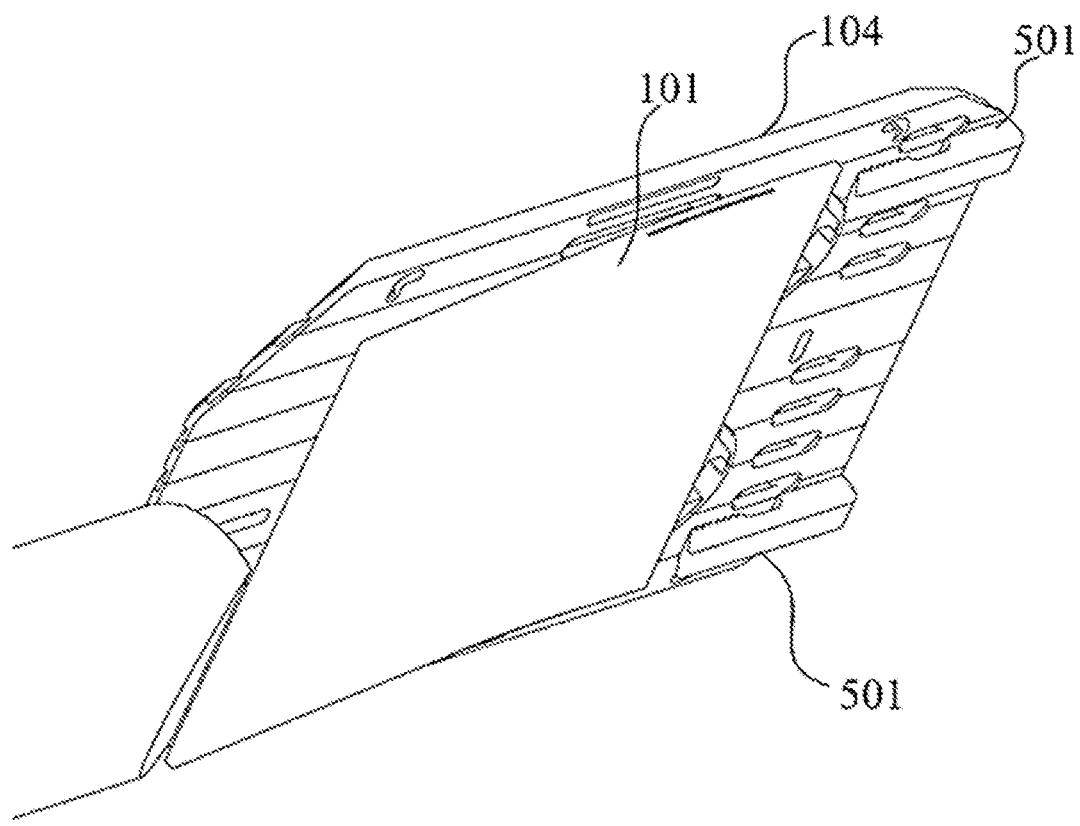
FIG. 15 shows the retaining mechanism receiving the implant.

FIG. 15 illustrates a retaining mechanism in an embodiment of the device. For example, the retaining mechanism may be a clip 501 positioned on the first surface of the deployment plate 104. The clip 501 may include a lever in which when the lever is pushed, the clip 501 opens and the implant 101 material may slide under the clip for releasably retaining the implant material.

Figure 16:
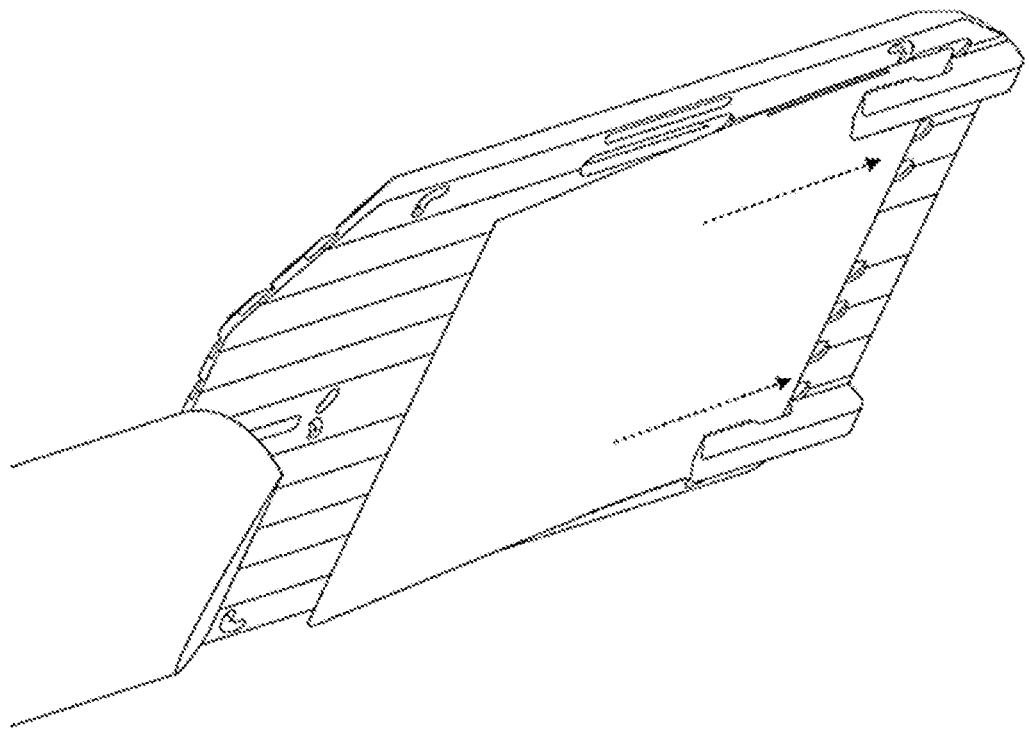
FIG. 16 shows the implant being clipped into the retaining mechanism.

FIG. 16 illustrates a sheet-like implant 101 as sliding into a retaining mechanism on the deployment plate for releasably retaining and holding the implant material. Thus, in embodiments, the reversible attachment of the implant material to the retaining mechanism of the device may be performed by the medical personnel during the surgical procedure or during device assembly. In some embodiments, the implant material may be inserted into the retaining mechanism by placing the implant material on the first surface of the deformable plate and pushing the implant material slightly such that the retaining mechanism opens to grip the material and hold it in place. The retaining mechanism 105 may be activated manually to secure the implant material to the deployment plate 104. Additionally and/or alternatively, the retaining mechanism may be actuated from the handle.

The deployment plate may be fixed into a flat position for loading the implant material onto the plate by actuation of the trigger to deploy the device into a flat position. Alternatively, the deployment plate may be manually held into a flat position for loading the implant material either manually or by other means capable of keeping the deployment plate in a flat position.

Figure 17:
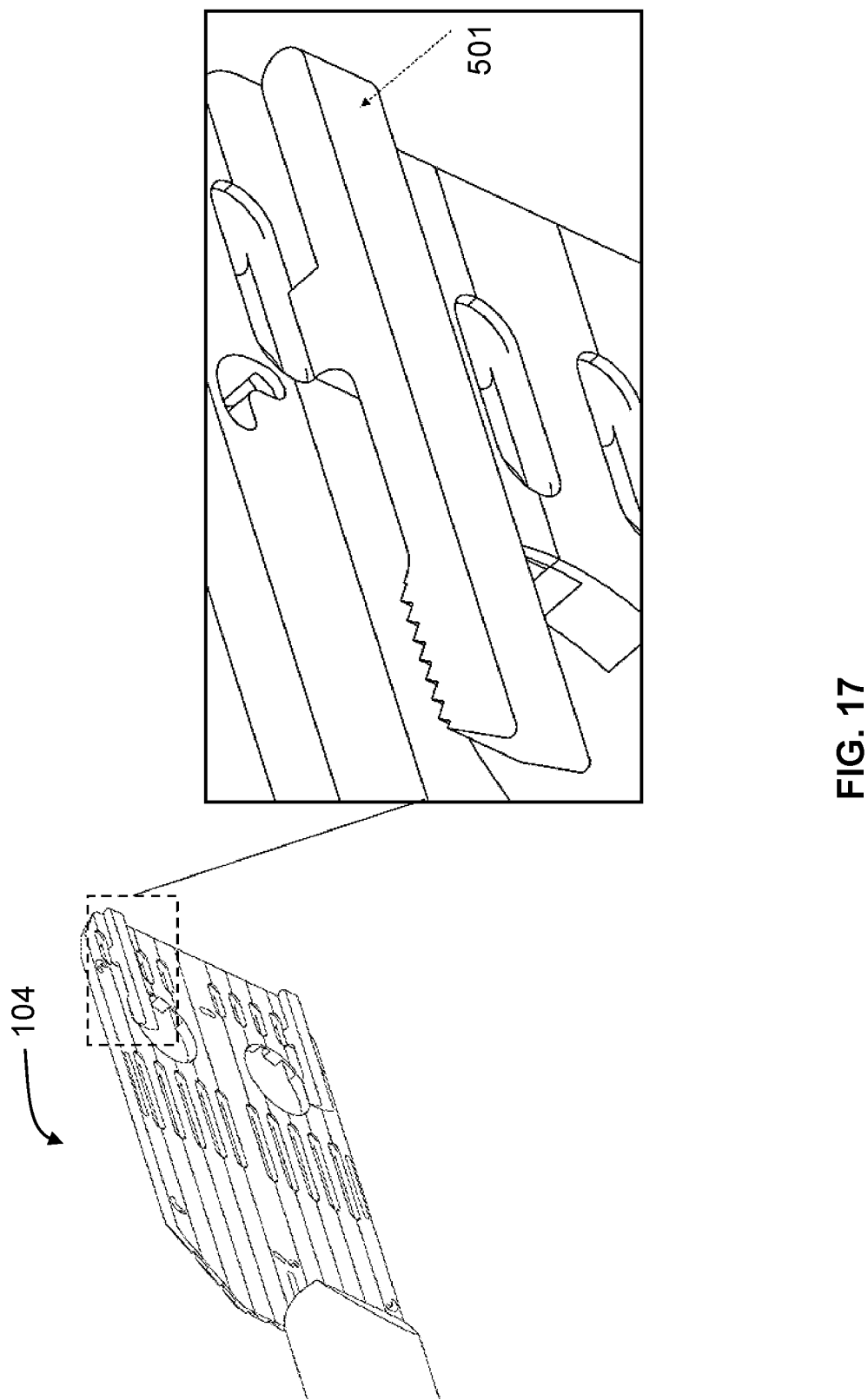
FIG. 17 is a detail view of a retaining mechanism.

FIG. 17 illustrates an embodiment of the retaining mechanism 105 of the device as a clip 501 with a lever designed to actuate opening the toothed prong of the clip such that the implant material may be retained by the deployment plate 104 under the clip 501. For example, the lever of the clip may be pressed to open the clip for loading the implant material onto the deployment plate. Pressing of the lever may be passive or active. For example, the lever may be actuated by through a mechanism retained within the handle of the device. The lever may be released such that the clip releasably grips the implant material to the first surface of the deployment plate. The deployment plate may then be collapsed into the cylindrical position for deploying the implant material through an incision, trocar, or cannula to the surgical repair site.

Figure 18:
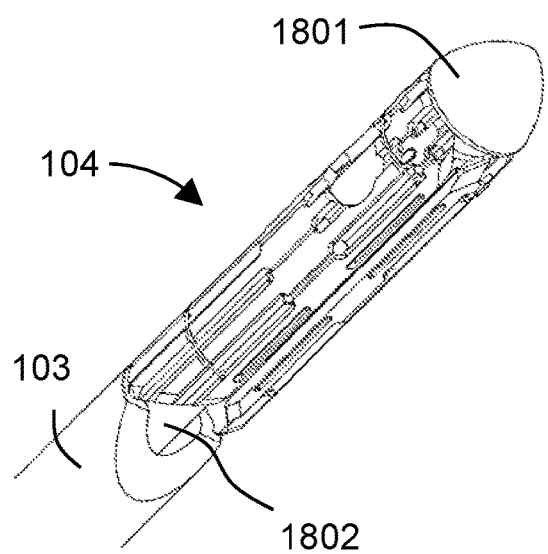
FIG. 18 shows a device with a shaped tip for delivery without a cannula.

FIG. 18 illustrates one embodiment of a device of the invention in which the device includes a forward-pointing shaped tip 1801 to allow for access to the surgical repair site without the need for a cannula or trocar. In some embodiments, the shaped tip 1801 is a rounded cone or hemisphere on an inner shaft 1802 that is housed within the distal end of the shaft 103. The inner shaft 1802 may be extendable from the distal end of the shaft 103. In some embodiments, the device includes an inner cavity within the shaft 103 to house the inner shaft 1802 such that the inner shaft 1802 is contained within the cylindrical shape of the deployment plate 104 in the closed or furled configuration. The shaped tip 1801 (e.g., rounded cone or hemisphere) may be used to push open an incision to allow for deploying and positioning the implant 101 material to the surgical repair site.

Figure 19:
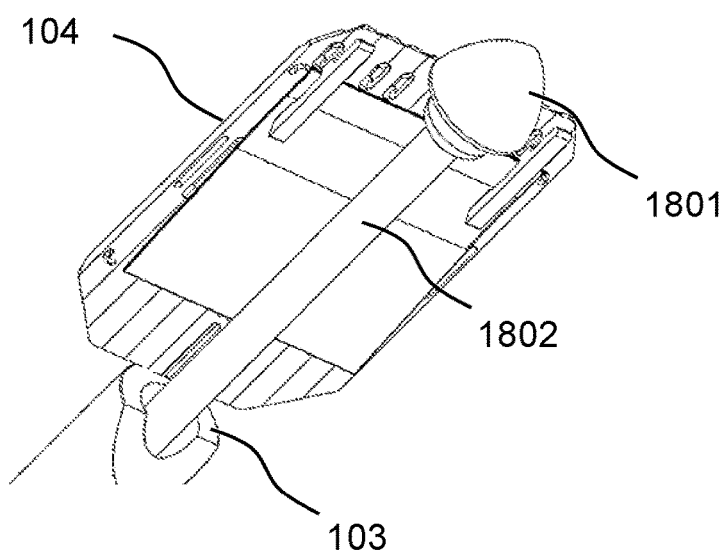
FIG. 19 shows the device with shaped tip in the open, flat configuration.

FIG. 19 shows the deployment plate 104 is in an open, unfurled, or flat configuration. As illustrated, the implant 101 material is retained on the deployment plate 104. The shaped tip 1801 is a rounded cone or hemisphere for pressing the device through an incision to a surgical repair site. After the deployment plate 104 is deployed to an unfurled position, the inner shaft 1802 connected to shaped tip 1801 is in an extended position. The shaped tip may be configured to push open an incision such that the device may be inserted into a body cavity to the repair site. For example, the tip may be conical or rounded with a sharp or blunt point to press through an incision.

In embodiments, the device includes the ability to spread a substance on or over the implant 101 material as the inner shaft 1802 may be retracted into the shaft 103. For example, the device may include an antibiotic or nutrient to facilitate tissue regeneration that is applied to or spread on the implant material at deployment.

Figure 20:
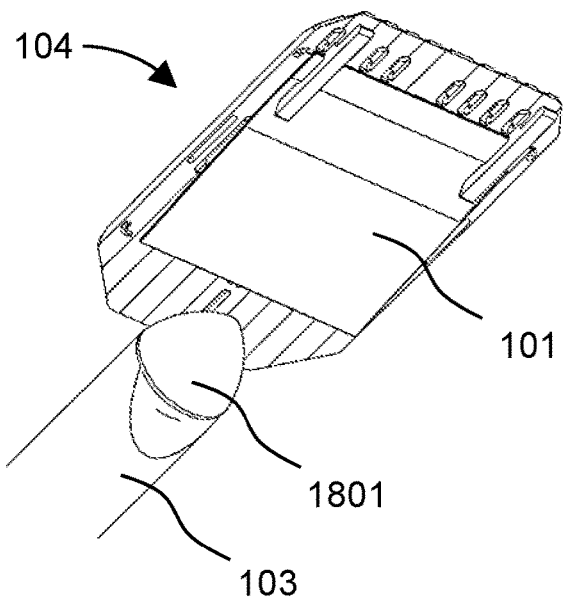
FIG. 20 is a bottom view of the device with shaped tip.

FIG. 20 illustrates retraction of the inner shaft 1802 and the tip 1801 back to the distal end of the shaft 103 such that the implant 101 material may be positioned on the tissue to be repaired.

Figure 21:
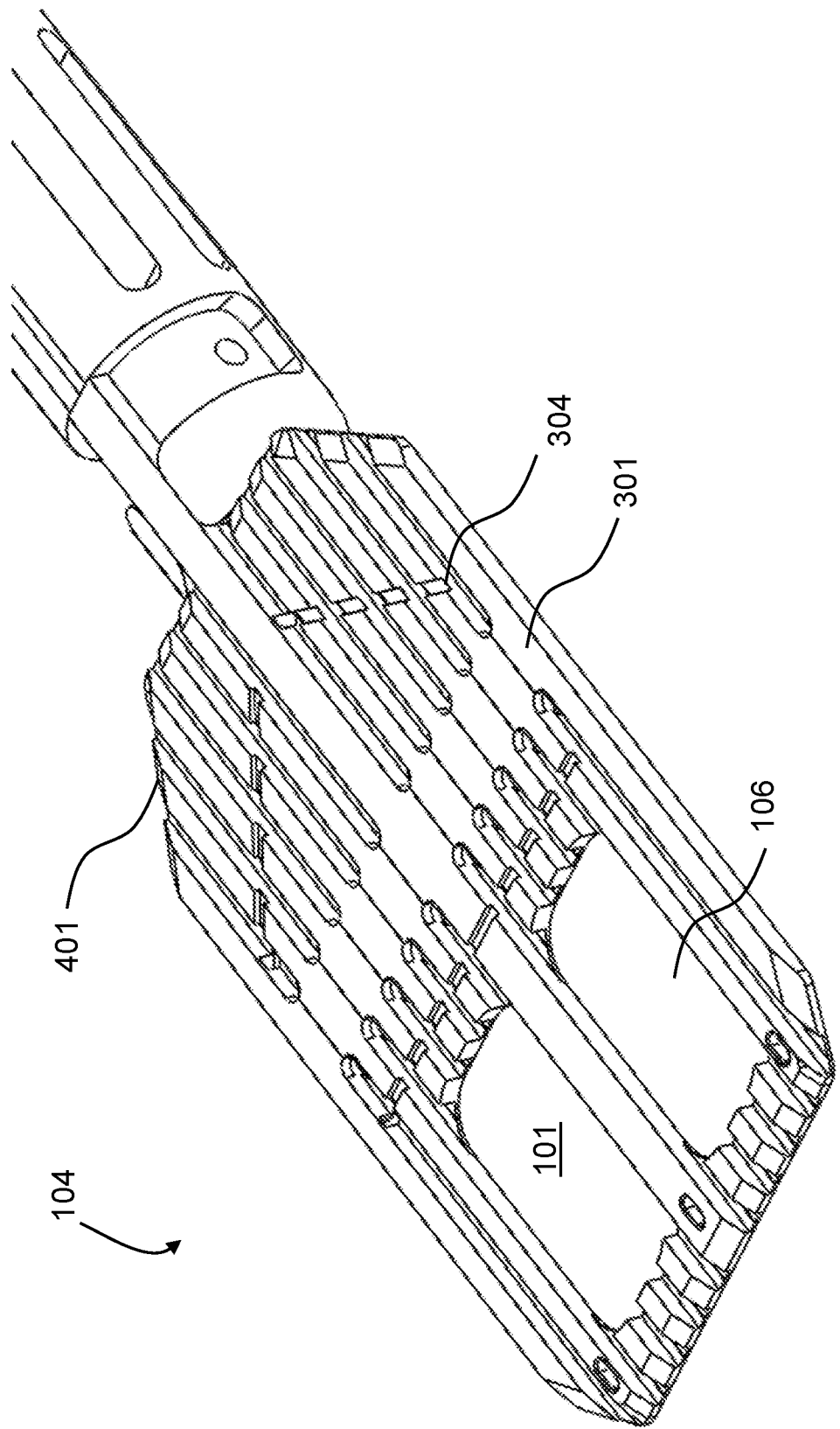
FIG. 21 shows a deformable plate or leaf with openings for attachment.

FIG. 21 shows one embodiment of a deformable plate 104 of the invention in which the plate 104 comprises one or more openings 106 through which a surgical fastener may be delivered through the sheet-like implant 101. In embodiments, the openings are designed for accessing the sheet-like implant to secure the implant to tissue. As illustrated, the implant 101 material may be retained on the first surface of the deformable plate 104 such that a portion of the implant 101 material is accessible through the opening 106 in the deformable plate 104. In embodiments, the opening is shaped as a circle, or as a rectangle. The one or more openings may be any shape that allows the placement of a surgical fastener through the opening into the implant material and into the underlying tissue. In embodiments, the one or more openings are sized for a tack, staple, or suture. The surgical fastener, for example, a tack or staple, may be applied using a separate device configured for surgical fastening or suturing.

In some embodiments, the first surface of the deformable plate is dimensioned to carry a collagen patch for a rotator cuff repair. For example, the deformable plate may be dimensioned for a graft material for interposition grafting or a gap-bridging procedure and/or superior capsule reconstruction. In embodiments, the sheet-like material is an orthopedic implant as described herein.

Figure 22:
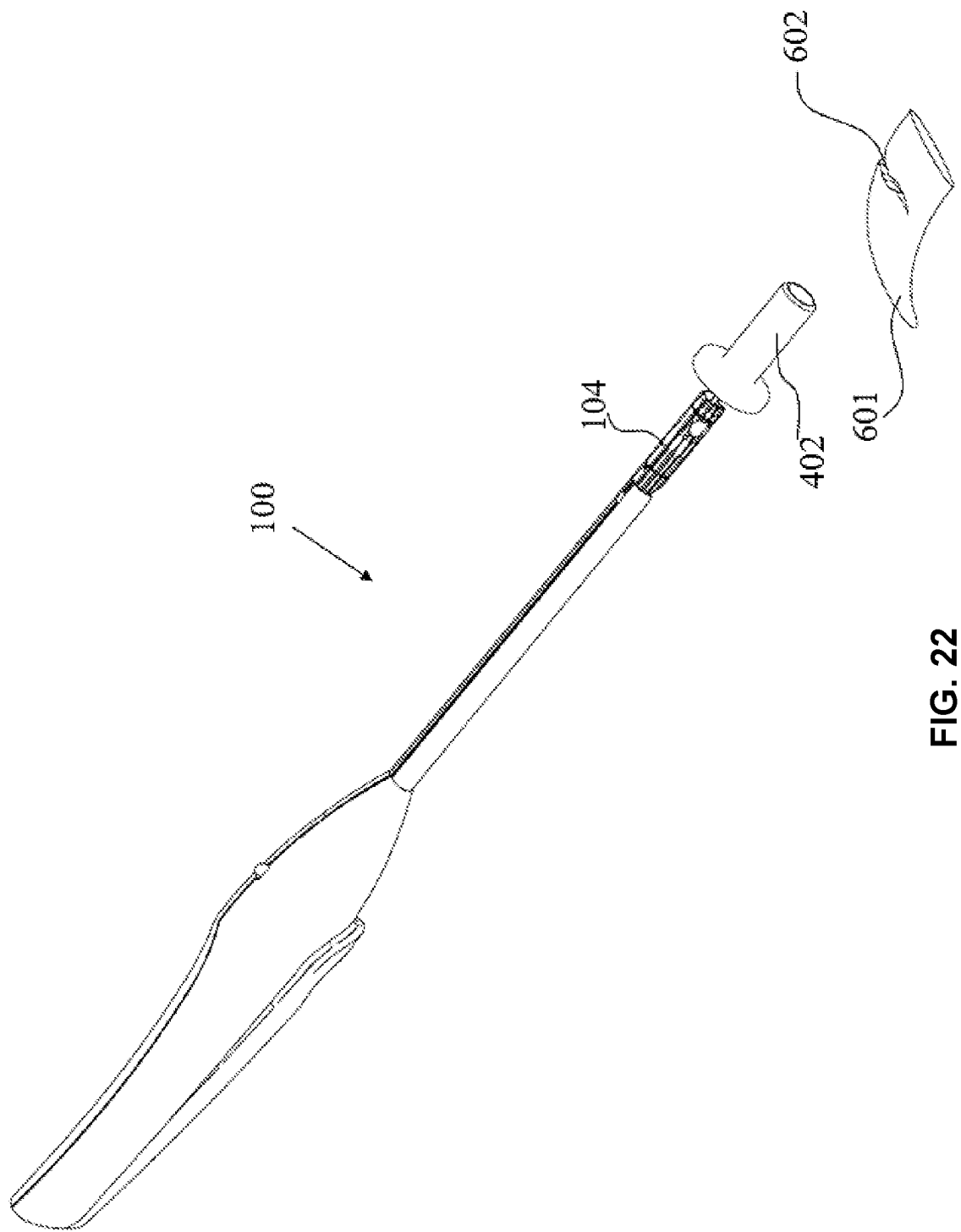
FIG. 22 shows a method step of relaxing a trigger to curl an implant for delivery.

FIG. 22 shows a method step of relaxing a trigger to curl an implant for delivery, in which the device 100 with the deformable plate 104 in a cylindrical first position as it is about to be inserted into a cannula 402. The sheet-like implant 101 may be retained on the first surface of the deformable plate and rolled within the interior of the cylindrical shape of the deformable plate. The figure illustrates the tissue 601 and a tear 602 in the tissue at the surgical repair site that the device may be used to position the implant for repair. Notably, the trigger is not yet pressed or depressed, thus keeping the tension on the deployment wire minimal such that the deformable plate retains its first, cylindrical configuration, i.e. the trigger has not yet actuated the deployment wire.

FIGS. 14-17 and 22-26 (among others) also show an implant delivery device that includes an extended shaft with a proximal portion and a distal portion; a handle, or a mechanism for attachment of the shaft to a handle or a robot, on the proximal portion of the shaft; and a furlable leaf at the distal portion of the shaft. The device includes a clip operable to releasably pin a sheet-like implant to a first face of the leaf and a tensioning member through the shaft tensionable to move the leaf between a curled first shape and a flat second shape. FIG. 6 shows the tensioning member as a wire. The leaf may include one or more hinges, each having a hinge axis parallel to an axis of the curled first shape. Preferably, the leaf is provided by a single, monolithic piece of material and the hinges are living hinges defined by channels in the material along each hinge axis along a second face of the leaf obverse to the first face. As shown in FIG. 7 and FIG. 8, the living hinges may include overhanging ledges 305 that limit opening of the furlable leaf beyond a predetermined amount (e.g., beyond flat). For example, the ledges may include first and second edges overhanging channels defining the living hinges, such that when the leaf is deformed in a flat position the first and second edges are in contact to prevent the leaf from deploying past 180 degrees. In preferred embodiments, the proximal portion of the shaft is attached to a handle. In certain embodiments, tensioning member includes a wire extending from the trigger on the handle mounted on the proximal portion, through the shaft, and through a channel within a second face of the leaf, such that squeezing the trigger pulls the wire in a proximal direction along the shaft, deforming the leaf from the curled first shape into the flat second shape. Preferably in these certain aspects, the sheet-like implant is slidable into the clip and is retained in the clip until released by the device. The shaft and the leaf, when in curled first shape, are sized to fit through a cannula, e.g., with an inner bore with a diameter of about 10 mm. The leaf may include ramped edges configured to push the leaf into curled first shape when the leaf is pushed or pulled into the bore of a cannula. Openings or holes through the leaf may be provided, through which a tack or suture may be delivered to the implant.

Figure 23:
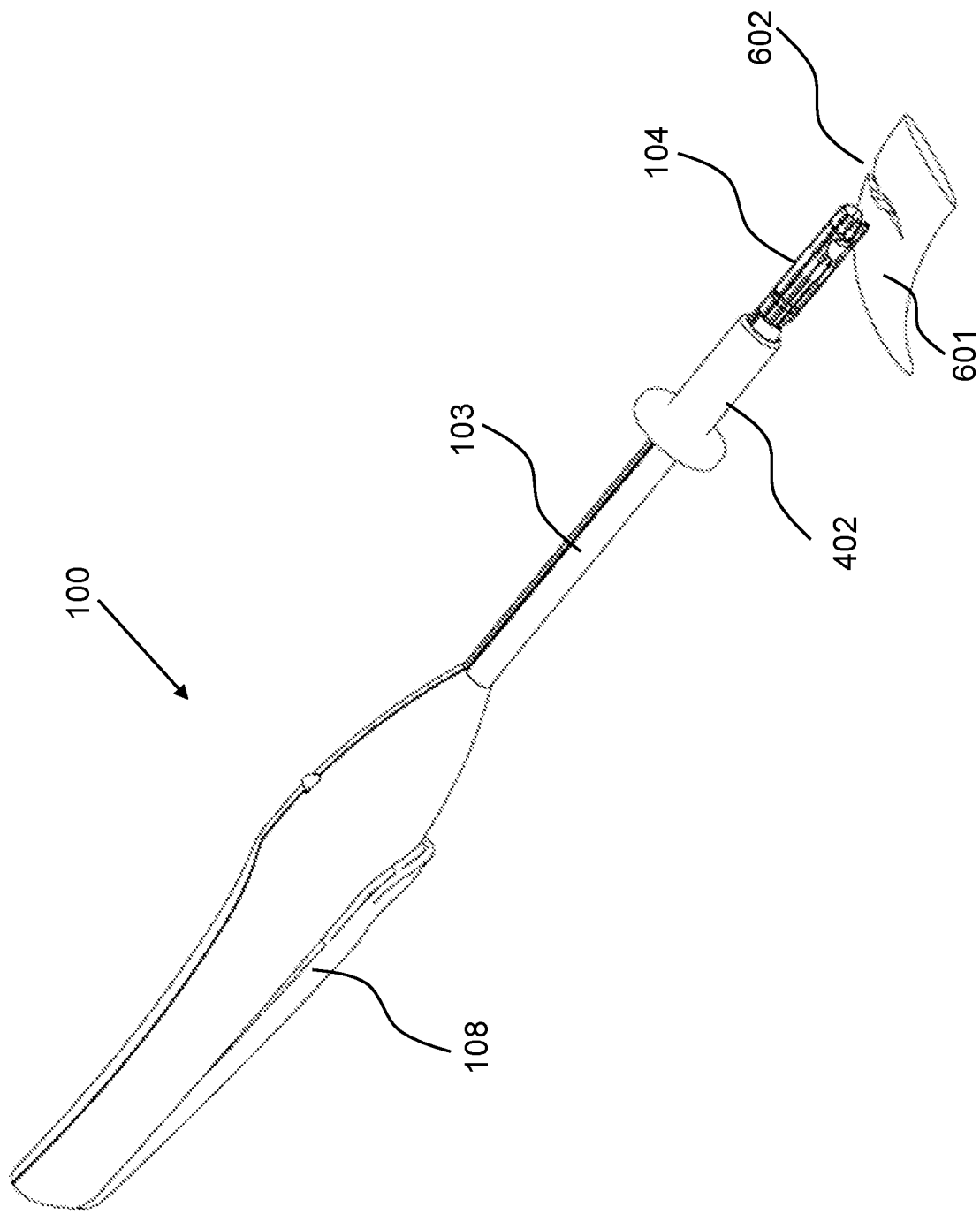
FIG. 23 shows inserting the closed plate with implant through a cannula.

FIG. 23 illustrates the deformable plate 104 (aka furlable leaf) and part of the shaft 103 of the device 100 as pushed through the cannula 402 to the tissue 601 to be positioned over the tear 602. The furlable leaf is shown in its a curled first shape.

Figure 24:
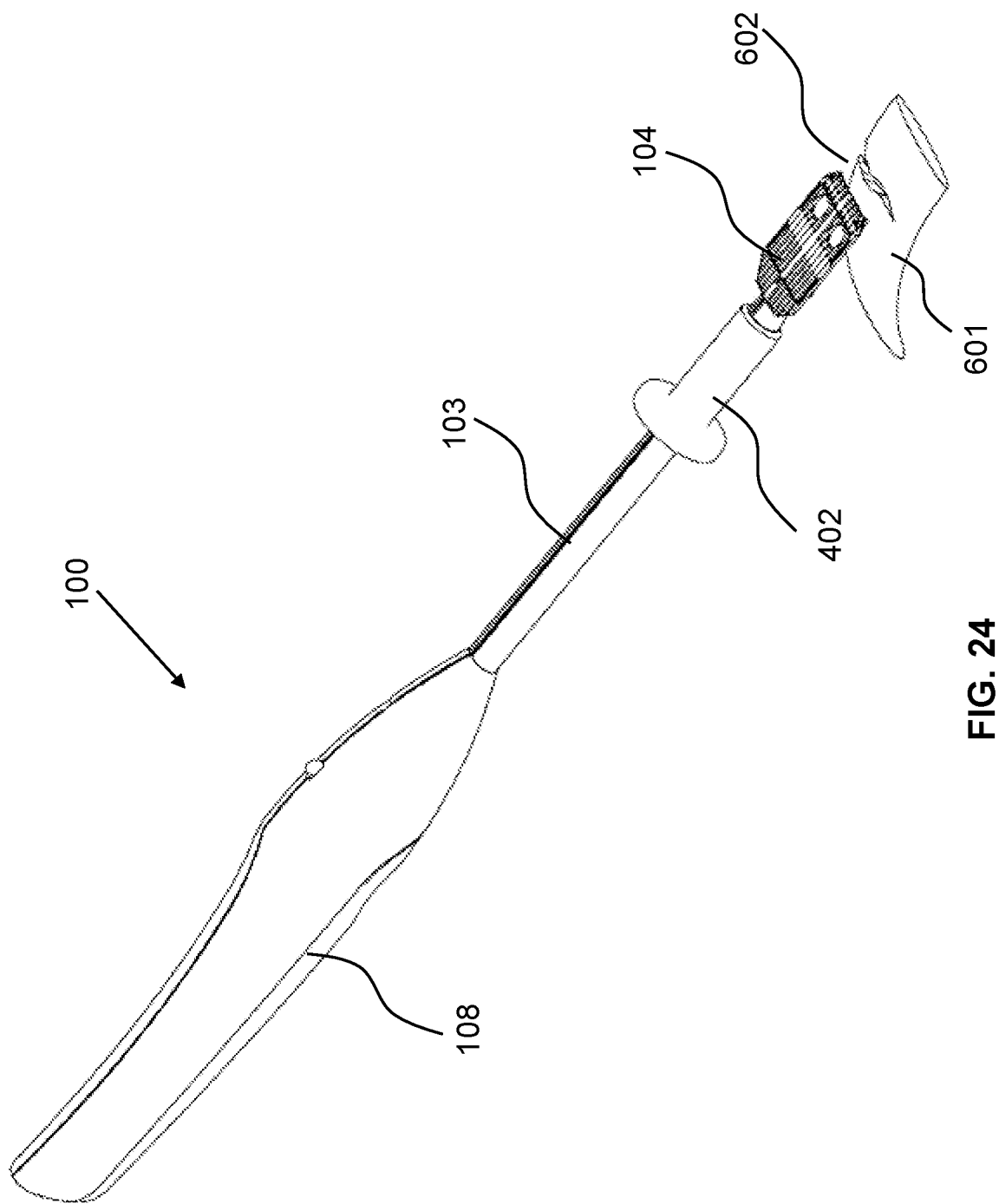
FIG. 24 shows opening the deformable plate and positioning the implant.

FIG. 24 illustrates the trigger 108 of the device 100 has been pressed to actuate the tension on the deployment wire 303 such that the wire has pulled the deformable plate 104 (aka furlable leaf) into a flat configuration. The furlable leaf is in its flat second shape.

Figure 25:
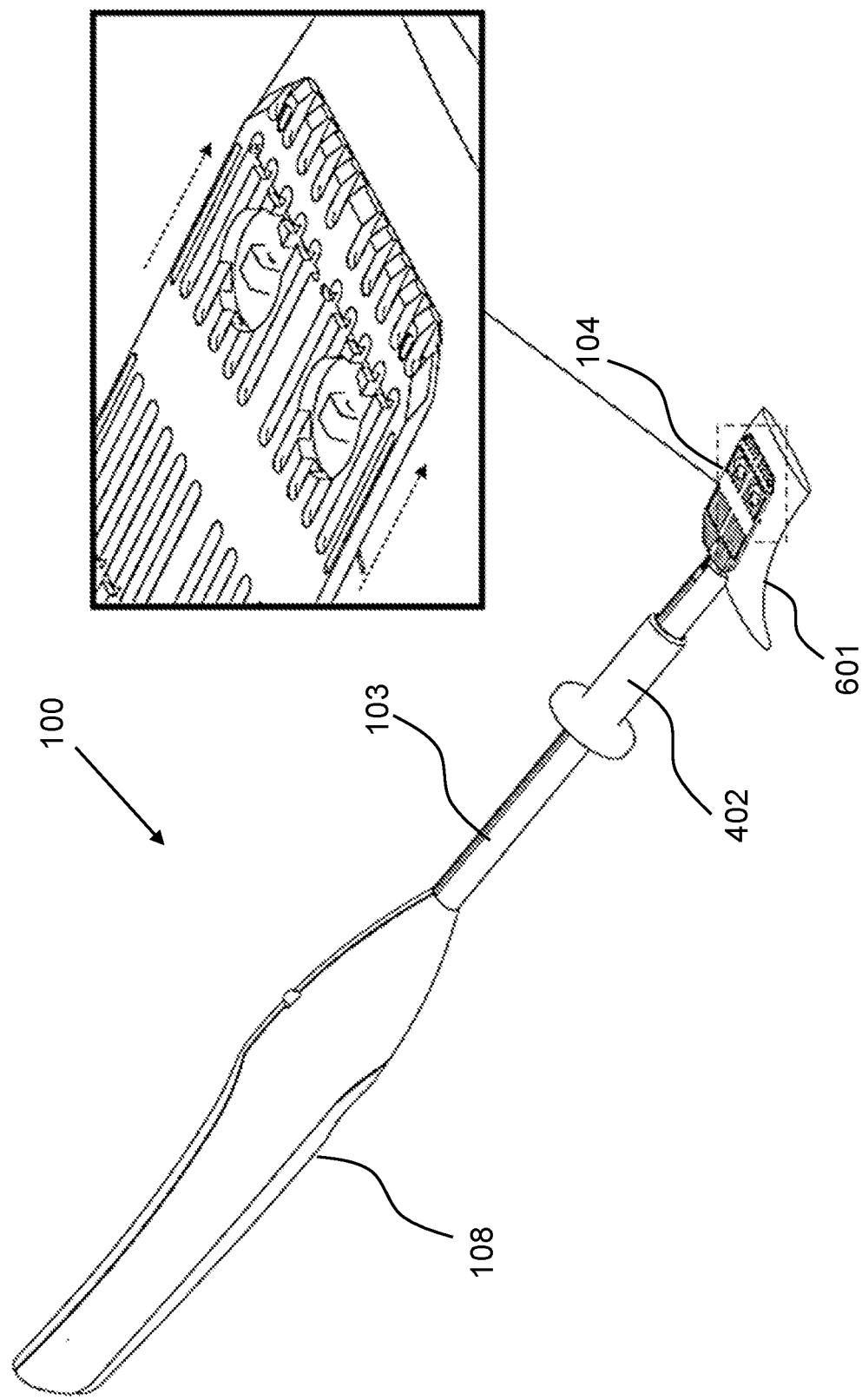
FIG. 25 shows attaching the implant and lifting the delivery device away.

FIG. 25 illustrates positioning of the deformable plate 104 over the tear 602 (not shown) in the tissue 601. Once the implant material is placed over the tear, a separate device may be used to access the implant through the openings in the device to surgically fasten the implant material to the tissue. As shown in the inset of FIG. 25, the implant material has been tacked to tissue through the openings in the device. As shown in the inset, the implant material has been attached to the tissue via a surgical fastener, such as a tack or staple. In this embodiment, the deformable plate 104 has moved from a cylindrical first position to a flat position via actuation of the trigger 108 and tension has been applied to the deployment wire 303 to deform the deformable plate 104 from a cylindrical configuration to the flat configuration. In this way, the implant 101 material, e.g. an orthopedic graft or patch, may be placed over the tear 602 in the tissue 601.

To remove the deformable plate from the implant material after the implant material has been partially or fully secured to the tissue, the device may be pushed forward such that the device slides out of contact with the implant material.

Figure 26:
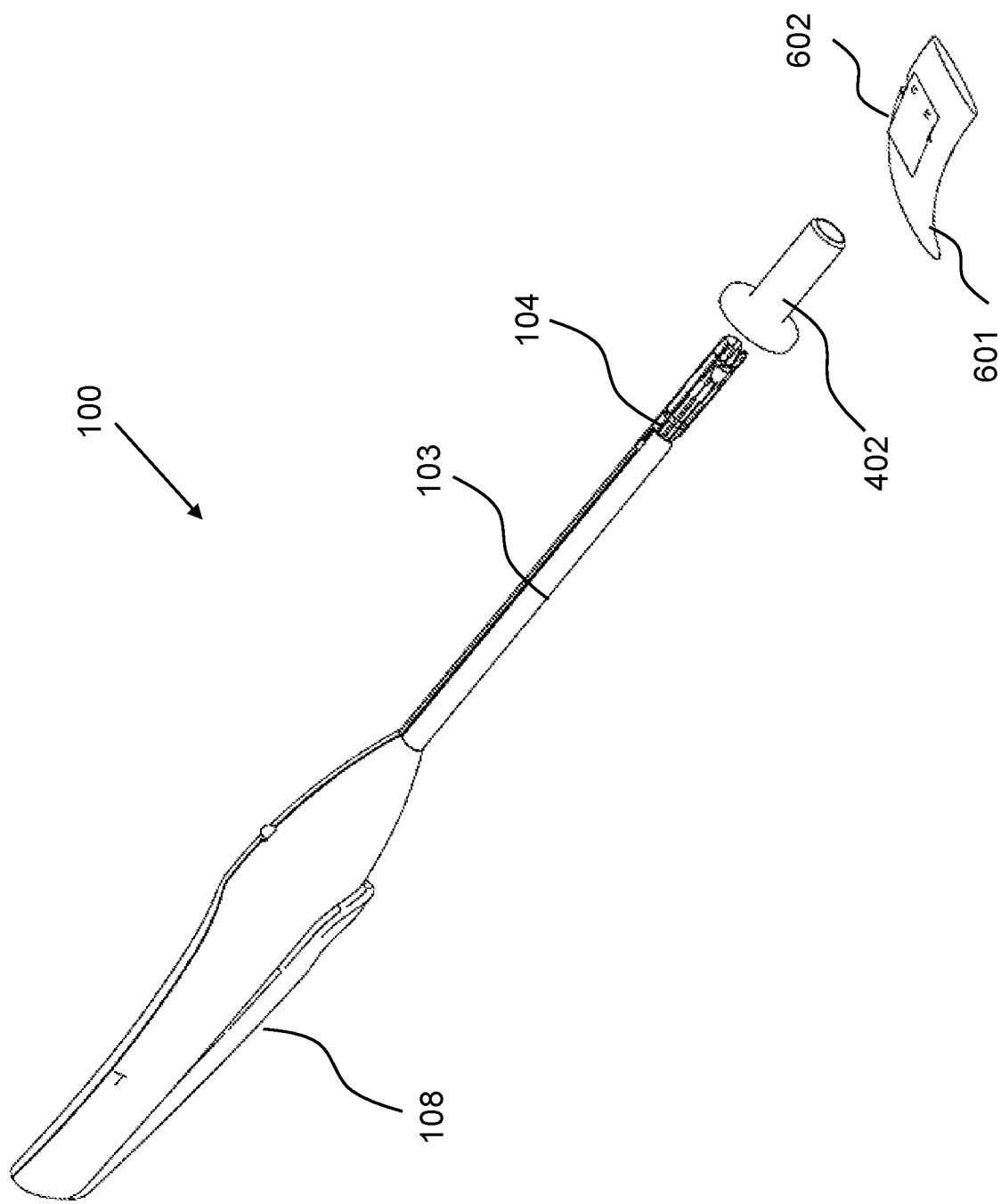
FIG. 26 shows curling the device back closed and withdrawing the device.

FIG. 26 illustrates the implant material after fastening the implant material to the tissue 601 over a tear 602 and release by the device 100. The deformable plate 104 has been retracted to a cylindrical first configuration. For example, in some embodiments, the tension actuated by the trigger 108 on the deployment wire has been released. Thus the shaft 103 with deformable plate 104 have been pulled out of the cannula 402.

Figure 27:
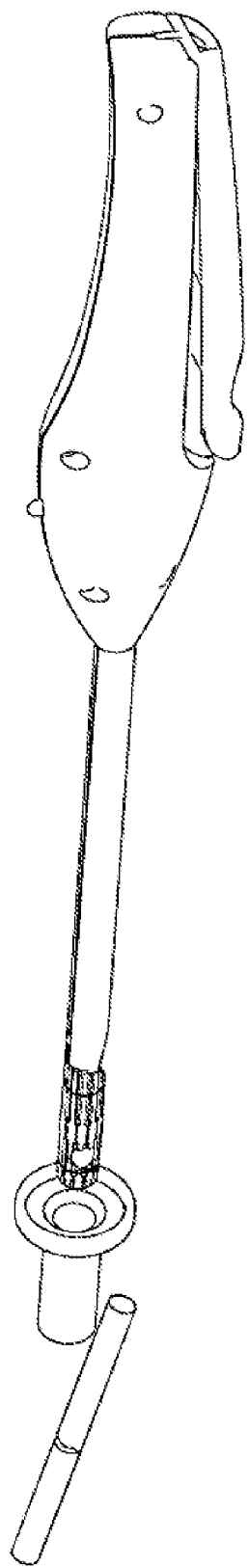
FIG. 27 shows using the device to approach a damaged tendon or vessel.
Figure 28:
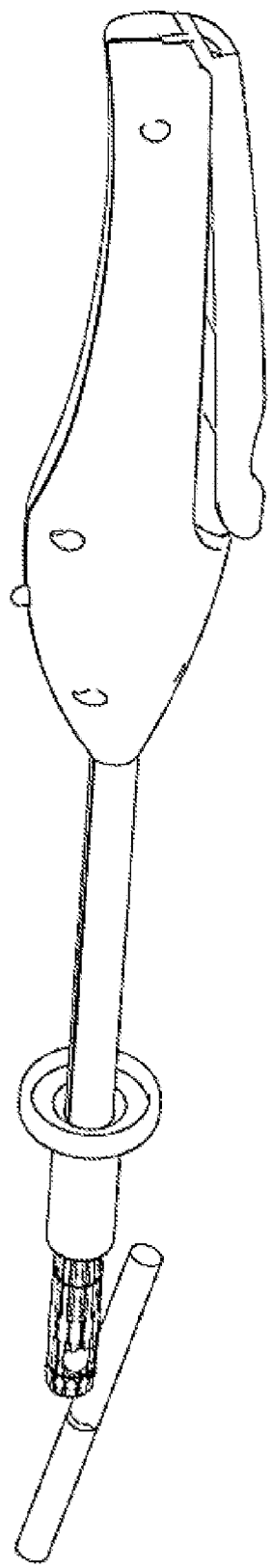
FIG. 28 shows the device, through a cannula, approaching the tendon or vessel.

FIG. 27 shows a device of the invention positioning the deformable plate to enter a cannula at a surgical repair site comprising a tear in a tendon. As shown, the deformable plate is operational to deform around a ligament or tubular vessel. In this way, some embodiments of the device are configured to place an implant material on damaged tendons, ligaments, or round bodies. For example, FIG. 28 illustrates the deformable plate as positioned through the cannula and over the tendon. The deformable plate is in a cylindrical first configuration.

Figure 29:
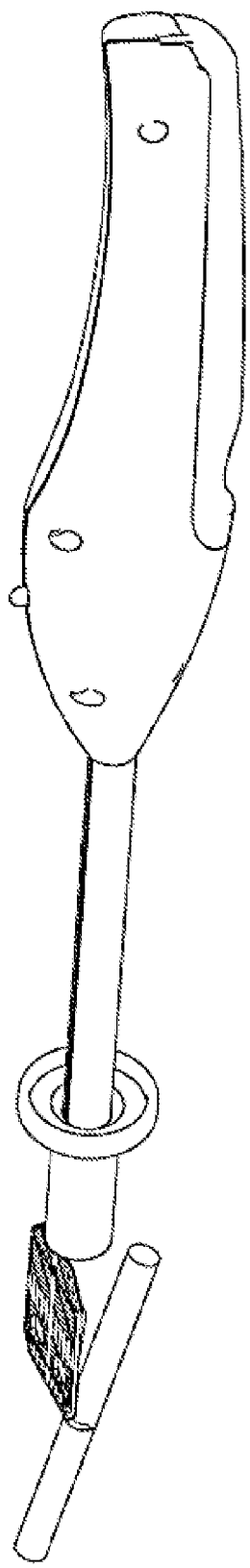
FIG. 29 shows opening the deformable plate adjacent the tendon or vessel.

FIG. 29 shows the deformable plate as opened into a flat second configuration.

Figure 30:
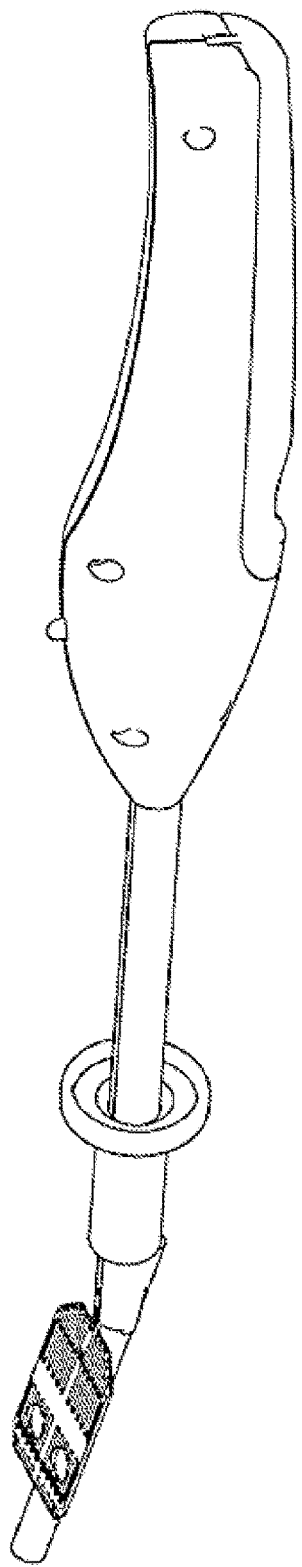
FIG. 30 shows positioning an implant on the tendon or vessel.

FIG. 30 shows that the deformable plate, in the flat configuration, may be placed over the tear in the tendon such that the implant graft retained on the underside or first surface of the plate is in contact with the tissue.

Figure 31:
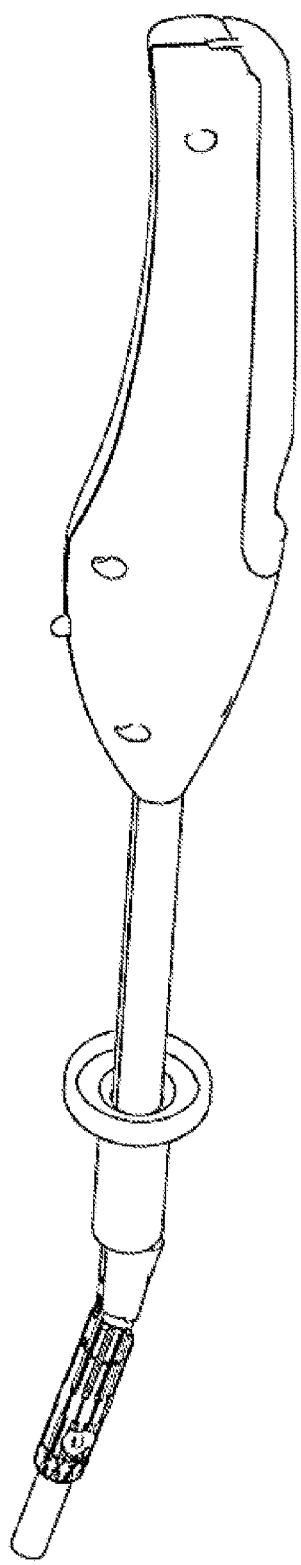
FIG. 31 shows wrapping the implant around the tendon or vessel.
Figure 32:
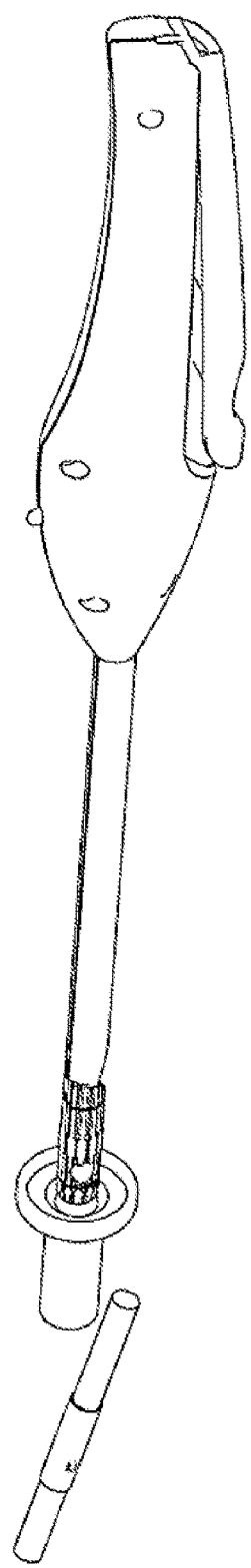
FIG. 32 shows withdrawing the device from the surgical site.

FIG. 31 illustrates that the device may be closed, i.e. returned to a cylindrical position, around the tendon to wrap the implant material around the tendon. The graft material may be accessed for fixing to the tendon through the one or more openings in the deformable plate. These images also describe use of the device for vascular anastomosis. Once the implant material is affixed to the tissue, the plate may be removed from the implant material by pressing the plate forward to release the implant material. In embodiments, the deformable plate releases the implant material through actuation of a mechanism in the handle operably connected to the trigger.

Notably, the device may be used for positioning an implant material on both flat/semi-flat tissue surfaces and round bodies such as an artery or other vessel. In embodiments, the device may be used for tendons, bones, and other structures within the body. Devices of the invention may be used for shoulder surgery, such as rotator cuff surgery, or other orthopedic repairs such meniscus regeneration/transplantation, anterior cruciate ligament reconstruction (ACL), nerve allografts, osteochondral grafts, and valve repair and/or replacement.

In specific embodiments, the current invention discloses a novel device and method for insertion and deployment of a graft, implant, or a patch into a body cavity, e.g. allograft implantation on top of a torn rotator cuff during arthroscopic rotator cuff repair, for example as described in Wall, 2018, How to use a graft in irreparable rotator cuff tears: a literature review update of interposition and superior capsule reconstruction techniques, Curr Rev Musculoskel Med 11(1): 122-130, incorporated by reference.

Figures 33, 34:
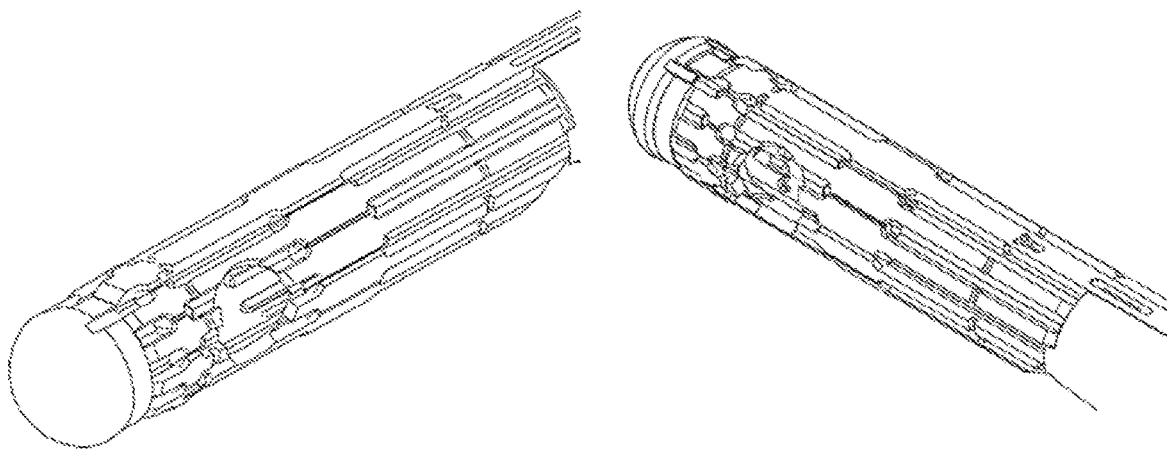
FIG. 33 is a top view of a closed device with repositionable shaped tip.
FIG. 34 is a bottom view of a closed device with repositionable shaped tip.

FIG. 33 is a top view of a closed device with repositionable shaped tip here present as a domed (or hemispherical) cap.

FIG. 34 is a bottom view of a closed device with the repositionable domed cap. The domed cap may be used to help guide the deformable plate through an incision, cannula, or trocar such that the deformable plate retains a cylindrical shape when pressure is applied at insertion. In some embodiments, the cap is actuated to open and close by action of the trigger.

Figures 35, 36:
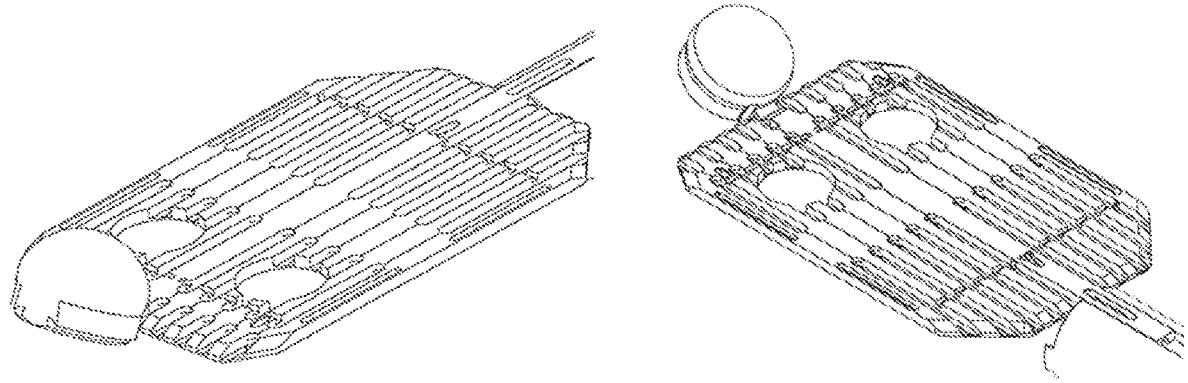
FIG. 35 is a top, front view of an open device with repositionable shaped tip.
FIG. 36 is a top, back view of an open device with repositionable shaped tip.

FIG. 35 is a top, front view of an open device with the domed cap.

FIG. 36 is a top, back view of an open device with the domed (e.g., hemispherical) cap. In some embodiments, the domed cap may be operably connected to the deployment wire and may open upon tension applied to the wire such that when the deformable plate is in a flat position, the cap is flexed to an open position. In embodiments, the cap may be rounded, a rounded cone, domed, or hemispherical. In other embodiments, the cap may include a point to facilitate pushing the device through an incision.

In related aspects, the invention provides an implant delivery device in which the deployment support is a deformable leaf. The device includes a delivery shaft having a proximal portion and a distal portion, a handle on the proximal portion of the shaft and the deformable leaf on the distal portion of the shaft. The deformable leaf includes a retainer mechanism on the leaf operable to releasably hold a sheet-like implant against a first face of the leaf. The device includes a trigger on the handle operable to move the leaf between a cylindrical first configuration and a flat second configuration.

As noted above, the deformable leaf may be positioned into at least two configurations: (1) a substantially cylindrically shaped, i.e. a furled or closed configuration, in which the deformable leaf is shaped as a tube, along the length of the leaf, with the graft or implant material retained along the inside wall, i.e. first surface, and (2) a substantially flat configuration, i.e. furled or opened.

The deformable leaf may be a plastic that is shaped or molded. The leaf may be made of a flexible material, for example a flexible polymer such as polyoxymethylene (POM) or acetal, or polypropylene. The leaf may be preformed into a furled or cylindrical configuration, for example by using injection molding, 3D-printing, or computerized manufacturing processes (CNC) techniques known to persons skilled in the art. The leaf may be further prepared and shaped into a preformed cylindrical shape using a plastic annealing process.

The leaf may be pre-shaped to collapse into a cylindrical shape or to be elastically biased into a cylindrical shape. For example, the leaf may be elastically biased into a substantially cylindrical position as a result of the material used and/or an annealing process. The leaf may be made of a shape-memory polymer, for example, a thermoplastic and/or thermoset (covalently cross-linked) polymeric material. The leaf may be made of a shape memory metal. For example, the leaf may be a nickel-titanium alloy such as Nitinol. The leaf may be formed as a single piece or as several pieces assembled and connected so as to retain a cylindrical configuration.

Additionally and/or alternatively, the leaf may be retained in a substantially cylindrical position via hinges and/or springs. Importantly, the deformable leaf may be any shape, for example a rectangular, oval, irregular, square, customized, leaf-like, or circular shape. In embodiments, the deformable plate is polygonal, for example an octagon.

In some embodiments, the first surface of the deformable leaf may be a single, monolithic piece of material. Thus, the first surface may be a flat surface upon which an implant material may be retained. The deformable leaf may include a plurality of channels or sections in the second surface that operate as a living hinge allowing the deformable leaf to be pulled from the cylindrical first configuration to the flat second configuration. As noted, the cylindrical first configuration may also be referred to as a closed or furled position such that an implant retained upon the plate is neatly and securely rolled within the inner confines of the configuration. In some embodiments, the flexibility of the material from which the deformable leaf is made, for example a flexible plastic, may act as a spring to retain the cylindrical configuration. In other embodiments, the device includes a spring to hold the deformable leaf in a closed cylindrical configuration.

In embodiments, the deformable leaf comprises a series of long rigid or semi-rigid sections connected via a series of hinges located near the inner portion of the leaf. The ridges may be a plurality of parallel channels in the second surface running lengthwise on the plate from a proximal end to a distal end, or spaces in between. The plurality of channels may be described as slots running lengthwise on the deformable plate from a proximal end to a distal end. For example, the ridges and/or channels may be formed on the second surface as part of the molding process.

In some embodiments, the deformable leaf includes one or more hinges, each hinge having a hinge axis parallel to an axis of the cylindrically-shaped first position. In some embodiments, the hinges are living hinges, i.e. thin and flexible sections of the material adapted to be deformed during operation of the device. The living hinge may be a thin piece of plastic surrounded by the thicker plastic of the ridges that allow the leaf to bend at the sections from 1 degree to 180 degrees. The hinges may be located on the first surface of the leaf to allow the leaf to move from a substantially cylindrical first configuration to a substantially flat second configuration. The living hinges may be formed by cutting or scoring the deformable leaf on the second surface between the ridges or slots, or on the top of the channels. Cutting or scoring the deformable leaf may take place after molding the deformable leaf via an injection molding process.

In some embodiments, the deformable leaf includes a plurality of individual rigid or semi-rigid sections coupled together via a hinge material. The hinge material may be a plastic or metal hinge actuated by spring mechanism.

Notably, the deformable leaf may include a series of limiters to prevent sections from rotating beyond a flat angle. For example, the second surface may include extensions that overhang the channels such that when the deformable leaf is pulled to the flat second configuration, the extensions prevent the deformable leaf from deploying past about 180 degrees. Notably, deformation of the deformable leaf may encompass a range of configurations between substantially cylindrical and substantially flat, such that a configuration past a 180-degree flat position may be prevented by the limiter.

In some embodiments, the limiters may be small pieces of material located on the second surface, for example above the hinges located on the first surface. The limiters act as a stop or obstruction to limit the opening of the plate past a flat configuration and/or collapsing past a flat configuration. Thus, when tension is applied to the deployment wire, the limiters may come in contact with each other to prevent the plate from opening or deploying past about 180 degrees.

In some embodiments, the limiters may be projections, segments, or stops integrally formed as part of the second surface. The limiters may be projections, segments, or stops added to the second surface to prevent opening or deployment of the leaf past about 180 degrees. The limiter may be one continuous piece formed at manufacture, for example via injection molding, and then cut to form a living hinge on the first surface of the leaf with the limiter on the second surface of the plate between the ridges.

In some embodiments, the limiter may include a first edge and a second edge associated with a hinge such that when the leaf is deformed in a flat position the first and second edges are in contact to prevent the plate from deploying past 180 degrees.

In some embodiments, and as noted above, the device may include a deployment wire extending from the trigger, through the shaft, and through a channel adjacent a second face of the leaf, such that squeezing the trigger pulls the wire in a proximal direction along the shaft, deforming the leaf from the cylindrical first configuration to the flat second configuration. The deployment wire or thread may extend from the trigger and through a loop channel within the deformable leaf such that tensioning the wire by the trigger pulls the deformable leaf from a cylindrical first position to the flat second position.

The deployment wire may be located above the hinges such that once tension is applied to the deployment wire each one of the sections is rotated upward in relation to the hinges and the deformable leaf is transformed into a flat configuration. Notably, the implant material is retained on the first surface of the device within the interior of the cylindrical shape. In this way, the material is protected from tearing or damage during insertion, positioning, and deployment to the repair site.

As noted above, the trigger and deployment wire may be operably connected wherein actuation of the trigger exerts the tension on the wire necessary to transition the deformable leaf from a cylindrical or furled first position to a substantially flat or unfurled position. The handle of the device may further include a latch operably connected to the trigger and to the wire, and a trigger spring operably connected to the trigger. The latch may be operable to lock the deformable leaf into a fixed position. The fixed position may be a substantially cylindrical position, a substantially flat position, and/or any position between cylindrical and flat.

In some embodiments, the trigger may be moved to, and held in, a plurality of different positions between an open rest position and a fully-closed position. For example, a rest position may be one in which i.e. a position in which there may be no or limited tension applied to the deployment wire. A fully-closed position may be a position in which a maximum amount of tension is applied to the deployment wire. In some embodiments, the trigger is configured to lock the deformable leaf into any number of positions by a locking mechanism operably coupled to the trigger and the deployment wire. For example, the deformable leaf may be locked into the cylindrical position, a position in-between cylindrical and flat, or in a substantially flat position.

The locking mechanism may lock the tension applied to the deployment wire in a rest or fully-closed position, or any position in-between. Specifically, in some embodiments, the deformable leaf may be held, by one-handed operation of the trigger in any position along a continuum between a cylindrical first configuration and a flat second configuration. In this way, one-handed operation of the device leaves a free hand for a surgeon to operate a separate second device, such as a device for fixing the implant material to tissue.

The device may also include a lever spring or trigger spring operably connected to the trigger to facilitate actuation of the trigger. For example, pressing the trigger may compress the lever spring to such that the latch locks (or unlocks) the trigger into a fixed position. With the trigger locked into a fixed position, the tension upon the deployment wire may remain fixed thus locking the deformable leaf into a fixed configuration. The latch may be released by pressing the trigger again. The lever spring may facilitate the return of the trigger to a rest position in which the tension on the deployment wire is minimal.

In embodiments, when the trigger is activated, for example, the trigger is pressed, the spring opens and the deployment wire attached to the trigger is pulled back such that tension for deployment of the deformable leaf from the cylindrical position is created. In other embodiments, the spring is separate from the trigger or lever. The trigger may be pressed towards the body of the handle such that tension is applied to the deployment wire. This tension causes the deployment wire to pull the deformable leaf from a cylindrical position, i.e. a rest or un-tensioned position to an open position. The degree to which the trigger is pressed may actuate the degree to which tension is applied to the deployment wire.

Additionally and/or alternatively, embodiments of the device may include a ratchet mechanism to allow for the flexible opening and closing of the deformable leaf. For example, the ratchet mechanism may allow the user to move the deformable leaf from a substantially cylindrical position, i.e. closed or furled, and open or unfurl, and then hold/lock, the deformable leaf in any number of positions for suitable placement of the implant material onto tissue. For example, the ratchet may include a spring loaded pawl on saw teeth, flexible metal sheet sliding over cam or saw teeth, or other ratchet mechanisms known to those skilled in the art.

As is described above, the implant material may be releasably retained on the device using a retainer mechanism. In embodiments, the retaining mechanism may be one or more clips operable to releasably hold the sheet-like implant against the first face of the leaf. For example, the clip may include a prong with teeth on the underside of the prong with which to lightly grip the implant material and secure the implant material to the first surface of the deployment plate. The clip may include a lever whereby pressing the lever actuates the prong to open up such that the implant material may be placed underneath the prong. Releasing the lever may cause the clip teeth to close onto the implant material to retain the implant material on the first surface or face of the deformable leaf. Thus, the action necessary for gripping the implant material and retaining the implant material upon the deformable leaf may be actuated.

The retaining mechanism, such as one or more clips, may be molded from the same piece of material as the deformable leaf, for example, as part of a single, monolithic piece of material. Additionally and/or alternatively, the retaining mechanism may be made from a different material or a separate mold that is glued to the first face of the deformable leaf and/or heat stacked.

The retaining mechanism may be a slot configured to hold the implant material by sliding the implant material into the slot. The retaining mechanism may be one or more clips adapted to enable a reversible connection of the implant material to the deformable leaf.

The retaining mechanism may be a clip with a lever. For example, the lever of the clip may be pressed to open the clip for loading the implant material onto the deformable leaf. Pressing of the lever may be passive or active. For example, the lever may be actuated through a mechanism retained within the handle of the device. The deformable leaf may be fixed into a flat position for loading the implant material onto the leaf by actuation of the trigger to deploy the device into a flat position. Alternatively, the deformable leaf may be manually held into a flat position for loading the implant material either manually or by other means capable of keeping the deformable leaf in a flat position. The lever may be released such that the clip releasably grips the implant material to the first surface of the deformable leaf. The deformable leaf may then be collapsed into the cylindrical position for deploying the implant material through an incision, trocar, or cannula to the surgical repair site.

In embodiments, the implant material may be inserted into the retaining mechanism by placing the implant material on the first surface of the deformable leaf and pushing the implant material slightly such that the retaining mechanism opens to grip the material and hold it in place.

The device may be designed such that the deformable leaf, when in the cylindrical first position, is sized to be delivered to a joint or cavity inside the body via a port or incision. For example, in some embodiments, the device is sized such that when the deformable leaf is in a cylindrical first configuration, the deformable plate may be sized to fit through a trocar. Devices of the invention may also be sized and configured for laparoscopic surgery performed through an opening in the abdominal wall or other parts of the body. For example, the shaft and deformable leaf, when in a cylindrical first configuration, may be sized to fit in a trocar, cannula, and/or incision. In some embodiments, the shaft and the deformable leaf, when in the cylindrical first position, are sized to fit through a trocar. The proximal end of the deformable leaf may further be configured to guide the deformable leaf back into the trocar after deployment of the sheet-like implant. For example, the deformable leaf may have ramped edges configured to push the leaf into the cylindrical first configuration when the leaf is pulled into the bore of a cannula. In some embodiments, the proximal end of the deformable leaf may include one or more sloped edges on the proximal end to help feed the deformable leaf back into a cannula, trocar, or incision after deployment.

In some embodiments, the angled edges of the proximal end of the deformable leaf align with an angled edge of the distal end of the shaft to help feed the shaft and deployment plate back through the cannula or incision.

The deformable leaf may include at least one opening which, upon deployment of the graft to tissue, may be used to access the graft for attachment of the graft to the tissue by a separate attachment device. In some embodiments, the deformable leaf includes one or more openings for accessing the sheet-like implant to secure the sheet-like implant to tissue. For example, the sheet-like implant may be retained on the first surface of the deformable leaf such that a portion of the implant material is accessible through an opening in the deformable leaf. In some embodiments, the opening is shaped as a circle, or as a rectangle. The one or more openings may be any shape that allows the placement of a surgical fastener through the opening into the implant material and into the underlying tissue. In some embodiments, the one or more openings are sized for a tack, staple, or suture. The surgical fastener, for example a tack or staple, may be applied using a separate device configured for surgical fastening or suturing.

The deformable leaf may be flexibly attached to the shaft of the device to allow for flexibly placing the implant material onto tissue. In other embodiments, the deformable leaf may be rigidly attached to the shaft. The shaft may include a beveled edge at the distal end of the shaft to aid in pulling or pushing the device through an incision or cannula.

Figure 37:
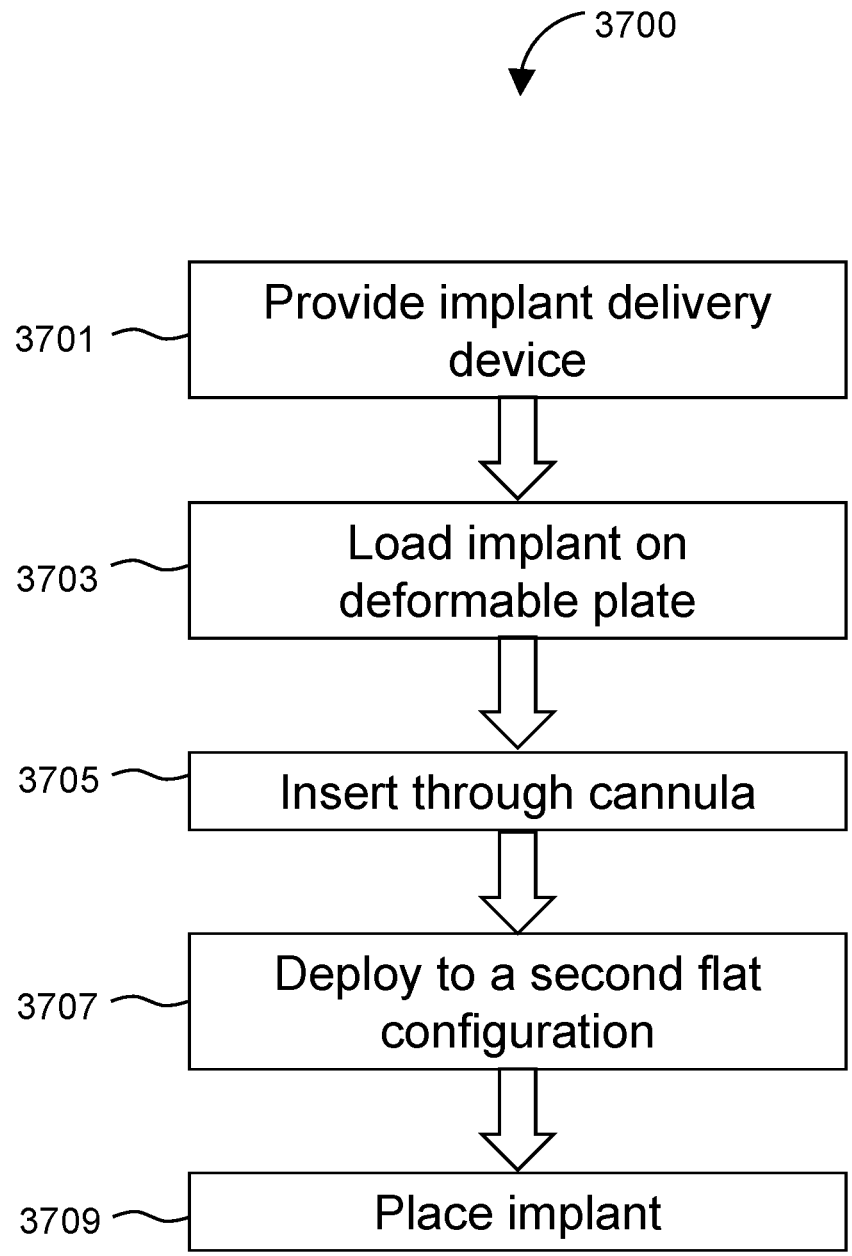
FIG. 37 shows steps of a method.

FIG. 37 shows steps of a method 3700 for deploying a sheet-like material to a surgical repair site. The method 3700 includes providing 3701 an implant delivery device as disclosed herein. The device may include a handle, a shaft extending from the handle, a deformable plate attached to a distal portion of the shaft, such that the deformable plate comprises a first surface and a second surface obverse to the first surface. The device may also include a trigger on the handle and a retainer mechanism on the deformable plate. The trigger may be operably linked to the deformable plate to pull the deformable plate between a cylindrical first configuration and a flat second configuration. The retainer mechanism may be operable to releasably hold a sheet-like orthopedic implant against the first surface.

In embodiments of the method, when the device is ready, e.g., removed from its packaging, the deformable delivery plate is at rest, in the curled closed position. The method includes opening the deformable plate, by operating the trigger, thereby exposing the delivery surface and retainer mechanism (e.g., clip) and positioning the implant (e.g., an approximately 2.5 cm square of collagen) on the surface, thereby loading 3703 the implant.

The implant may be biologic or synthetic. Tissue grafts may originate from different types of organic material, including bone, tendons, skin, nerves, heart valves and cartilage, and may be categorized as autograft, allograft, or xenograft. An autograft is tissue moved from one location within the body to another, for example the use of the semitendinosus tendon from a patient to repair an anterior cruciate tendon in the same patient. Allografts are tissue donated from one person to use for reconstruction or replacement in another person, most often through the tissue donation process. For example, the graft may be skin with all cells except for collagen removed, sourced from a donor or the patient. A collagen graft may be used on a damaged tendon to facilitate regrowth and thickening of the damaged tendon. Xenografts are tissue acquired from a non-human source, usually a pig or cow.

Synthetic and semi-synthetic grafts are composed of non-tissue materials that are biocompatible and allow tissue to grow around them to facilitate healing and induce the formation of new tissue at the repair site. As an example, surgical mesh implants may be made from biocompatible synthetic materials or from animal tissue. Devices and methods of the invention contemplate using any sheet-like implant material.

With the implant loaded 3703 onto the device, the method may include relaxing the trigger, which de-tensions the wire extending through the shaft and around the head. The material of the deformable plate returns to its cylindrical conformation, curling the implant closed within the now-cylindrical deformable plate. With the implant loaded, the method may include inserting 3705 the closed plate with implant through a cannula in an incision in the shoulder of the patient, specifically inserting 3705 the deformable plate or leaf (while it is in a cylindrical first position) and a portion of the shaft into a body cavity to a surgical repair site Optionally, the method includes viewing the delivery plate on camera and deploying 3707 the deformable plate to a second, substantially flat position. This is accomplished by operating the trigger to open the delivery plate. Further, the method may include positioning the implant over and onto the repair site before attaching the implant to the repair site.

The method 3700 includes placing 3709 the sheet-like implant material such that the sheet-like implant material is in contact with the tissue and attaching the implant to repair site. Attachment of the implant may include using a separate device to partially fix the sheet-like implant to tissue by accessing the tissue through an opening within the deformable plate. The method 3700 includes removing the deformable plate, which may involve by pushing the deformable plate forward to release the sheet-like material from the retaining mechanism and/or lifting the implant delivery device off of the implant. The device is curled back closed and withdrawn from the surgical site back through the cannula. Thus delivery methods 3700 preferably include loading 3703 a sheet-like implant onto the device and then include inserting 3705 the deformable plate in a cylindrical first position and a portion of the shaft into a body cavity to a surgical repair site and deploying 3707 the deformable plate to a second, substantially flat position, and placing 3709 the sheet-like implant material in contact with the tissue to be repaired.

The method may be used for repairing a cylindrical body, for example a vessel, tendon, ligament, or elongated cell. In particular, the method may be used to place the implant material on a blood vessel to perform a vascular anastomosis procedure or to fix an aneurism. The method may include providing an implant delivery device having a handle with a trigger, a shaft extending from the handle, a deformable plate attached to a distal portion of the shaft, the deformable plate comprising at least a first delivery surface with a retainer mechanism for holding a sheet-like implant against the delivery surface, wherein when the deformable plate is at rest, the deformable plate is in a first cylindrical configuration.

The implant material may be positioned on the delivery surface of the deformable plate as described above, by operating the trigger to move the deformable plate to the second flat configuration to expose the delivery surface and position the implant on the surface. The deformable plate may then be returned to the first cylindrical configuration by relaxing the trigger, such that the implant is closed within the deformable plate in the first cylindrical configuration.

The deformable plate and implant may then be inserted through a cannula in an incision to a surgery site, where the deformable plate may be deployed to the second flat position at the surgery site. Once deployed the implant may be positioned on the outside surface of the cylindrical body at the surgery site. Once positioned, relaxing the trigger to returns the deformable plate to the first cylindrical configuration, thereby curling the implant around the outside surface of the cylindrical body. The implant may then be attached to the repair site and the deformable plate removed from the implant. The deformable plate, still in the first cylindrical configuration may then be withdrawn out of the surgical site back through the cannula.

The deformable plate may comprise a plurality of parallel channels in a second surface, obverse to the first surface, that operate as a living hinge allowing the deformable plate to be pulled from the cylindrical first configuration to the flat second configuration. As noted, the deformable plate may assume the first cylindrical configuration at rest and pressing the trigger pulls the plate to the flat second configuration. The trigger may smoothly and progressively move the deformable plate between the first cylindrical configuration and the second flat configuration. In embodiments, the device comprises a wire extending from the trigger and through a loop channel within the deformable plate, wherein tensioning the wire by the trigger pulls the deformable plate from the first cylindrical configuration to the second flat configuration.

Figure 38:
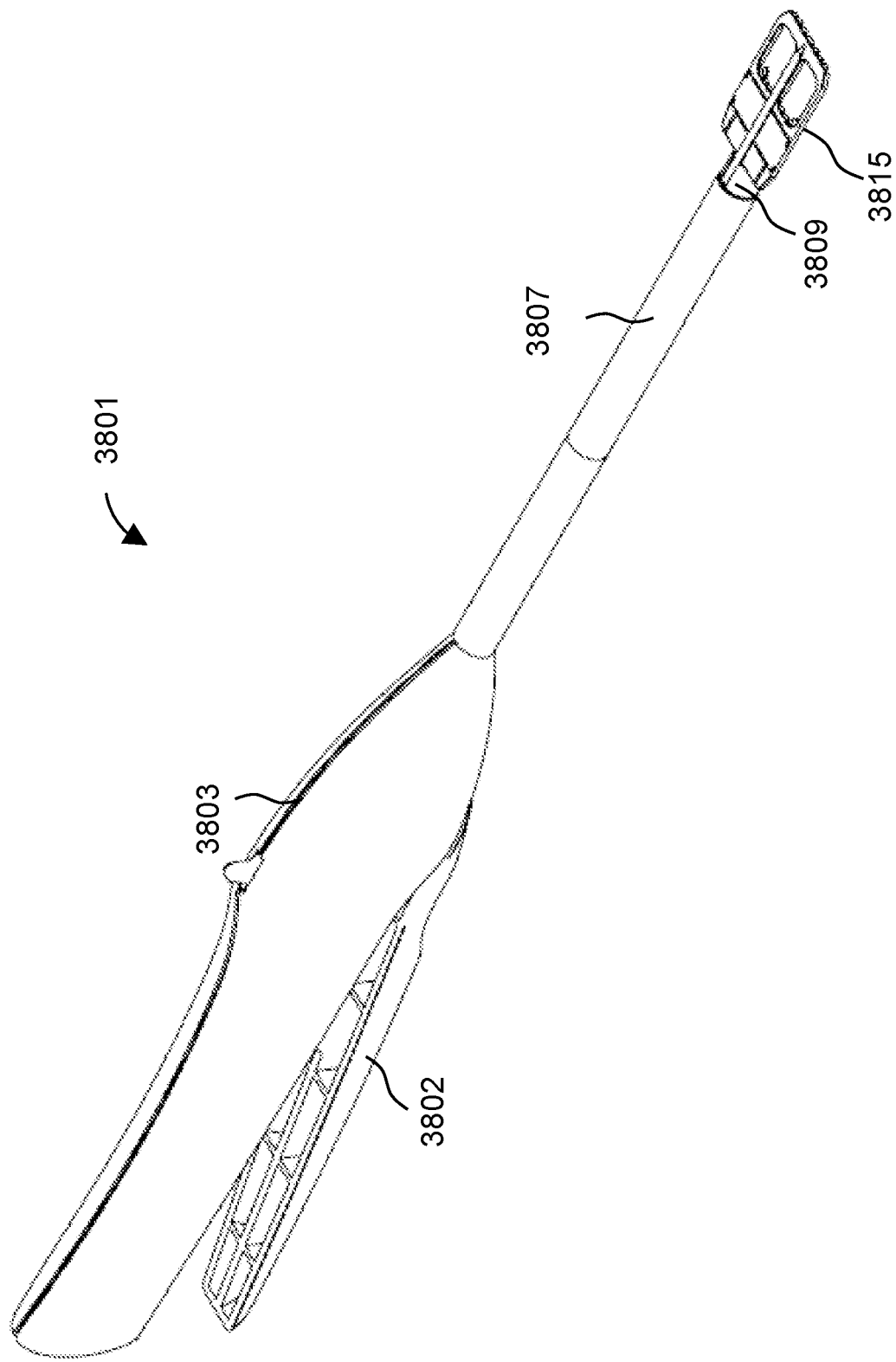
FIG. 38 shows an implant delivery device.

FIG. 38 shows an implant delivery device 3801 that includes a handle 3803, a shaft 3809 extending from the handle, and a deformable plate 3815 carried on a distal portion of the shaft. There is a trigger 3802 on the handle 3803 as well as an insertion sleeve 3807 positioned over the shaft 3809.

Figure 39:
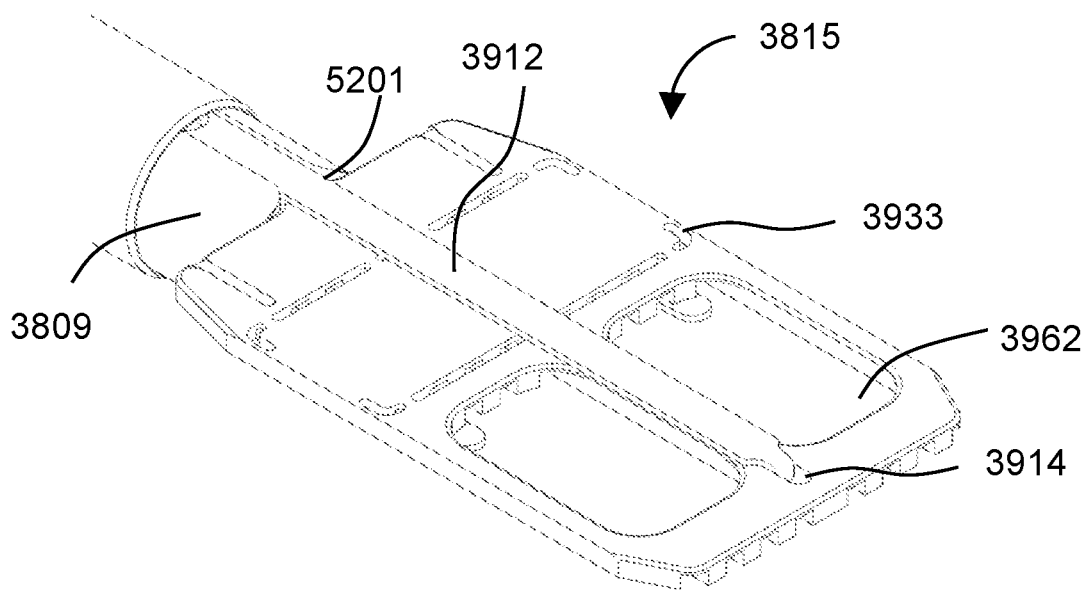
FIG. 39 shows a back side of a deformable plate.

FIG. 39 shows a back side of the deformable plate 3815. The device 3801 may include a reinforcing backbone 3912 attached to the shaft and extending from a proximal end of the deformable plate 3815 toward a distal end of the deformable plate. The backbone 3912 may be attached to the distal end of the deformable plate via a slot 3914 such that the backbone is slidable in the slot in response to movement by the flexible section 5201. As shown in further detail below, the flexible section 5201 allows the deformable plate 1815 to bend off-axis with respect to the shaft 3809. The reinforcing backbone 3912 allows the device 3801 to be used multiple times without breaking and assists in returning the deformable plate to the rest position. Also, as shown, the deformable plate may include one or more openings 3962 through which a surgical fastener may be delivered through the sheet-like implant.

Figure 40:
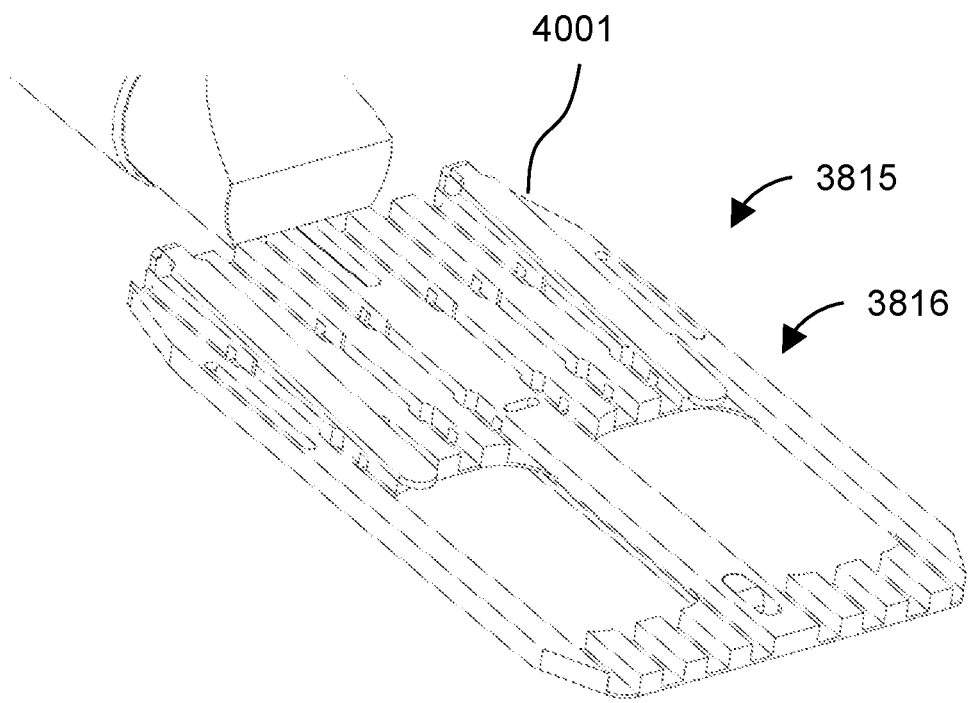
FIG. 40 shows a first surface of the deformable plate.

FIG. 40 shows a first surface 3816 of the deformable plate 3815. The plate 3815 includes a retainer mechanism 4001 such as one or more clips on the deformable plate, the retainer mechanism 4001 operable to releasably hold a sheet-like implant 4115 against the first surface 3816. As shown, the deformable plate comprises a plurality of parallel channels on the first surface that operate as a living hinge 4121 allowing the deformable plate to be pulled from the flat first configuration to the substantially cylindrical second configuration.

The depicted embodiment operates by having the plate 3815 be substantially flat when at rest. Squeezing the trigger 3802 pulls the plate 3815 into a substantially cylindrical shape. Another depicted feature of the device 3801 is the insertion sleeve 3807, which allows the device to be used with out a separate cannula or trocar.

Importantly, whether the plate is flat versus cylindrical at rest and the insertion sleeve versus a separate trocar or cannula are independent features. Any device of the disclosure may have any combination of features shown herein. Thus, to be clear, the disclosure absolutely includes an implant delivery device with a plate that is cylindrical at rest and in which the device includes an insertion sleeve over the shaft. Similarly, the disclosure also includes devices in which the plate is flat at rest and the shaft 3809 is not housed in any insertion sleeve.

In preferred embodiments of the device 3801, the trigger can be moved to, and held in, a plurality of different positions between a rest position and fully-closed position to thereby hold the deformable plate in a respective plurality of different configurations between the flat first configuration and the substantially cylindrical second configuration.

Figure 41:
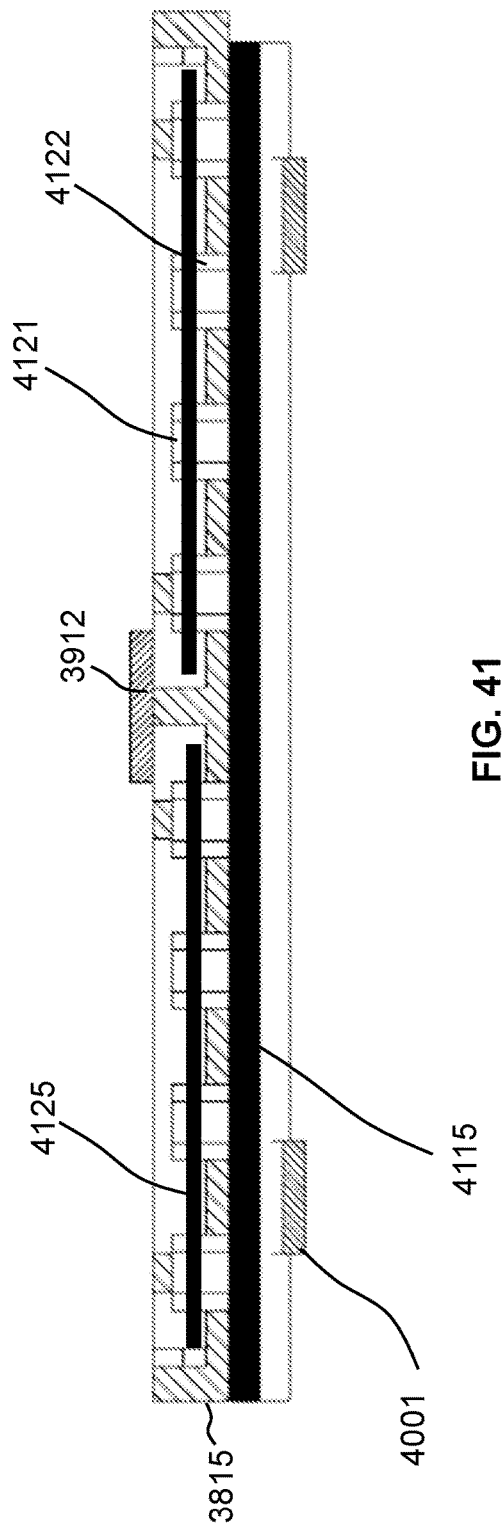
FIG. 41 shows the deformable plate in a flat first configuration.

FIG. 41 shows the deformable plate 3815 in a flat first configuration. As shown, the plate 3815 is carrying an implant 4115 in retainer mechanism 4001.

Figure 42:
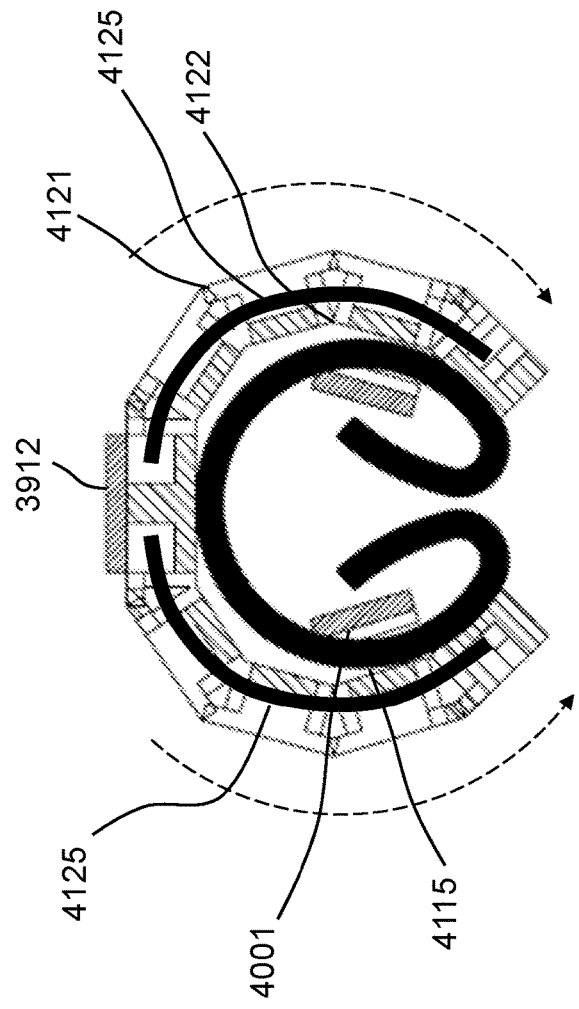
FIG. 42 shows the plate in cylindrical second configuration.

FIG. 42 shows the deformable plate 3815 in a substantially cylindrical second configuration. The plate 3815 preferably includes limiters 4122 that prevent deformation beyond the depicted first or second configurations. The deformable plate 3815 may include a deployment wire 4125 extending from the trigger 3802 and through a loop channel 3933 within the deformable plate 3815. Tensioning the wire 4125 by the trigger 3802 pulls the deformable plate 3815 from the flat first configuration to the substantially cylindrical second configuration. Note that when the sheet-like implant is in the cylindrical second position, lateral edges of the sheet-like implant are curled inward. It has been found that the depicted geometry of the head promotes this shape for the implant 4115, which has been found to aid in secure and useful delivery to a surgical site.

Figure 43:
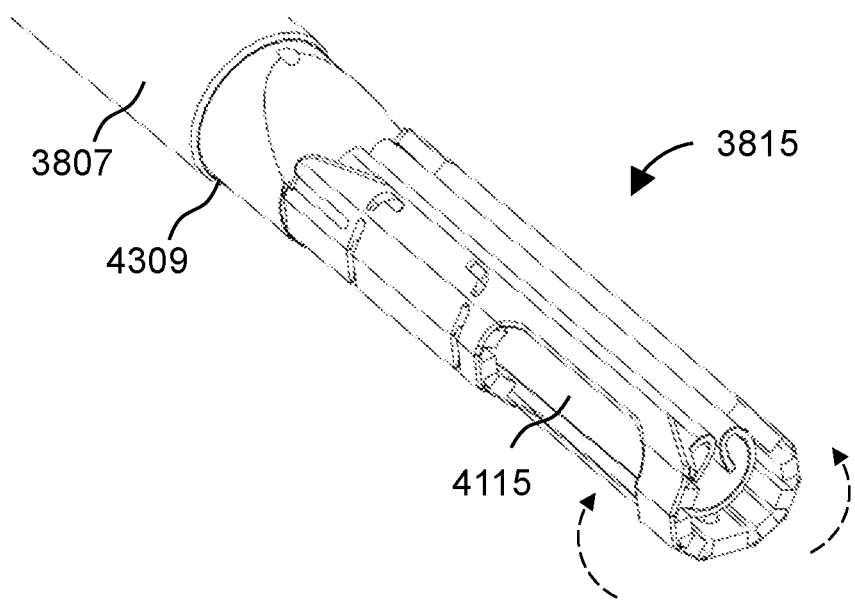
FIG. 43 shows the plate being curled.

FIG. 43 shows the plate 3815 being curled so that the plate can be drawn into and covered by the sleeve 3807. The insertion sleeve 3807 is positioned on the shaft and slidable on the shaft from a proximal to a distal portion of the shaft. Preferably the sleeve 3807 has a beveled or tapered face 4309 to promote smooth insertion into a surgical incision.

Figure 44:
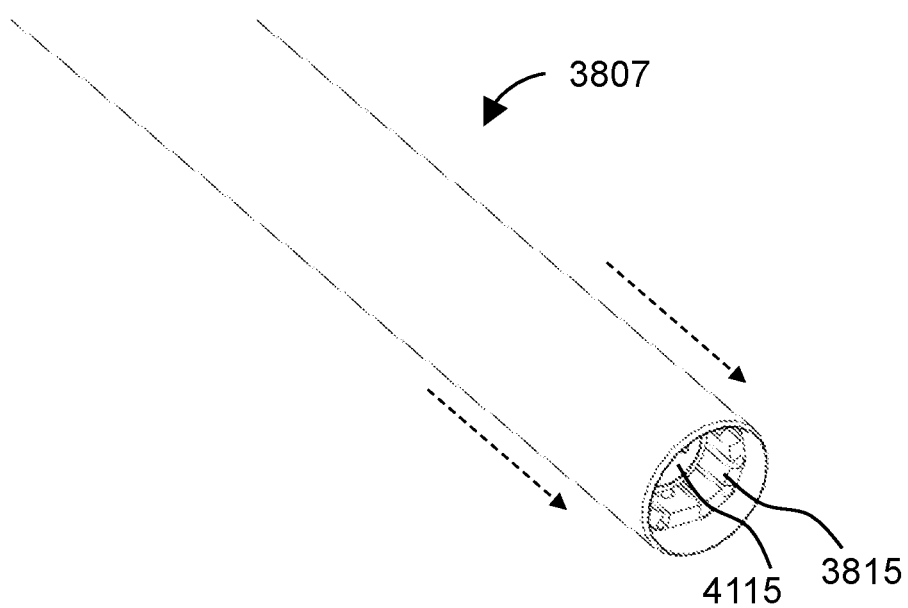
FIG. 44 illustrates the sleeve in the distal position.

FIG. 44 illustrates the sleeve 3807 in the distal position, covering the deformable plate while the deformable plate is in the substantially cylindrical second configuration.

FIG. 38 shows an implant delivery device with a deformable plate or leaf for deployment of a graft that is normally in an open position. FIG. 40 shows that the plate 3815 has a surface 3815 to which a graft or implant may be temporarily fixed, allowing the device to carry the implant to a surgery site such as damaged tissue. FIG. 41 shows a mechanism (wire system) to deform or compress the plate (and the attached implant) to allow the plate and implant to be passed through a surgical incision.

FIG. 40 shows a graft attachment mechanism 4001 that includes one or more clips on and over a surface 3816 of the plate 3815. As shown, each clip may have an elongated arm with an attached hinge first end and an unattached compressing clip second end.

Figure 46:
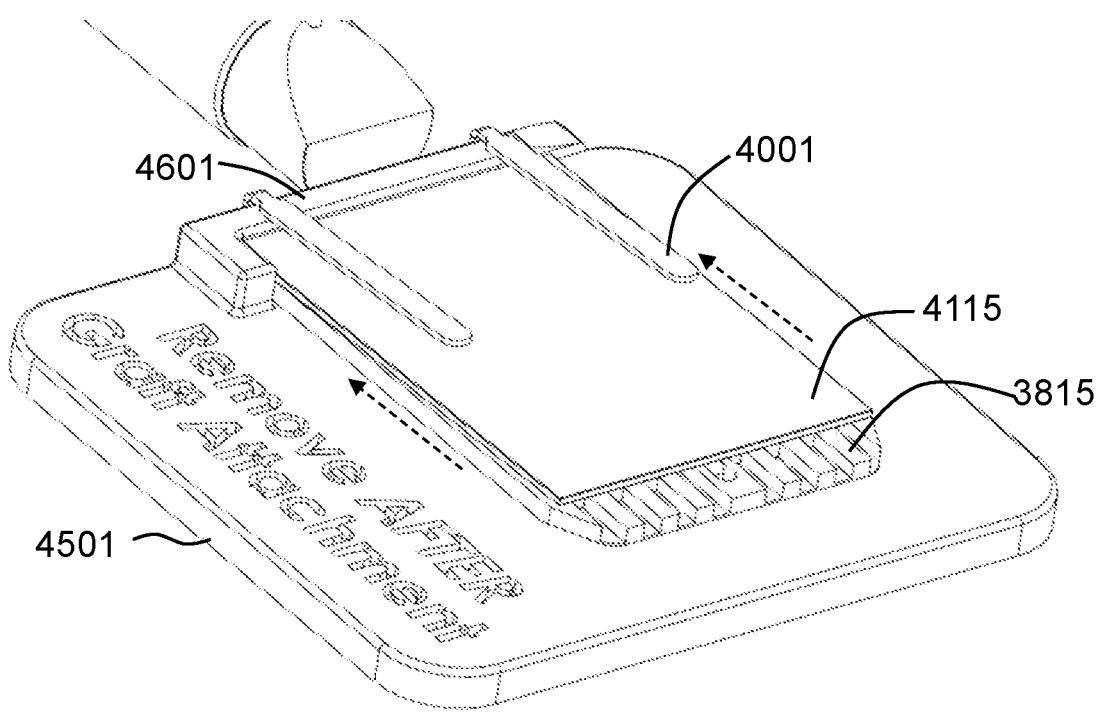
FIG. 46 shows a pin of the loading card.
Figure 53:
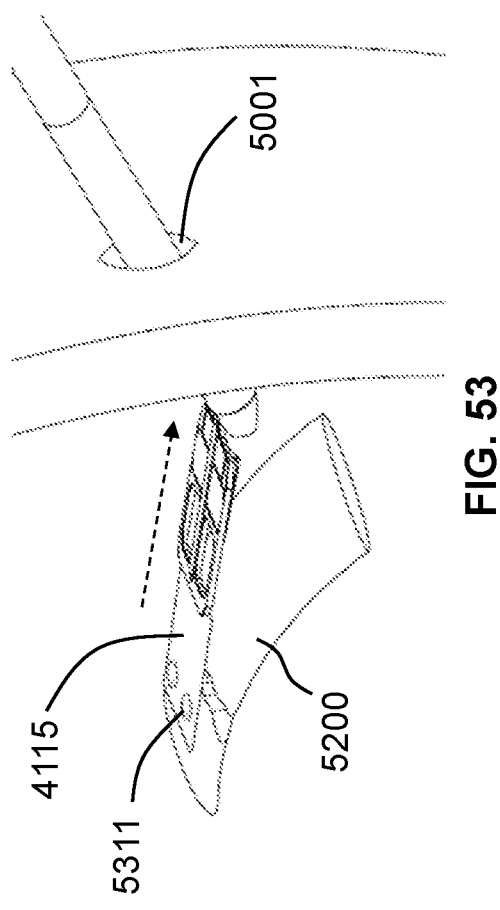
FIG. 53 shows the step of removing the deformable plate from the implant.

FIG. 46 shows that the first end is elastically mounted to the plate, allowing the elongated arm to be deformed away from the plate, allowing the compressing clip end to be lifted off of the surface of the plate, which allows an implant to be slid into position on the plate. While various embodiments are disclosed and included within the scope of the disclosure, preferred embodiments of the graft attachment mechanism include at least a pair of arms that extend substantially parallel to an axis of a shaft of the device. The proximal end of each clip is elastically mounted to the surface of the plate while the distal end of each clip provides a compressing clip mechanism. FIG. 17 shows clips that may include a lever 501 extending from one end allowing a user to squeeze the lever to open the distal end. FIG. 40 shows a preferred embodiment, in which the pair of clips are attached at a proximal portion of the plate and open towards the distal direction. FIG. 53 shows that when an implant is held by the clips and has been anchored or attached to tissue, the implant delivery device may be drawn in a proximal direction to pull the device (and plate) off of the implant, release the implant, and leave the implant in position on the tissue after the delivery device is removed from the site.

One feature of the disclosure is a loading card or plug that may be positioned on, and/or carried by, an implant delivery device. The loading card is generally a disposable piece that volumetrically biases an implant retainer into an open or receiving position, facilitating the easy manual loading of an implant onto the device.

Figure 45:
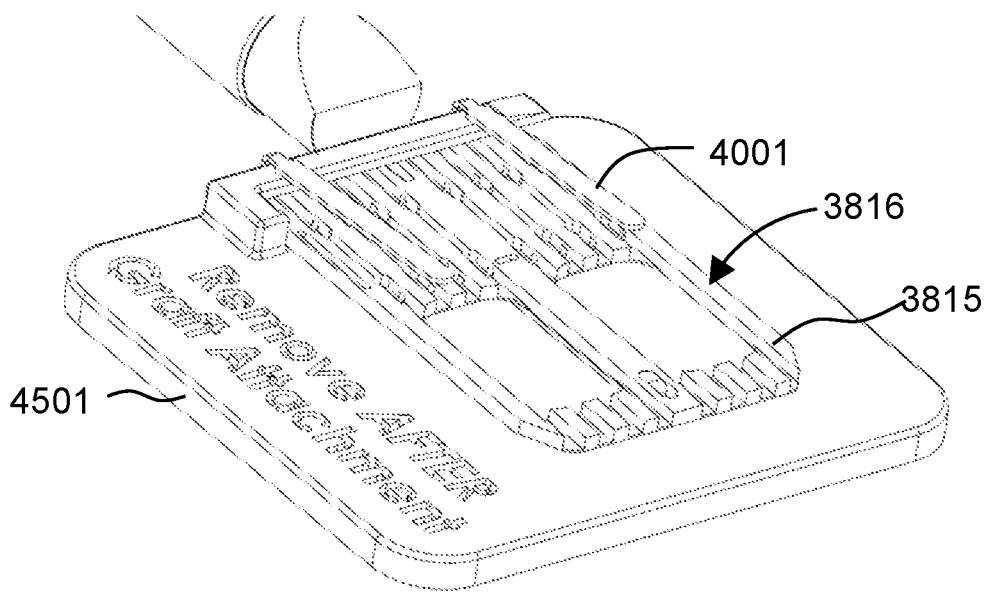
FIG. 45 shows a loading card.

FIG. 45 shows a loading card 4501 that may be provided with any device of the disclosure. Preferably, the loading card is removably attached to the deformable plate 3815. The retainer mechanism 4001 on the deformable plate 3815 may be spaced apart from the first surface 3816 of the deformable plate 3815 by the loading card 4501.

Figure 47:
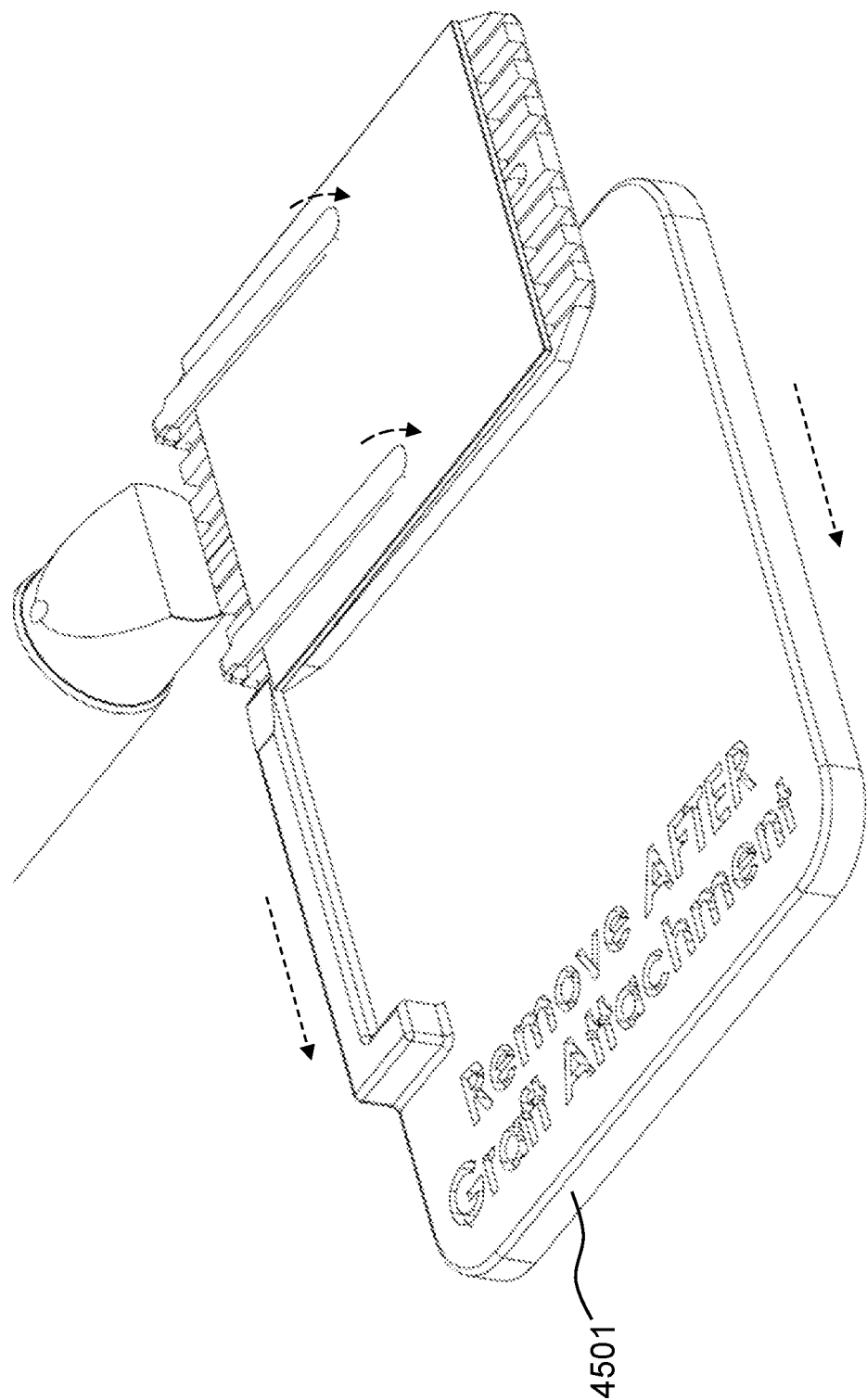
FIG. 47 shows use of a loading card.

FIG. 46 shows that the loading card may include a loading pin 4601 positioned to hold the retainer mechanism 4001 open for positioning of the sheet-like implant 4115 upon the first surface 3815 of the deformable plate while the loading card is attached to the deformable plate. FIG. 47 shows use (e.g., removal for disposal of) the loading card 4501. As shown, the loading card 4501 is configured to slide the loading pin from the retainer mechanism and release the loading card from the deformable plate while leaving the sheet-like implant retained upon the deformable plate 3815. A feature of the loading card is that an implant delivery device may be shipped with the loading card in place (e.g., as shown in FIG. 45). In surgery, a clinician removes the sterile device from packaging and manually loads in implant (see FIG. 46). Because the loading card 4501 holds the retainer mechanism 4001 in an open position, it is relatively easy to load the implant 4115 onto the plate 3815 without deforming or tearing the implant 4115. Once the implant is loaded, the loading card may be removed (e.g., slide out to the side in the example shown in FIG. 47). FIG. 45 shows embodiments of the disclosure with a loading card 4501. While various shapes, materials, or features of a loading card are within the scope of the disclosure, the loading card, generally, refers to a separate piece that is provided pre-positioned within a graft attachment mechanism that biases the graft attachment mechanism into a graft receiving position during and until placement of an implant or graft within the mechanism. The loading card may be disposable, sterile card or member that simply holds the mechanism, e.g., one more clips, into at least a partially open shape. For example, where the graft attachment mechanism includes at least a pair of clips open, e.g., towards a distal end of the device, the loading card maybe a small fiberboard or polymer card that is provided, siting within the clips, holding the clips at least a little bit open. A clinical can load the device by sliding an implant or graft under the clips. The loading card holds the clips up and off of a surface of the deployment plate, so that the compression clip ends of the arms of the clips do not tear, damage, or interfere with the implant. Once the implant is positioned on the plate, the loading card may be slid out of (e.g., sideways from the arms of) the clips. The clips then compress onto the implant, holding the implant in position on the deployment plate. The loading card may simply be thrown away.

Other features of the disclosure may be included an embodiments herein.

FIG. 48 shows an insertion sleeve 3807 positioned over the shaft 3809 at its proximal-most position. The device 3801 may include limiters 4911, 4912 or stops to allow the sleeve to only slide to the relevant positions.

FIG. 49 shows the insertion sleeve 3807 being slid over the shaft 3809 between a back sleeve limiter 4911 positioned at the proximal end of the shaft and a front sleeve limiter 4912 positioned at the distal end of the shaft such that the insertion sleeve uncovers the deformable plate by sliding of the insertion sleeve backward in a direction from the front sleeve limiter toward the back sleeve limiter and covers the deformable plate by sliding of the insertion sleeve forward in a direction from the back sleeve limiter to the front sleeve limiter.

The device 3801 is useful for delivering an implant 4115 to a surgical site, e.g., within a joint, via arthroscopic or keyhole surgery. FIG. 50 through FIG. 53 illustrate a method for tissue repair. The method includes providing an implant delivery device having a handle with a trigger, a shaft extending from the handle, a deformable plate attached to a distal portion of the shaft, the deformable plate comprising at least a first delivery surface with a retainer mechanism for holding a sheet-like implant against the delivery surface. When the deformable plate is at rest, the deformable plate is in a first flat configuration. The device may optionally include an insertion sleeve positioned on the shaft and slidable from a proximal to a distal position of the shaft such that the insertion sleeve covers the deformable plate when the deformable plate is in a substantially cylindrical second configuration. The device may also optionally include a loading card releasably attached to the deformable plate.

The method includes loading a sheet-like implant 4115 onto the deformable plate 3815. The loading step may optionally use the loading card and may involve positioning the implant 4115 onto the delivery surface held by the retaining mechanism then removing the loading card from the deformable plate. In certain embodiments, the plate is flat at rest. The method may include operating the trigger to move the deformable plate to the second substantially cylindrical configuration. The method may include inserting the cylindrical head 3815 and device shaft 3809 through a trocar or cannula in a surgical incision. In the depicted embodiments, the device includes an insertion sleeve. The insertion sleeve may be slid in a distal direction along the shaft to cover and enclose the deformable plate.

Figure 50:
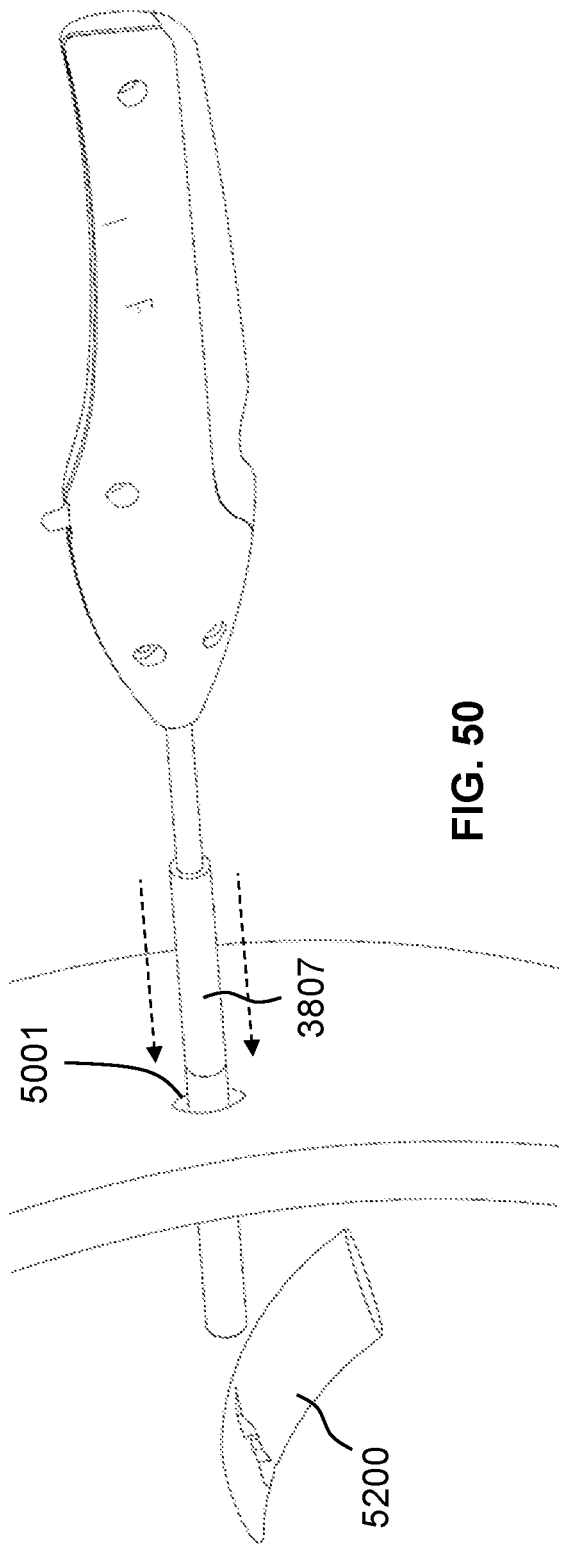
FIG. 50 shows the device with the sleeve in the distal position.

FIG. 50 shows the device with the sleeve 3807 in the distal position, covering the deformable plate. As shown, the method may include inserting the deformable plate and implant through an incision 5001 to a surgery site to attach the implant to damaged tissue 5200. For embodiments using an insertion sleeve, the method may include sliding the insertion sleeve backward toward the proximal end of the shaft to thereby uncover the deformable plate.

Figure 51:
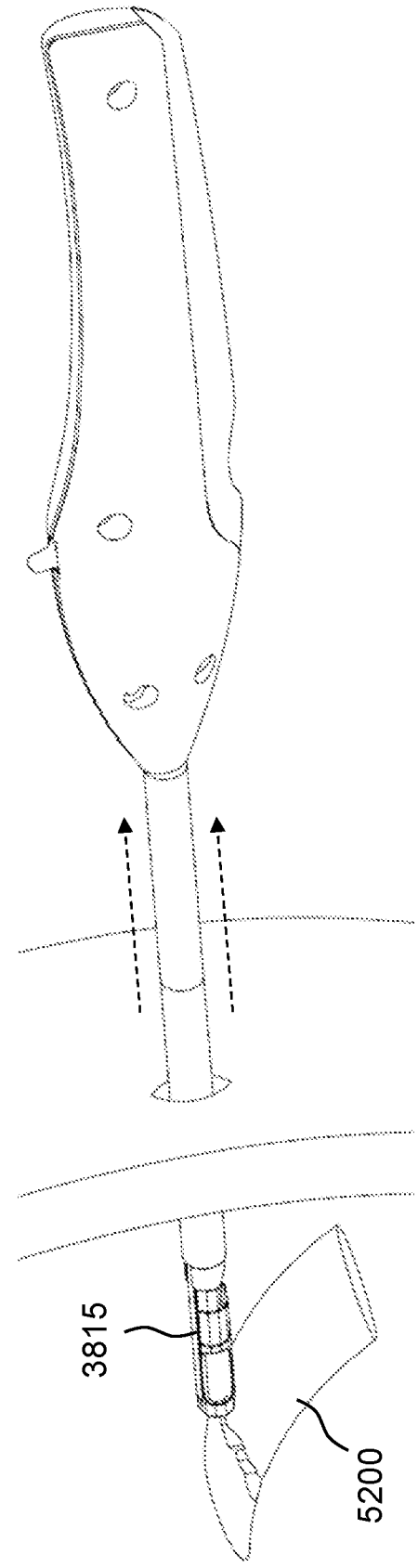
FIG. 51 shows the device with plate adjacent tissue in need of repair.

FIG. 51 shows the device with plate 3815 adjacent the tissue 5200 in need of repair.

Figure 52:
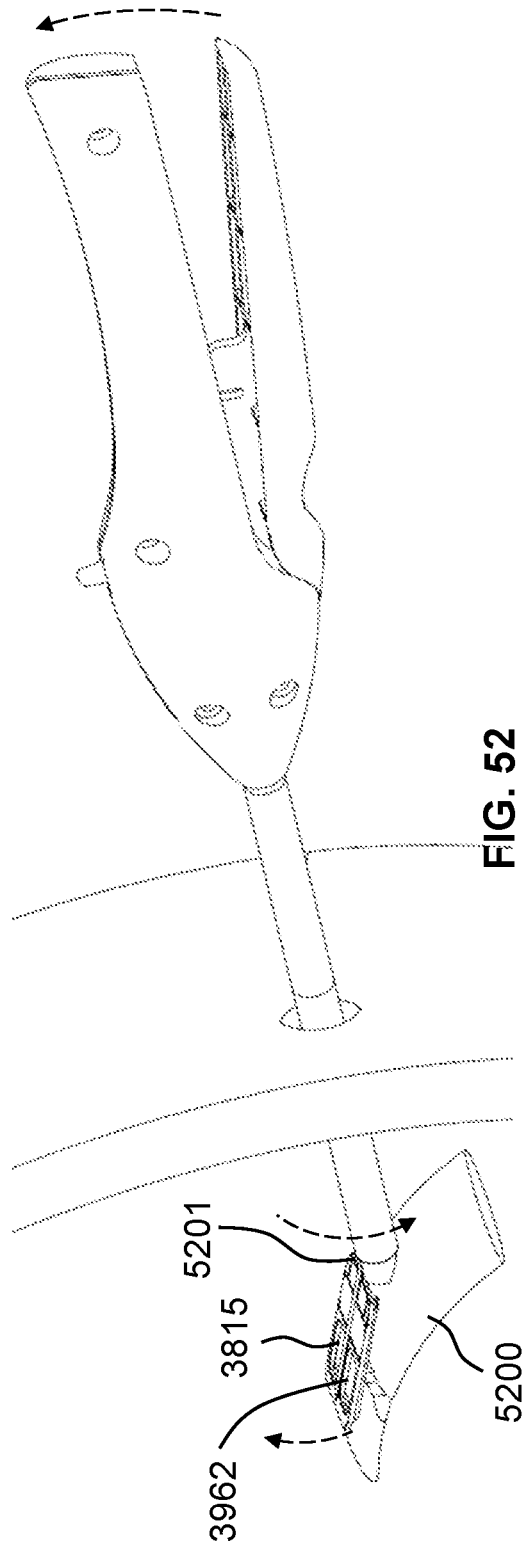
FIG. 52 shows the step of deploying the deformable plate.

FIG. 52 shows the step of deploying the deformable plate 3815 to the first flat position at the surgery site adjacent the tissue 5200. The method includes positioning the implant on tissue at the surgery site and attaching the implant to the repair site. Using arthroscopic surgery tools, a separate suture, clip, or anchor delivery device may be brought in to deliver a fastener (e.g., suture or anchor) through the holes 3962 in plate 3815, thereby attaching the implant 4115 to the tissue 5200. As shown, the deformable plate 3815 is connected to the shaft via a flexible section 5201 that allows the plate to be angled away from the shaft and aligned to tissue 5200 during surgery.

FIG. 53 shows the step of removing the deformable plate from the implant. Once the plate is free of the (now attached) implant, the method includes returning the deformable plate to the second substantially cylindrical position and withdrawing the deformable plate out of the surgical site back through the incision. For embodiments that use an insertion sleeve, the method may include sliding the insertion sleeve to cover the deformable plate, e.g., before removing the device 3801 from the incision 5001. FIG. 54 through FIG. 59 show embodiments of an implant delivery device with an insertion sleeve 3807, which may be a substantially tubular or cylindrical member mounted over a delivery shaft of the device. FIG. 48 and FIG. 49 show that the insertion sleeve may be slideable in a proximal and a distal direction along the shaft. By default, the sleeve rest in a proximal position, with the deformable plate extending past a distal portion of the sleeve, with the deformable plate resting in its open, flat position. A clinician can mount a graft or implant onto the deformable plate and then operate the trigger to roll the deformable plate (and graft) into the substantially cylindrical position. The, the insertion sleeve can be slid in a distal direction over the shaft, which draws the delivery plate into the insertion sleeve. Because the deformable plate and the graft (or implant) that it carries are pulled into a substantially cylindrical configuration and drawn into an interior bore of the insertion sleeve, the device can be used in arthroscopic or keyhole surgery by inserting the insertion sleeve through a surgical incision (see FIG. 58). A benefit of the insertion sleeve is that it encloses the graft and deployment plate during surgical access. This protects both the tissue (e.g., around the incision) and the graft during delivery of the graft to the surgical site In certain embodiments, an insertion sleeve on an implant delivery device includes a cap with a profile that aids insertion into an incision.

Figure 54:
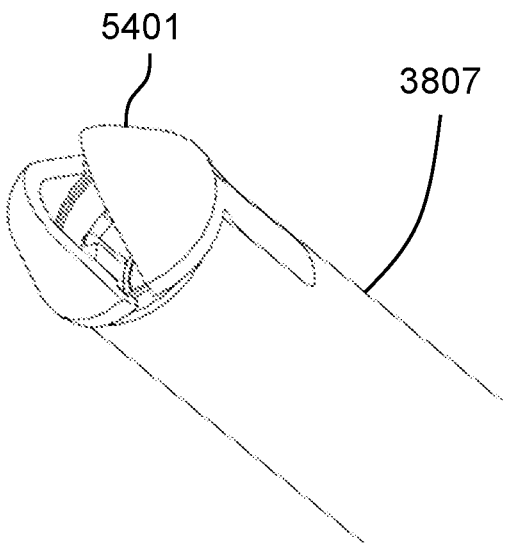
FIG. 54 shows a cap that may be provided at end of the insertion sleeve.

FIG. 54 shows a cap 5401 that may be provided at end of the insertion sleeve 3807.

Figure 55:
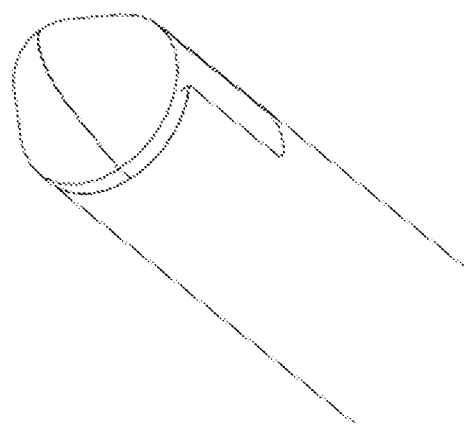
FIG. 55 shows the cap 5401 in a closed arrangement.

FIG. 55 shows the cap 5401 in a closed formation. A feature of the cap 5401 is that transitions between a fully open, an intermediate, and a closed arrangement.

Figure 56:
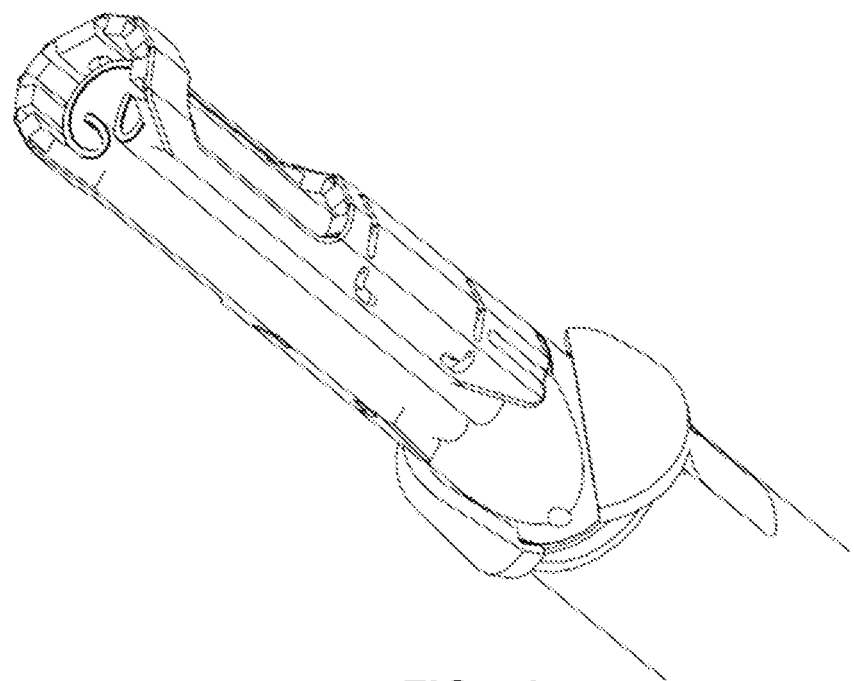
FIG. 56 shows the cap in the fully open arrangement.

FIG. 56 shows the cap in the fully open arrangement with the deformable plate extending therefrom.

Figure 57:
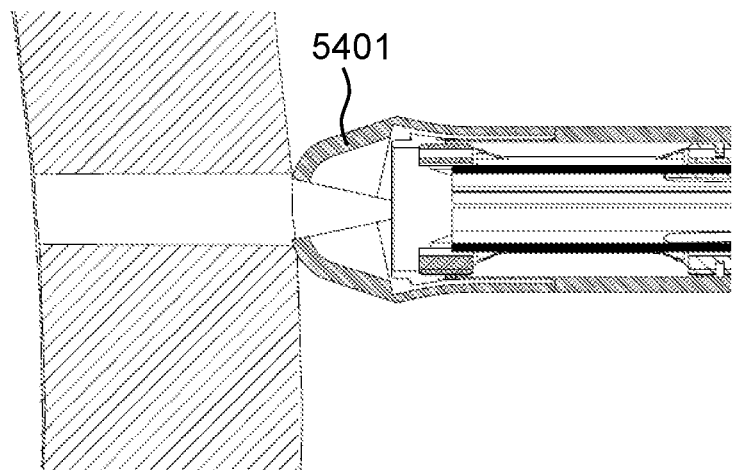
FIG. 57 shows that when no load is applied, the cap remains partially open.

FIG. 57 shows that when no load is applied, the sleeve covers remains partially open. In certain embodiments, this is the rest position for the cap 5401.

Figure 58:
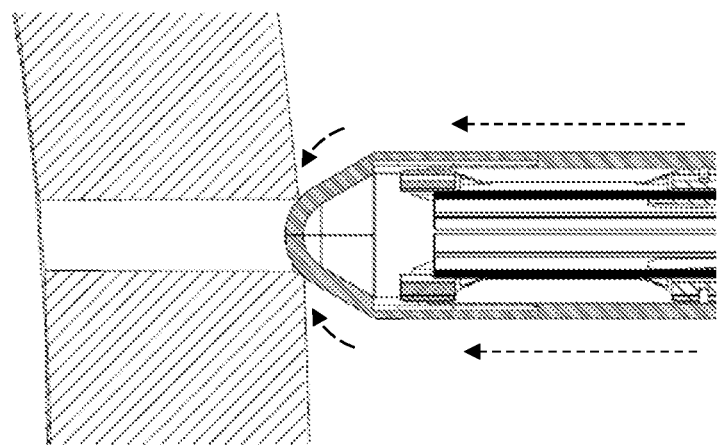
FIG. 58 shows a closed cap, forming a cone.

FIG. 58 shows that, when pushed against the incision edges the sleeve cover (e.g., cap 5401) is closed, forming a cone. A benefit here is that forward pressure, e.g., against or into the incision, squeezes the cap 5401 into the closed arrangement. The cap is tapered (e.g., domed or conical) to promote smooth, atraumatic passage through an incision. The cap 5401 is beneficial to include with versions of an implant delivery device that use an insertion sleeve. As shown, the insertion sleeve may include the cap at the distal end, such that, when the cap is pressed against an incision in tissue, the cap closes to form a cone-shape for insertion of the insertion sleeve through tissue.

Figure 59:
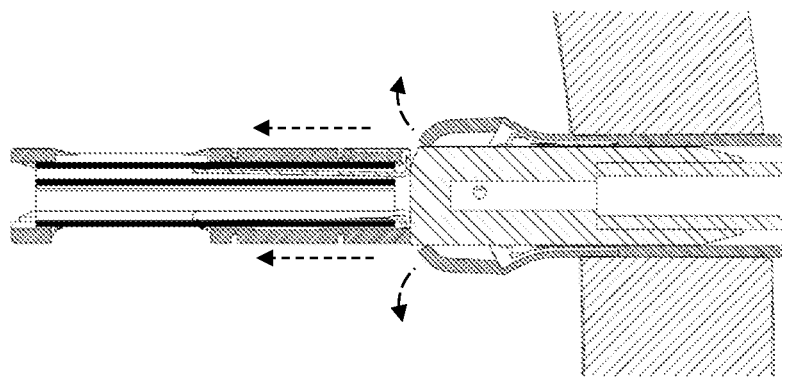
FIG. 59 shows the cap relaxed into an open configuration.

FIG. 59 shows that when the cone completely passes the tissue wall, the sleeve cover (e.g., cap) relaxes back into open configuration and the deployment mechanism can be slid out of the insertion sleeve and into the tissue cavity. The cone-like shape of the cap 5401 helps to expand the incision while the device is pushed forward. The continuous pressure from the tissue keeps the cone closed. Once the insertion sleeve has passed through tissue, the cap is operable to return to an open position and, upon the sliding action of the insertion sleeve toward the proximal end of the shaft, the cap 5401 is drawn over the plate 3815 and shaft, biasing the cap 5401 to the open arrangement.

Other features are within the scope of the disclosure.

As discussed above, an implant delivery device of the disclosure preferably includes a trigger that can be moved to, and held in, a plurality of different positions between a flat and a cylindrical configuration. Specifically, the device may include mechanisms to hold the deformable plate in one of plurality of different configurations between the flat and cylindrical configuration, allowing the clinician to "set" the plate to a certain degree of openness for a moment.

Figure 60:
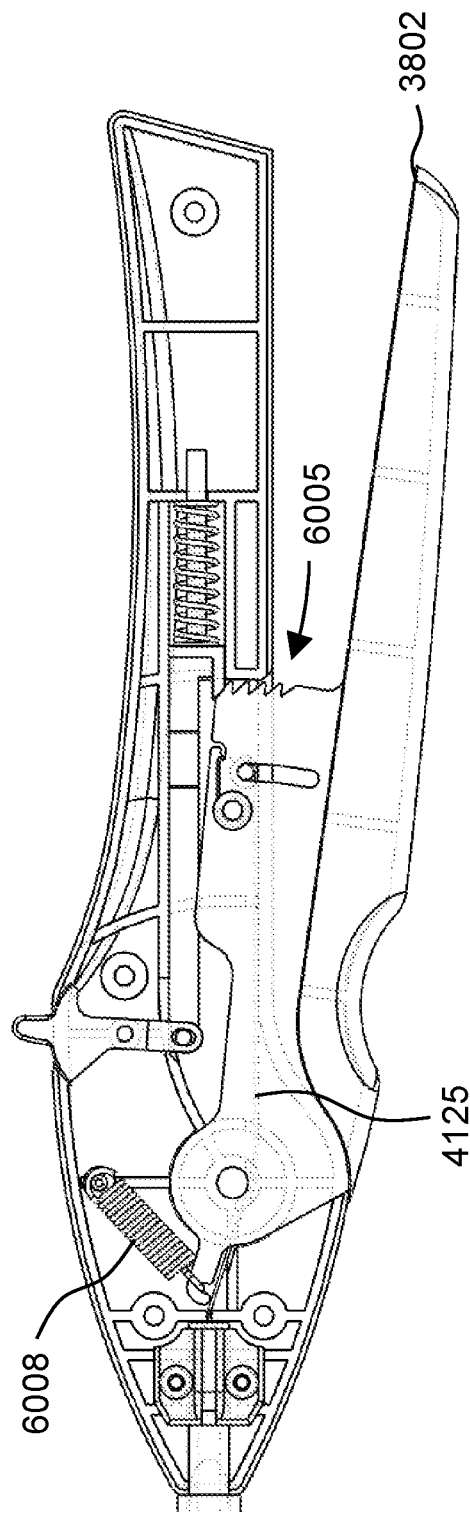
FIG. 60 illustrates a latch.

FIG. 60 illustrates a latch 6005. The latch 6005 may be operably connected to the trigger 3802 and to the wire 4215. The device may include a lever spring 6008 operably connected to the trigger.

Figure 61:
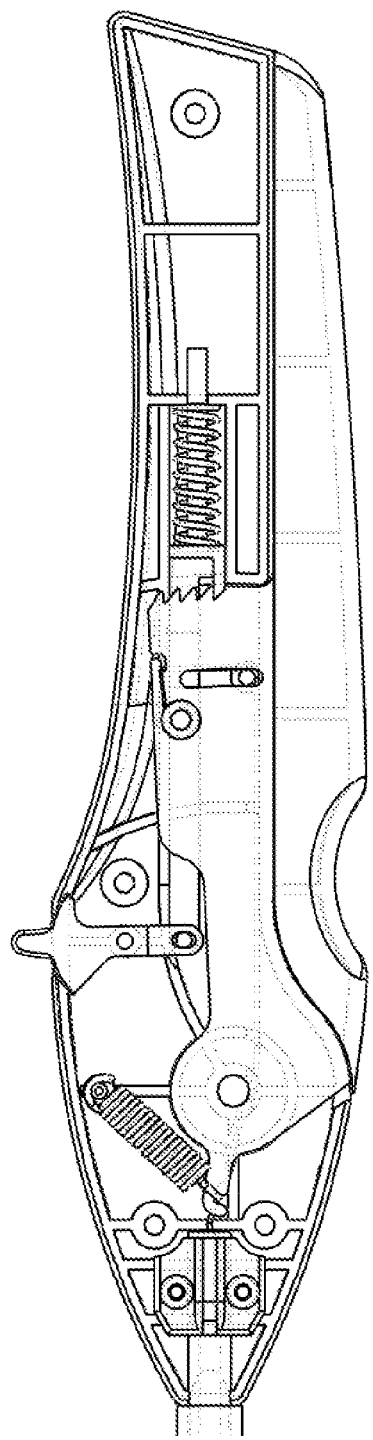
FIG. 61 shows the latch releasably locking the deformable plate in a configuration.

FIG. 61 shows the latch releasably locking the deformable plate in the cylindrical or the flat position (for device 3801 this would be the cylindrical configuration; for device 100, this would be the flat configuration).

Figure 62:
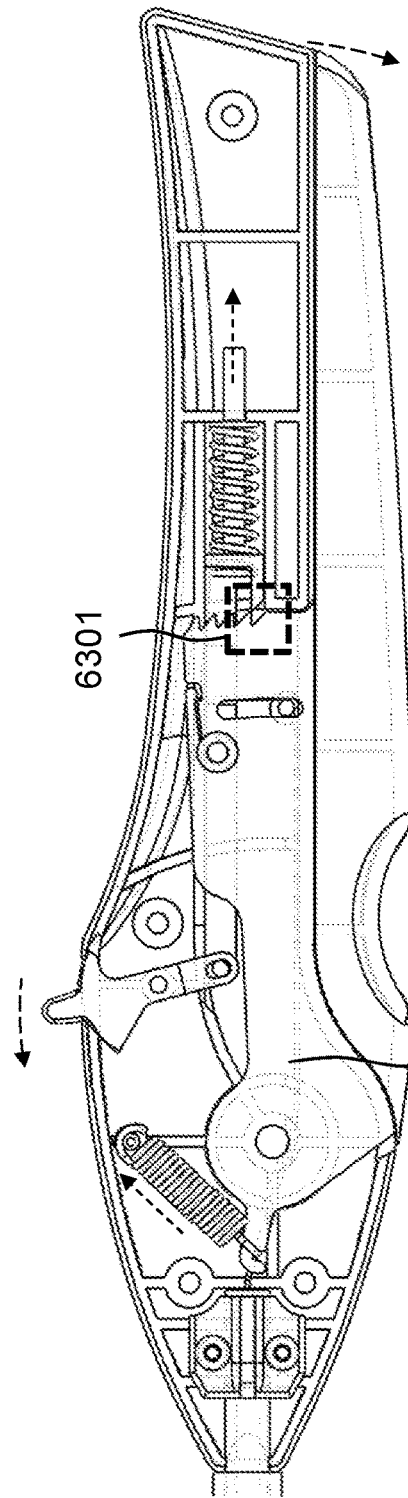
FIG. 62 illustrates the deployment handle.

FIG. 62 illustrates how the deployment handle allows the surgeon to control the tension at the deployment wire 4125, thereby controlling the state of the deployment plate. In the embodiments of device 3801, at the initial idle state, the tension at the deployment wire is minimal, hence, the deployment plate is flat. The trigger piece includes a ratchet face 6301 that is engaged by a slidable pin 6302.

Figure 63:
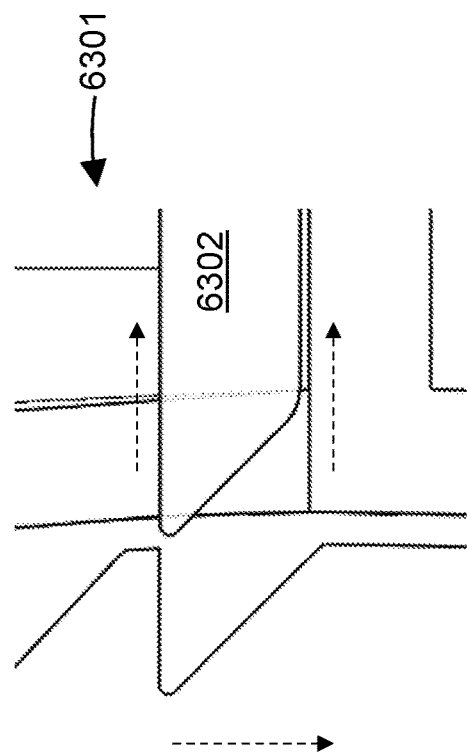
FIG. 63 is a closeup of a pin engaging a slot in the ratchet face.

FIG. 63 is a closeup of a pin 6302 engaging a slot in the ratchet face 6301. Preferably, the first ratchet tooth of ratchet face 6301 is slightly deeper, therefore, the first step of the deployment lever requires a greater amount of force than the other steps, hance preventing accidental pressing of the lever during operation. That is, when the surgeon holds the device 3801 without having yet squeezed the trigger, to begin transitioning the plate 3815 from the flat configuration to the cylindrical configuration requires a harder squeeze (e.g., more force) that is required for the continued actuation of the trigger. This mechanism was discovered to be preferred by users for ergonomically satisfactory performance that promotes patient safety and effectiveness of surgical procedures.

Another feature that may be included in devices of the disclosure is a slider latch mechanism that holds an insertion sleeve in one position along its range of sliding.

Figure 64:
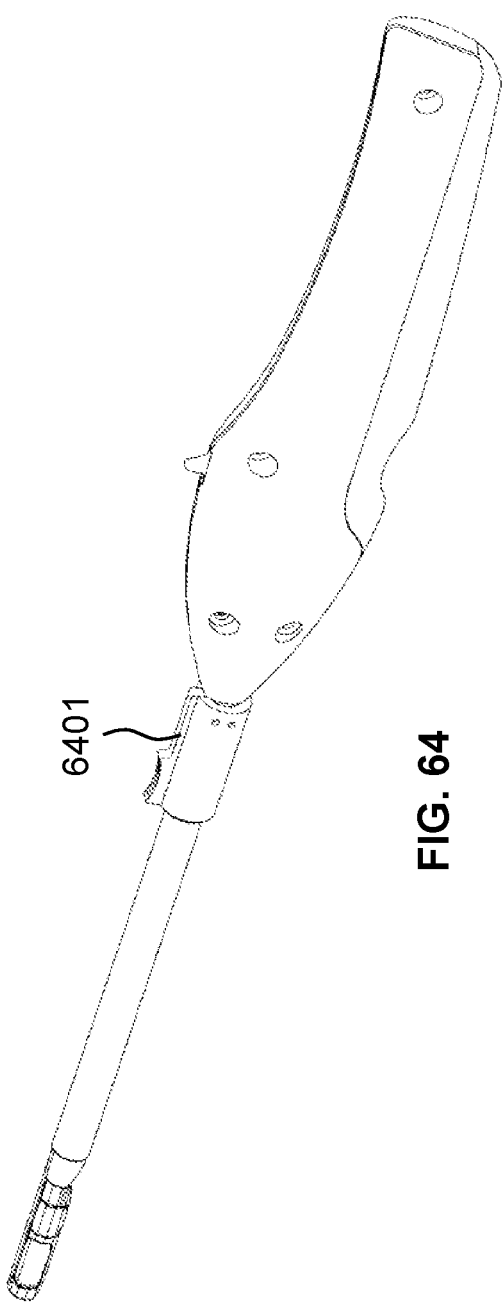
FIG. 64 illustrates a slider latch mechanism.

FIG. 64 illustrates a slider latch mechanism 6401 on the distal end of the handle for releasably retaining the insertion sleeve in a fixed position on the shaft. The mechanism 6401 may be used for reversible fixation of the insertion sleeve to the shaft of the device such that the surgeon could hold the device from the handle during the insertion.

Figure 65:
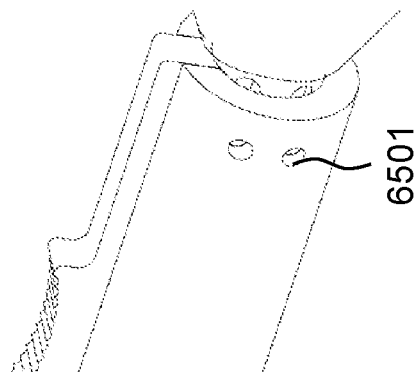
FIG. 65 shows a rotation limiting pin.

FIG. 65 shows that the slider latch mechanism 6401 may include a rotation limiting pin 6501.

Figure 66:
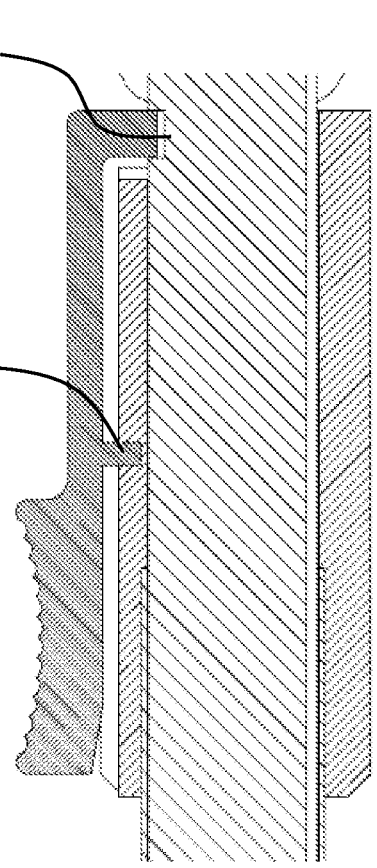
FIG. 66 shows a flexible living hinge.

FIG. 66 shows a flexible living hinge 6601 and a back notch 6602. As shown, a protrusion coupled to the hinge 6601 sits in the notch 6602.

Figure 67:
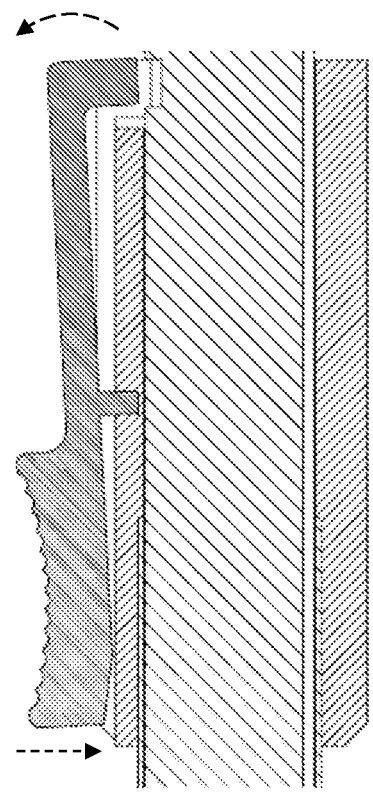
FIG. 67 shows use of a thumb-grip.

FIG. 67 shows that when the user pushes the thumb-grip, the protrusion is lifted form the notch.

Figure 68:
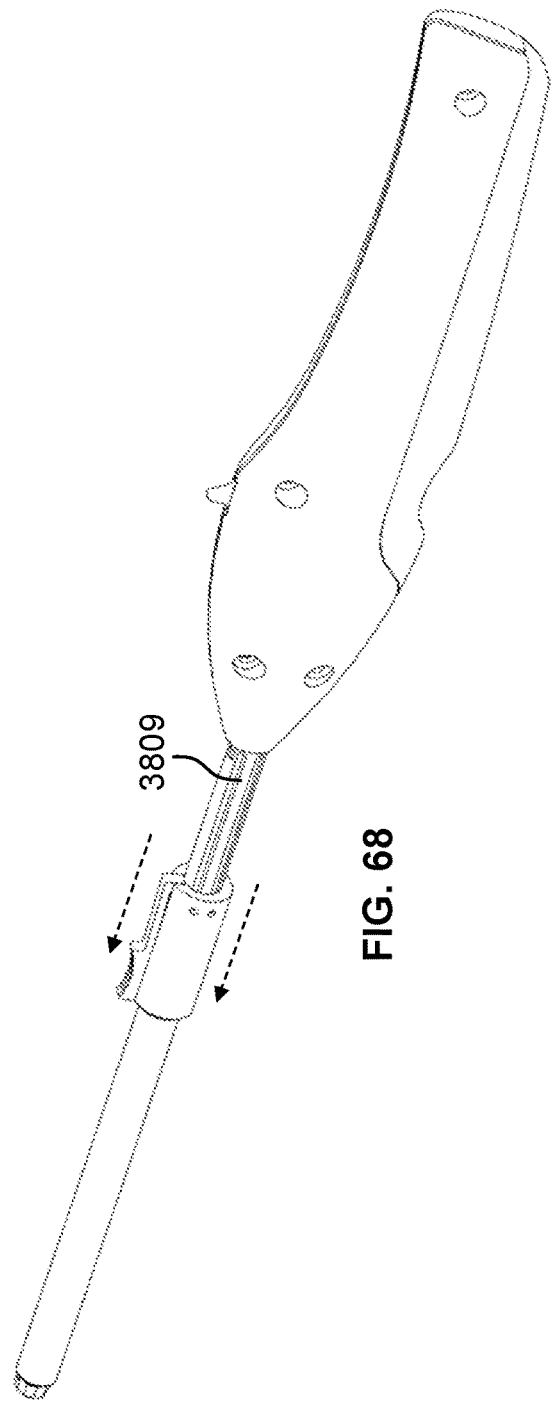
FIG. 68 shows pulling the sleeve forward over the shaft.

FIG. 68 shows pulling the sleeve 3807 forward over the shaft 3809.

Figure 69:
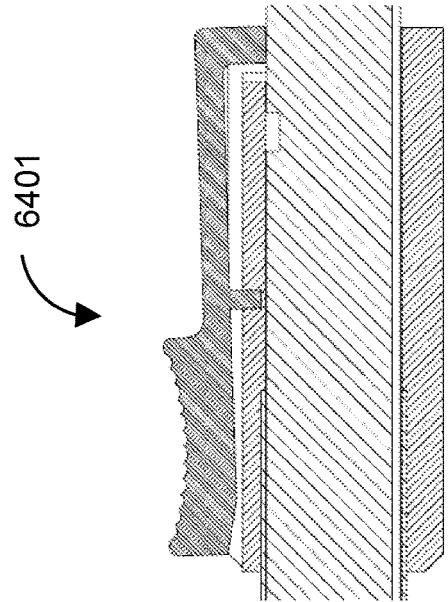
FIG. 69 shows the slider latch mechanism not fully forward.

FIG. 69 shows the slider latch mechanism 6401 when the sleeve 3807 is not yet pulled all the way forward.

Figure 70:
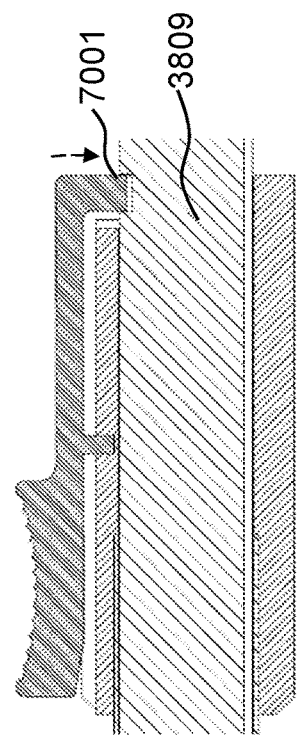
FIG. 70 shows the slider latch mechanism fully forward.

FIG. 70 shows the slider latch mechanism with the sleeve is pushed all the way forward, the latch is springe into the front notch 7001 at the shaft. As a result, the sleeve is locked in place during the insertion. Once the device is fully inserted, the surgeon releases the latch and slides back the sleeve.

In another feature that may be included with embodiments of an arthroscopic implant delivery device, there is a deformable plate that can be pulled "closed", or towards a cylindrical configuration and that can also be pulled "open", or towards a flat configuration through the inclusion of two separate tension wire systems that include a closing wire and an opening wire.

FIG. 71 shows a design with a bi-directional head 7115 which include two separate wires, one is for closing the plate (i.e., closing wire 7101) located below the hinges 7105 (living or conventional) and another for opening the device (i.e., opening wire 7102) located above the hinges. The depicted bi-directional head 7115 does not need to rely on the elasticity of the material for opening or closing operations.

FIG. 72 shows the bi-directional head 7115 in a cylindrical configuration. The device includes a reinforcing backbone 7177 and a limiter 7131. The bi-directional head can be actively pulled in both directions—to open and separately to close (i.e., towards a flat configuration and towards a cylindrical configuration).

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. An implant delivery device comprising:
   a handle;
   a shaft extending from the handle;
   a deformable plate carried on a distal portion of the shaft, the deformable plate comprising a first surface;
   a trigger on the handle, the trigger operably linked to the deformable plate to pull the deformable plate between a flat first configuration and a cylindrical second configuration; and
   a retainer mechanism on the deformable plate, the retainer mechanism operable to releasably hold a sheet-like implant against the first surface.

2. The device of claim 1, wherein the deformable plate is connected to the shaft via a flexible section that allows the plate to be angled away from the shaft and aligned to tissue during surgery.

3. The device of claim 1, wherein the first surface of the deformable plate is a single, monolithic piece of material.

4. The device of claim 1, wherein the deformable plate comprises a plurality of parallel channels in the first surface that operate as a living hinge allowing the deformable plate to be pulled from the flat first configuration to the cylindrical second configuration.

5. The device of claim 4, wherein the deformable plate assumes the flat first configuration at rest and the trigger pulls the deformable plate to the cylindrical second configuration.

6. The device of claim 4, further comprising a wire extending from the trigger and through a loop channel within the deformable plate, wherein tensioning the wire by the trigger pulls the deformable plate from the flat first configuration to the cylindrical second configuration.

7. The device of claim 4, wherein the first surface comprises extensions that overhang the channels, wherein when the deformable plate is pulled to the cylindrical second configuration, the extensions promote uniform deformation at each of the parallel channels.

8. The device of claim 1, wherein the deformable plate assumes the cylindrical second configuration at rest and the trigger pulls the deformable plate to the flat first configuration.

9. The device of claim 1, further comprising an insertion sleeve mounted over the shaft and slidable between a proximal and a distal position, wherein the deformable plate is extended out from a distal end of the insertion sleeve when the insertion sleeve is in the proximal position, and wherein the deformable plate is carried within a bore of the insertion sleeve when the plate is in the cylindrical second configuration with the insertion sleeve at the distal position.

10. The device of claim 1, wherein the deformable plate can be held, by one-handed operation of the trigger, in any position along a continuum between the flat first configuration and the cylindrical second configuration.

11. The device of claim 1, wherein deformable plate can be repositioned between the flat first configuration and the cylindrical second configuration without any kinetic shocks or snapping motions.

12. The device of claim 1, wherein the handle further comprises:
   a latch operably connected to the trigger and to the wire; and
   a lever spring operably connected to the trigger, wherein the latch is operable to releasably lock the delivery platform into a fixed position.

13. The device of claim 1, wherein when the deformable plate is in the cylindrical second configuration, the deformable plate may be inserted through a cannula used in arthroscopic keyhole surgery.

14. The device of claim 1, wherein when the deformable plate is in the cylindrical second configuration, the device is dimensioned for use in laparoscopic and endoscopic surgeries.

15. The device of claim 1, wherein the deformable plate further comprises one or more openings through which a surgical fastener may be delivered through the sheet-like implant.

16. The device of claim 1, wherein the first surface is dimensioned to carry a graft for rotator cuff repair.

17. The device of claim 1, wherein the deformable plate has angled edges that bias the deformable plate into the cylindrical second configuration when the deformable plate is pushed into the bore of a trocar while the deformable plate is not fully in the cylindrical second position.

18. The device of claim 1, wherein the deformable plate, when carrying an implant patch, may be, by manual operation of the trigger, deformed around a ligament or vessel to wrap and hold the implant patch around the ligament or vessel.

19. The device of claim 1, wherein the retainer mechanism on the deformable plate comprises one or more clips operable to elastically hold the implant to the first surface by a pressure, the device further comprising a loading card removably positioned in the one or more clips, the loading card holding the one or more clips at least somewhat in an open position.

20. The device of claim 19, wherein the loading card can be removed from the retainer mechanism by sliding the loading card sideways out of the clips, allowing the clips to close elastically towards the first surface of the plate.

* * * * *